US012766097B2

(12) United States Patent
Wang et al.

(10) Patent No.: US 12,766,097 B2
(45) Date of Patent: Oct. 20, 2026

(54) TREATMENT OF CNS LYMPHOMA AND SYSTEMIC LYMPHOMA WITH INTRACEREBROVENTRICULARLY ADMINISTERED CD19 CAR

(71) Applicant: City of Hope, Duarte, CA (US)

(72) Inventors: Xiuli Wang, Temple City, CA (US); Stephen J. Forman, Duarte, CA (US)

(73) Assignee: City of Hope, Duarte, CA (US)

( * ) Notice: Subject to any disclaimer, the term of this patent is extended or adjusted under 35 U.S.C. 154(b) by 1235 days.

(21) Appl. No.: 16/762,225

(22) PCT Filed: Nov. 7, 2018

(86) PCT No.: PCT/US2018/059668

§ 371 (c)(1), (2) Date: May 7, 2020

(87) PCT Pub. No.: WO2019/094498

PCT Pub. Date: May 16, 2019

(65) Prior Publication Data

US 2020/0345823 A1 Nov. 5, 2020

Related U.S. Application Data

(60) Provisional application No. 62/582,891, filed on Nov. 7, 2017.

(51) Int. Cl.

| | |
|---|---|
| ***A61K 40/31*** | (2025.01) |
| ***A61K 9/00*** | (2006.01) |
| ***A61K 40/11*** | (2025.01) |
| ***A61K 40/42*** | (2025.01) |
| ***A61P 35/00*** | (2006.01) |
| ***C12N 5/0783*** | (2010.01) |
| *A61K 39/00* | (2006.01) |

(52) U.S. Cl.

CPC .......... *A61K 9/0085* (2013.01); *A61K 9/0019* (2013.01); *A61K 40/11* (2025.01); *A61K 40/31* (2025.01); *A61K 40/4211* (2025.01); *A61P 35/00* (2018.01); *C12N 5/0636* (2013.01); *A61K 2039/545* (2013.01); *A61K 2039/804* (2018.08); *A61K 2239/29* (2023.05); *A61K 2239/31* (2023.05); *A61K 2239/38* (2023.05); *A61K 2239/47* (2023.05)

(58) Field of Classification Search

None

See application file for complete search history.

(56) References Cited

U.S. PATENT DOCUMENTS

| | | | | |
|---|---|---|---|---|
| 7,446,179 B2 | 11/2008 | Jensen et al. | | |
| 2011/0135696 A1* | 6/2011 | Isacson | A61M 5/178 | 435/378 |
| 2013/0280224 A1* | 10/2013 | Monsonego | A61P 25/16 | 514/17.7 |
| 2014/0271635 A1* | 9/2014 | Brogdon | C07K 14/70503 | 536/23.53 |
| 2017/0056534 A1* | 3/2017 | Pulé | A61K 39/0011 | |
| 2017/0137783 A1* | 5/2017 | Bedoya | A61P 35/00 | |

FOREIGN PATENT DOCUMENTS

| | | | |
|---|---|---|---|
| WO | WO-2015105522 A1 * | 7/2015 | A61K 39/39558 |
| WO | WO-2016044811 A1 * | 3/2016 | A61K 35/17 |

OTHER PUBLICATIONS

Palmer et al., Anti-CD19 Car T Cells in CNS Diffuse Large-B-Cell Lymphoma (NEJM, 2017, 377:783-784, published Aug. 24, 2017). (Year: 2017).*

Callaert et al., Traces of Prior Art: An analysis of non-patent references found in patent documents. Scientometrics, vol. 69, No. 1 Mar. 20, 2006 (Year: 2006).*

Brown et al., "Bioactivity and safety of IL13Rα2-redirected chimeric antigen receptor CD8+ T cells in patients with recurrent glioblastoma," Clinical Cancer Research, Sep. 15, 2015, 21(18):4062-72.

Brown et al., "Regression of glioblastoma after chimeric antigen receptor T-cell therapy," New England Journal of Medicine, Dec. 29, 2016, 375(26):2561-9.

Crossland et al., "T cells from tumor-immune mice nonspecifically expanded in vitro with anti-CD3 plus IL-2 retain specific function in vitro and can eradicate disseminated leukemia in vivo," The Journal of Immunology, Jun. 15, 1991, 146(12):4414-20.

Gust et al., "Endothelial activation and blood-brain barrier disruption in neurotoxicity after adoptive immunotherapy with CD19 CAR-T cells," Cancer Discovery, Dec. 1, 2017, 7(12):1404-19.

Hinrichs et al., "Human effector CD8+ T cells derived from naive rather than memory subsets possess superior traits for adoptive immunotherapy," Blood, The Journal of the American Society of Hematology, Jan. 20, 2011, 117(3):808-14.

Kowolik et al., "CD28 costimulation provided through a CD19-specific chimeric antigen receptor enhances in vivo persistence and antitumor efficacy of adoptively transferred T cells," Cancer Research, Nov. 15, 2006, 66(22):10995-1004.

Qian et al., "Advances in the treatment of newly diagnosed primary central nervous system lymphomas," Blood Research, Sep. 1, 2017, 52(3):159-66.

PCT International Report on Patentability in International Appln. No. PCT/US2018/059668, dated May 12, 2020, 7 pages.

PCT International Search Report and Written Opinion in International Appln. No. PCT/US2018/059668, dated Mar. 15, 2019, 15 pages.

Priceman et al., "Regional delivery of chimeric antigen receptor-engineered T cells effectively targets HER2+ breast Cancer metastasis to the brain," Clinical Cancer Research, Jan. 1, 2018, 24(1):95-105.

Wang et al., "Phenotypic and functional attributes of lentivirus modified CD19-specific human CD8+ central memory T cells manufactured at Clinical Scale," Journal of Immunotherapy, Nov. 2012, 35(9):689.

(Continued)

*Primary Examiner* — Arthur S Leonard

(74) *Attorney, Agent, or Firm* — Fish & Richardson P.C.

(57) ABSTRACT

An improved method of treating cancers CD19 CAR T cells by administering the CD19 CAR T cells to the central nervous system, e.g., by intracerebroventricular administration, is described.

19 Claims, 34 Drawing Sheets

Specification includes a Sequence Listing.

(56) References Cited

OTHER PUBLICATIONS

Wang et al., “New therapeutic approach for central nervous system lymphoma by CD19CAR T cells,” Journal for Immunotherapy of Cancer, Nov. 7, 2017, 5(2):108-9.
Wang et al., “Phase 1 studies of central memory-derived CD19 CAR T-cell therapy following autologous HSCT in patients with B-cell NHL,” Blood, Jun. 16, 2016, 127(24):2980-90.
Weng et al., “A novel generation 1928zT2 Car T cells induce remission in extramedullary relapse of acute lymphoblastic leukemia,” Journal of Hematology & Oncology, Dec. 2018, 11(1):1-2.
Willinger et al., “Molecular signatures distinguish human central memory from effector memory CD8 T cell subsets,” The Journal of Immunology, Nov. 1, 2005, 175(9):5895-903.
ClinicalTrials.gov [online], “Intracerebroventricular Administration of CD19-CAR T Cells (CD19CAR-CD28-CD3zeta-EGFRt-expressing Tcm-enriched T-lymphocytes) for the Treatment of Primary Central Nervous System Lymphoma,” NCT05625594, last updated Jul. 11, 2024, retrieved on Sep. 11, 2024, retrieved from URL<https://clinicaltrials.gov/study/NCT05625594?term=NCT05625594&rank=1>, 37 pages.
GenBank Accession No. J04132.1, “Human T cell receptor zeta-chain mRNA, complete cds” dated Jan. 12, 1995, 2 pages.
GenBank Accession No. M35160.1, “Human T4 surface glycoprotein CD4 gene, complete cds” dated Jan. 24, 1994, 2 pages.
GenBank Accession No. NM_001561.5, “*Homo sapiens* TNF receptor superfamily member 9 (TNFRSF9), mRNA” dated Oct. 7, 2016, 5 pages.
GenBank Accession No. NM_001768.6, “*Homo sapiens* CD8a molecule (CD8A), transcript variant 1, mRNA” dated Oct. 7, 2016, 4 pages.
GenBank Accession No. NM_006139.3, “*Homo sapiens* CD28 molecule (CD28), transcript variant 1, mRNA” dated Oct. 7, 2016, 5 pages.
qiagen.com [online], “Sample to Insight,” available on or before Sep. 5, 2024, via Internet Archive: Wayback Machine URL <https://web.archive.org/web/20240828132302/https://www.qiagen.com/de-de>, retrieved on Sep. 11, 2024, URL<https://www.qiagen.com/us>, 5 pages.
Wang et al., “The Cerebroventricular Environment Modifies CAR T Cells for Potent Activity against Both Central Nervous System and Systemic Lymphoma,” Cancer Immunology Research, Jan. 2021, 9(1):75-88.

* cited by examiner

MLLLVTSLLLCELPHPAFLLIPDIQMTQTTSSLSASLGDRVTISCRASQDISKYLNWYQQ
GMCSFRa signal CD19 scFv
KPDGTVKLLIYHTSRLHSGVPSRFSGSGSGTDYSLTISNLEQEDIATYFCQQGNTLPYTF

GGGTKLEITGSTSGSGKPGSGEGSTKGEVKLQESGPGLVAPSQSLSVTCTVSGVSLPDYG

VSWIRQPPRKGLEWLGVIWGSETTYYNSALKSRLTIIKDNSKSQVFLKMNSLQTDDTAIY

YCAKHYYYGGSYAMDYWGQGTSVTVSSESKYGPPCPPCPAPEFEGGPSVFLFPPKPKDTL
IgG4(SmP)(L235E, N297Q)

MISRTPEVTCVVVDVSQEDPEVQFNWYVDGVEVHNAKTKPREEQFQSTYRVVSVLTVLHQ

DWLNGKEYKCKVSNKGLPSSIEKTISKAKGQPREPQVYTLPPSQEEMTKNQVSLTCLVKG

FYPSDIAVEWESNGQPENNYKTTPPVLDSDGSFFLYSRLTVDKSRWQEGNVFSCSVMHEA

LHNHYTQKSLSLSLGKMFWVLVVVGGVLACYSLLVTVAFIIFWVRSKRSRGGHSDYMNMT
CD28 TM CD28 Cyto

PRRPGPTRKHYQPYAPPRDFAAYRSGGGRVKFSRSADAPAYQQGQNQLYNELNLGRREEY
Zeta

DVLDKRRGRDPEMGGKPRRKNPQEGLYNELQKDKMAEAYSEIGMKGERRRGKGHDGLYQG

LSTATKDTYDALHMQALPPR

FIG. 1A

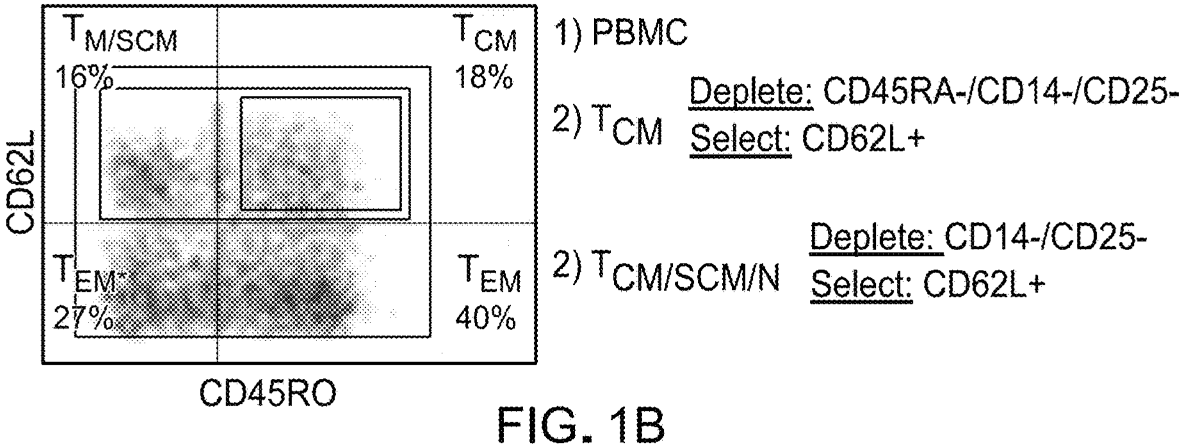

FIG. 1B

LEGGGEGRGSLLTCGDVEENPGPRMLLLVTSLLLCELPHPAFLLIPRKVCNGIGIGEFKDSLSIN
T2A GMCSFRa signal peptide EGFRt

ATNIKHFKNCTSISGDLHILPVAFRGDSFTHTPPLDPQELDILKTVKEITGFLLIQAWPENRTDL

HAFENLEIIRGRTKQHGQFSLAVVSLNITSLGLRSLKEISDGDVIISGNKNLCYANTINWKKLFG

TSGQKTKIISNRGENSCKATGQVCHALCSPEGCWGPEPRDCVSCRNVSRGRECVDKCNLLE

GEPREFVENSECIQCHPECLPQAMNITCTGRGPDNCIQCAHYIDGPHCVKTCPAGVMGEN

NTLVWKYADAGHVCHLCHPNCTYGCTGPGLEGCPTNGPKIPSIATGMVGALLLLLVVALGIG

LFM

FIG. 19A

DIQMTQTTSSLSASLGDRVTISCRASQDISKYLNWYQQKPDGTVKLLIYHTSRLHSGVPSRFSGSGSGTDYSLTISNLEQEDIATYFCQQGNTLPYTF
GGGTKLEITGSTSGSGKPGSGEGSTKGEVKLQESGPGLVAPSQSLSVTCTVSGVSLPDYGVSWIRQPPRKGLEWLGVIWGSETTYYNSALKSRLTIIKDNSK
SQVFLKMNSLQTDDTAIYYCAKHYYYGGSYAMDYWGQGTSVTVSS

FIG. 19B

ESKYGPPCPSCPAPEFEGGPSVFLFPPKPKDTL
IgG4(L235E, N297Q)
MISRTPEVTCVVVDVSQEDPEVQFNWYVDGVEVHNAKTKPREEQFQSTYRVVSVLTVLHQ

DWLNGKEYKCKVSNKGLPSSIEKTISKAKGQPREPQVYTLPPSQEEMTKNQVSLTCLVKG

FYPSDIAVEWESNGQPENNYKTTPPVLDSDGSFFLYSRLTVDKSRWQEGNVFSCSVMHEA

LHNHYTQKSLSLSLGKMFWVLVVVGGVLACYSLLVTVAFIIFWVRSKRSRGGHSDYMNMT
CD28 TM CD28 Cyto
PRRPGPTRKHYQPYAPPRDFAAYRSGGGRVKFSRSADAPAYQQGQNQLYNELNLGRREEY
Zeta
DVLDKRRGRDPEMGGKPRRKNPQEGLYNELQKDKMAEAYSEIGMKGERRRGKGHDGLYQG

LSTATKDTYDALHMQALPPR

FIG. 19C

DIQMTQTTSSLSASLGDRVTISCRASQDISKYLNWYQQ
CD19 scFv

KPDGTVKLLIYHTSRLHSGVPSRFSGSGSGTDYSLTISNLEQEDIATYFCQQGNTLPYTF

GGGTKLEITGSTSGSGKPGSGEGSTKGEVKLQESGPGLVAPSQSLSVTCTVSGVSLPDYG

VSWIRQPPRKGLEWLGVIWGSETTYYNSALKSRLTIIKDNSKSQVFLKMNSLQTDDTAIY

YCAKHYYYGGSYAMDYWGQGTSVTVSSESKYGPPCPPCPAPEFEGGPSVFLFPPKPKDTL
IgG4(SmP)(L235E,N297Q)

MISRTPEVTCVVVDVSQEDPEVQFNWYVDGVEVHNAKTKPREEQFQSTYRVVSVLTVLHQ

DWLNGKEYKCKVSNKGLPSSIEKTISKAKGQPREPQVYTLPPSQEEMTKNQVSLTCLVKG

FYPSDIAVEWESNGQPENNYKTTPPVLDSDGSFFLYSRLTVDKSRWQEGNVFSCSVMHEA

LHNHYTQKSLSLSLGKMFWVLVVVGGVLACYSLLVTVAFIIFWVRSKRSRGGHSDYMNMT
CD28 TM CD28 Cyto

PRRPGPTRKHYQPYAPPRDFAAYRSGGGRVKFSRSADAPAYQQGQNQLYNELNLGRREEY
Zeta

DVLDKRRGRDPEMGGKPRRKNPQEGLYNELQKDKMAEAYSEIGMKGERRRGKGHDGLYQG

LSTATKDTYDALHMQALPPR

FIG. 20

MLLLVTSLLLCELPHPAFLLIPDIQMTQTTSSLSASLGDRVTISCRASQDISKYLNWYQQ
GMCSFRa signal CD19 scFv

KPDGTVKLLIYHTSRLHSGVPSRFSGSGSGTDYSLTISNLEQEDIATYFCQQGNTLPYTF

GGGTKLEITGSTSGSGKPGSGEGSTKGEVKLQESGPGLVAPSQSLSVTCTVSGVSLPDYG

VSWIRQPPRKGLEWLGVIWGSETTYYNSALKSRLTIIKDNSKSQVFLKMNSLQTDDTAIY

YCAKHYYYGGSYAMDYWGQGTSVTVSSESKYGPPCPSCPAPEFEGGPSVFLFPPKPKDTL
IgG4(L235E,N297Q)

MISRTPEVTCVVVDVSQEDPEVQFNWYVDGVEVHNAKTKPREEQFQSTYRVVSVLTVLHQ

DWLNGKEYKCKVSNKGLPSSIEKTISKAKGQPREPQVYTLPPSQEEMTKNQVSLTCLVKG

FYPSDIAVEWESNGQPENNYKTTPPVLDSDGSFFLYSRLTVDKSRWQEGNVFSCSVMHEA

LHNHYTQKSLSLSLGKMFWVLVVVGGVLACYSLLVTVAFIIFWVRSKRSRGGHSDYMNMT
CD28 TM CD28 Cyto

PRRPGPTRKHYQPYAPPRDFAAYRSGGGRVKFSRSADAPAYQQGQNQLYNELNLGRREEY
Zeta

DVLDKRRGRDPEMGGKPRRKNPQEGLYNELQKDKMAEAYSEIGMKGERRRGKGHDGLYQG

LSTATKDTYDALHMQALPPR

FIG. 21

DIQMTQTTSSLSASLGDRVTISCRASQDISKYLNWYQQ
CD19 scFv

KPDGTVKLLIYHTSRLHSGVPSRFSGSGSGTDYSLTISNLEQEDIATYFCQQGNTLPYTF

GGGTKLEITGSTSGSGKPGSGEGSTKGEVKLQESGPGLVAPSQSLSVTCTVSGVSLPDYG

VSWIRQPPRKGLEWLGVIWGSETTYYNSALKSRLTIIKDNSKSQVFLKMNSLQTDDTAIY

YCAKHYYYGGSYAMDYWGQGTSVTVSSESKYGPPCPSCPAPEFEGGPSVFLFPPKPKDTL
IgG4(L235E,N297Q)

MISRTPEVTCVVVDVSQEDPEVQFNWYVDGVEVHNAKTKPREEQFQSTYRVVSVLTVLHQ

DWLNGKEYKCKVSNKGLPSSIEKTISKAKGQPREPQVYTLPPSQEEMTKNQVSLTCLVKG

FYPSDIAVEWESNGQPENNYKTTPPVLDSDGSFFLYSRLTVDKSRWQEGNVFSCSVMHEA

LHNHYTQKSLSLSLGKMFWVLVVVGGVLACYSLLVTVAFIIFWVRSKRSRGGHSDYMNMT
CD28 TM CD28 Cyto

PRRPGPTRKHYQPYAPPRDFAAYRSGGGRVKFSRSADAPAYQQGQNQLYNELNLGRREEY
Zeta
DVLDKRRGRDPEMGGKPRRKNPQEGLYNELQKDKMAEAYSEIGMKGERRRGKGHDGLYQG

LSTATKDTYDALHMQALPPR

FIG. 22

SEQUENCE LISTING

```
<160> NUMBER OF SEQ ID NOS: 34

<210> SEQ ID NO 1
<211> LENGTH: 680
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1

Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Ser Thr Ser Gly Ser Gly Lys Pro Gly Ser Gly Glu Gly Ser
    130                 135                 140

Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
                165                 170                 175

Pro Asp Tyr Gly Val Ser Trp Ile Arg Gln Pro Pro Arg Lys Gly Leu
            180                 185                 190

Glu Trp Leu Gly Val Ile Trp Gly Ser Glu Thr Thr Tyr Tyr Asn Ser
        195                 200                 205

Ala Leu Lys Ser Arg Leu Thr Ile Ile Lys Asp Asn Ser Lys Ser Gln
```

-continued

```
    210                 215                 220

Val Phe Leu Lys Met Asn Ser Leu Gln Thr Asp Asp Thr Ala Ile Tyr
225                 230                 235                 240

Tyr Cys Ala Lys His Tyr Tyr Tyr Gly Gly Ser Tyr Ala Met Asp Tyr
                245                 250                 255

Trp Gly Gln Gly Thr Ser Val Thr Val Ser Ser Glu Ser Lys Tyr Gly
            260                 265                 270

Pro Pro Cys Pro Pro Cys Pro Ala Pro Glu Phe Glu Gly Gly Pro Ser
        275                 280                 285

Val Phe Leu Phe Pro Pro Lys Pro Lys Asp Thr Leu Met Ile Ser Arg
    290                 295                 300

Thr Pro Glu Val Thr Cys Val Val Val Asp Val Ser Gln Glu Asp Pro
305                 310                 315                 320

Glu Val Gln Phe Asn Trp Tyr Val Asp Gly Val Glu Val His Asn Ala
                325                 330                 335

Lys Thr Lys Pro Arg Glu Glu Gln Phe Gln Ser Thr Tyr Arg Val Val
            340                 345                 350

Ser Val Leu Thr Val Leu His Gln Asp Trp Leu Asn Gly Lys Glu Tyr
        355                 360                 365

Lys Cys Lys Val Ser Asn Lys Gly Leu Pro Ser Ser Ile Glu Lys Thr
    370                 375                 380

Ile Ser Lys Ala Lys Gly Gln Pro Arg Glu Pro Gln Val Tyr Thr Leu
385                 390                 395                 400

Pro Pro Ser Gln Glu Glu Met Thr Lys Asn Gln Val Ser Leu Thr Cys
                405                 410                 415

Leu Val Lys Gly Phe Tyr Pro Ser Asp Ile Ala Val Glu Trp Glu Ser
            420                 425                 430

Asn Gly Gln Pro Glu Asn Asn Tyr Lys Thr Thr Pro Pro Val Leu Asp
        435                 440                 445

Ser Asp Gly Ser Phe Phe Leu Tyr Ser Arg Leu Thr Val Asp Lys Ser
    450                 455                 460

Arg Trp Gln Glu Gly Asn Val Phe Ser Cys Ser Val Met His Glu Ala
465                 470                 475                 480

Leu His Asn His Tyr Thr Gln Lys Ser Leu Ser Leu Ser Leu Gly Lys
                485                 490                 495

Met Phe Trp Val Leu Val Val Val Gly Gly Val Leu Ala Cys Tyr Ser
            500                 505                 510

Leu Leu Val Thr Val Ala Phe Ile Ile Phe Trp Val Arg Ser Lys Arg
        515                 520                 525

Ser Arg Gly Gly His Ser Asp Tyr Met Asn Met Thr Pro Arg Arg Pro
    530                 535                 540

Gly Pro Thr Arg Lys His Tyr Gln Pro Tyr Ala Pro Pro Arg Asp Phe
545                 550                 555                 560

Ala Ala Tyr Arg Ser Gly Gly Gly Arg Val Lys Phe Ser Arg Ser Ala
                565                 570                 575

Asp Ala Pro Ala Tyr Gln Gln Gly Gln Asn Gln Leu Tyr Asn Glu Leu
            580                 585                 590

Asn Leu Gly Arg Arg Glu Glu Tyr Asp Val Leu Asp Lys Arg Arg Gly
        595                 600                 605

Arg Asp Pro Glu Met Gly Gly Lys Pro Arg Arg Lys Asn Pro Gln Glu
    610                 615                 620

Gly Leu Tyr Asn Glu Leu Gln Lys Asp Lys Met Ala Glu Ala Tyr Ser
625                 630                 635                 640
```

```
Glu Ile Gly Met Lys Gly Glu Arg Arg Arg Gly Lys Gly His Asp Gly
                645                 650                 655

Leu Tyr Gln Gly Leu Ser Thr Ala Thr Lys Asp Thr Tyr Asp Ala Leu
            660                 665                 670

His Met Gln Ala Leu Pro Pro Arg
        675                 680


<210> SEQ ID NO 2
<211> LENGTH: 658
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
        115                 120                 125

Leu Gln Glu Ser Gly Pro Gly Leu Val Ala Pro Ser Gln Ser Leu Ser
    130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
        195                 200                 205

Ser Leu Gln Thr Asp Asp Thr Ala Ile Tyr Tyr Cys Ala Lys His Tyr
    210                 215                 220

Tyr Tyr Gly Gly Ser Tyr Ala Met Asp Tyr Trp Gly Gln Gly Thr Ser
225                 230                 235                 240

Val Thr Val Ser Ser Glu Ser Lys Tyr Gly Pro Pro Cys Pro Pro Cys
                245                 250                 255

Pro Ala Pro Glu Phe Glu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser Gln Glu Asp Pro Glu Val Gln Phe Asn Trp
    290                 295                 300
```

```
Tyr Val Asp Gly Val Glu Val His Asn Ala Lys Thr Lys Pro Arg Glu
305                 310                 315                 320

Glu Gln Phe Gln Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Gly Leu Pro Ser Ser Ile Glu Lys Thr Ile Ser Lys Ala Lys Gly
        355                 360                 365

Gln Pro Arg Glu Pro Gln Val Tyr Thr Leu Pro Pro Ser Gln Glu Glu
    370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Arg Leu Thr Val Asp Lys Ser Arg Trp Gln Glu Gly Asn
        435                 440                 445

Val Phe Ser Cys Ser Val Met His Glu Ala Leu His Asn His Tyr Thr
    450                 455                 460

Gln Lys Ser Leu Ser Leu Ser Leu Gly Lys Met Phe Trp Val Leu Val
465                 470                 475                 480

Val Val Gly Gly Val Leu Ala Cys Tyr Ser Leu Leu Val Thr Val Ala
                485                 490                 495

Phe Ile Ile Phe Trp Val Arg Ser Lys Arg Ser Arg Gly Gly His Ser
            500                 505                 510

Asp Tyr Met Asn Met Thr Pro Arg Arg Pro Gly Pro Thr Arg Lys His
        515                 520                 525

Tyr Gln Pro Tyr Ala Pro Pro Arg Asp Phe Ala Ala Tyr Arg Ser Gly
    530                 535                 540

Gly Gly Arg Val Lys Phe Ser Arg Ser Ala Asp Ala Pro Ala Tyr Gln
545                 550                 555                 560

Gln Gly Gln Asn Gln Leu Tyr Asn Glu Leu Asn Leu Gly Arg Arg Glu
                565                 570                 575

Glu Tyr Asp Val Leu Asp Lys Arg Arg Gly Arg Asp Pro Glu Met Gly
            580                 585                 590

Gly Lys Pro Arg Arg Lys Asn Pro Gln Glu Gly Leu Tyr Asn Glu Leu
        595                 600                 605

Gln Lys Asp Lys Met Ala Glu Ala Tyr Ser Glu Ile Gly Met Lys Gly
    610                 615                 620

Glu Arg Arg Arg Gly Lys Gly His Asp Gly Leu Tyr Gln Gly Leu Ser
625                 630                 635                 640

Thr Ala Thr Lys Asp Thr Tyr Asp Ala Leu His Met Gln Ala Leu Pro
                645                 650                 655

Pro Arg


<210> SEQ ID NO 3
<211> LENGTH: 245
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3
```

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
        115                 120                 125

Leu Gln Glu Ser Gly Pro Gly Leu Val Ala Pro Ser Gln Ser Leu Ser
    130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
        195                 200                 205

Ser Leu Gln Thr Asp Asp Thr Ala Ile Tyr Tyr Cys Ala Lys His Tyr
    210                 215                 220

Tyr Tyr Gly Gly Ser Tyr Ala Met Asp Tyr Trp Gly Gln Gly Thr Ser
225                 230                 235                 240

Val Thr Val Ser Ser
                245
```

<210> SEQ ID NO 4
<211> LENGTH: 680
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 4

```
Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95
```

-continued

```
Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Ser Thr Ser Gly Ser Gly Lys Pro Gly Ser Gly Glu Gly Ser
    130                 135                 140

Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
                165                 170                 175

Pro Asp Tyr Gly Val Ser Trp Ile Arg Gln Pro Pro Arg Lys Gly Leu
            180                 185                 190

Glu Trp Leu Gly Val Ile Trp Gly Ser Glu Thr Thr Tyr Tyr Asn Ser
        195                 200                 205

Ala Leu Lys Ser Arg Leu Thr Ile Ile Lys Asp Asn Ser Lys Ser Gln
    210                 215                 220

Val Phe Leu Lys Met Asn Ser Leu Gln Thr Asp Asp Thr Ala Ile Tyr
225                 230                 235                 240

Tyr Cys Ala Lys His Tyr Tyr Tyr Gly Gly Ser Tyr Ala Met Asp Tyr
                245                 250                 255

Trp Gly Gln Gly Thr Ser Val Thr Val Ser Ser Glu Ser Lys Tyr Gly
            260                 265                 270

Pro Pro Cys Pro Ser Cys Pro Ala Pro Glu Phe Glu Gly Gly Pro Ser
        275                 280                 285

Val Phe Leu Phe Pro Pro Lys Pro Lys Asp Thr Leu Met Ile Ser Arg
    290                 295                 300

Thr Pro Glu Val Thr Cys Val Val Val Asp Val Ser Gln Glu Asp Pro
305                 310                 315                 320

Glu Val Gln Phe Asn Trp Tyr Val Asp Gly Val Glu Val His Asn Ala
                325                 330                 335

Lys Thr Lys Pro Arg Glu Glu Gln Phe Asn Ser Thr Tyr Arg Val Val
            340                 345                 350

Ser Val Leu Thr Val Leu His Gln Asp Trp Leu Asn Gly Lys Glu Tyr
        355                 360                 365

Lys Cys Lys Val Ser Asn Lys Gly Leu Pro Ser Ser Ile Glu Lys Thr
    370                 375                 380

Ile Ser Lys Ala Lys Gly Gln Pro Arg Glu Pro Gln Val Tyr Thr Leu
385                 390                 395                 400

Pro Pro Ser Gln Glu Glu Met Thr Lys Asn Gln Val Ser Leu Thr Cys
                405                 410                 415

Leu Val Lys Gly Phe Tyr Pro Ser Asp Ile Ala Val Glu Trp Glu Ser
            420                 425                 430

Asn Gly Gln Pro Glu Asn Asn Tyr Lys Thr Thr Pro Pro Val Leu Asp
        435                 440                 445

Ser Asp Gly Ser Phe Phe Leu Tyr Ser Arg Leu Thr Val Asp Lys Ser
    450                 455                 460

Arg Trp Gln Glu Gly Asn Val Phe Ser Cys Ser Val Met His Glu Ala
465                 470                 475                 480

Leu His Asn His Tyr Thr Gln Lys Ser Leu Ser Leu Ser Leu Gly Lys
                485                 490                 495

Met Phe Trp Val Leu Val Val Val Gly Gly Val Leu Ala Cys Tyr Ser
            500                 505                 510

Leu Leu Val Thr Val Ala Phe Ile Ile Phe Trp Val Arg Ser Lys Arg
```

-continued

```
        515                 520                 525

Ser Arg Gly Gly His Ser Asp Tyr Met Asn Met Thr Pro Arg Arg Pro
    530                 535                 540

Gly Pro Thr Arg Lys His Tyr Gln Pro Tyr Ala Pro Pro Arg Asp Phe
545                 550                 555                 560

Ala Ala Tyr Arg Ser Gly Gly Gly Arg Val Lys Phe Ser Arg Ser Ala
                565                 570                 575

Asp Ala Pro Ala Tyr Gln Gln Gly Gln Asn Gln Leu Tyr Asn Glu Leu
            580                 585                 590

Asn Leu Gly Arg Arg Glu Glu Tyr Asp Val Leu Asp Lys Arg Arg Gly
        595                 600                 605

Arg Asp Pro Glu Met Gly Gly Lys Pro Arg Arg Lys Asn Pro Gln Glu
    610                 615                 620

Gly Leu Tyr Asn Glu Leu Gln Lys Asp Lys Met Ala Glu Ala Tyr Ser
625                 630                 635                 640

Glu Ile Gly Met Lys Gly Glu Arg Arg Arg Gly Lys Gly His Asp Gly
                645                 650                 655

Leu Tyr Gln Gly Leu Ser Thr Ala Thr Lys Asp Thr Tyr Asp Ala Leu
            660                 665                 670

His Met Gln Ala Leu Pro Pro Arg
        675                 680


<210> SEQ ID NO 5
<211> LENGTH: 658
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
        115                 120                 125

Leu Gln Glu Ser Gly Pro Gly Leu Val Ala Pro Ser Gln Ser Leu Ser
    130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190
```

-continued

```
Thr Ile Ile Lys Asp Asn Ser Lys Ser Gln Val Phe Leu Lys Met Asn
        195                 200                 205

Ser Leu Gln Thr Asp Asp Thr Ala Ile Tyr Tyr Cys Ala Lys His Tyr
    210                 215                 220

Tyr Tyr Gly Gly Ser Tyr Ala Met Asp Tyr Trp Gly Gln Gly Thr Ser
225                 230                 235                 240

Val Thr Val Ser Ser Glu Ser Lys Tyr Gly Pro Pro Cys Pro Ser Cys
                245                 250                 255

Pro Ala Pro Glu Phe Glu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser Gln Glu Asp Pro Glu Val Gln Phe Asn Trp
    290                 295                 300

Tyr Val Asp Gly Val Glu Val His Asn Ala Lys Thr Lys Pro Arg Glu
305                 310                 315                 320

Glu Gln Phe Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Gly Leu Pro Ser Ser Ile Glu Lys Thr Ile Ser Lys Ala Lys Gly
        355                 360                 365

Gln Pro Arg Glu Pro Gln Val Tyr Thr Leu Pro Pro Ser Gln Glu Glu
    370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Arg Leu Thr Val Asp Lys Ser Arg Trp Gln Glu Gly Asn
        435                 440                 445

Val Phe Ser Cys Ser Val Met His Glu Ala Leu His Asn His Tyr Thr
    450                 455                 460

Gln Lys Ser Leu Ser Leu Ser Leu Gly Lys Met Phe Trp Val Leu Val
465                 470                 475                 480

Val Val Gly Gly Val Leu Ala Cys Tyr Ser Leu Leu Val Thr Val Ala
                485                 490                 495

Phe Ile Ile Phe Trp Val Arg Ser Lys Arg Ser Arg Gly Gly His Ser
            500                 505                 510

Asp Tyr Met Asn Met Thr Pro Arg Arg Pro Gly Pro Thr Arg Lys His
        515                 520                 525

Tyr Gln Pro Tyr Ala Pro Pro Arg Asp Phe Ala Ala Tyr Arg Ser Gly
    530                 535                 540

Gly Gly Arg Val Lys Phe Ser Arg Ser Ala Asp Ala Pro Ala Tyr Gln
545                 550                 555                 560

Gln Gly Gln Asn Gln Leu Tyr Asn Glu Leu Asn Leu Gly Arg Arg Glu
                565                 570                 575

Glu Tyr Asp Val Leu Asp Lys Arg Arg Gly Arg Asp Pro Glu Met Gly
            580                 585                 590

Gly Lys Pro Arg Arg Lys Asn Pro Gln Glu Gly Leu Tyr Asn Glu Leu
        595                 600                 605
```

-continued

```
Gln Lys Asp Lys Met Ala Glu Ala Tyr Ser Glu Ile Gly Met Lys Gly
    610                 615                 620

Glu Arg Arg Arg Gly Lys Gly His Asp Gly Leu Tyr Gln Gly Leu Ser
625                 630                 635                 640

Thr Ala Thr Lys Asp Thr Tyr Asp Ala Leu His Met Gln Ala Leu Pro
                645                 650                 655

Pro Arg


<210> SEQ ID NO 6
<211> LENGTH: 381
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Leu Glu Gly Gly Gly Glu Gly Arg Gly Ser Leu Leu Thr Cys Gly Asp
1               5                   10                  15

Val Glu Glu Asn Pro Gly Pro Arg Met Leu Leu Leu Val Thr Ser Leu
            20                  25                  30

Leu Leu Cys Glu Leu Pro His Pro Ala Phe Leu Leu Ile Pro Arg Lys
        35                  40                  45

Val Cys Asn Gly Ile Gly Ile Gly Glu Phe Lys Asp Ser Leu Ser Ile
    50                  55                  60

Asn Ala Thr Asn Ile Lys His Phe Lys Asn Cys Thr Ser Ile Ser Gly
65                  70                  75                  80

Asp Leu His Ile Leu Pro Val Ala Phe Arg Gly Asp Ser Phe Thr His
                85                  90                  95

Thr Pro Pro Leu Asp Pro Gln Glu Leu Asp Ile Leu Lys Thr Val Lys
            100                 105                 110

Glu Ile Thr Gly Phe Leu Leu Ile Gln Ala Trp Pro Glu Asn Arg Thr
        115                 120                 125

Asp Leu His Ala Phe Glu Asn Leu Glu Ile Ile Arg Gly Arg Thr Lys
    130                 135                 140

Gln His Gly Gln Phe Ser Leu Ala Val Val Ser Leu Asn Ile Thr Ser
145                 150                 155                 160

Leu Gly Leu Arg Ser Leu Lys Glu Ile Ser Asp Gly Asp Val Ile Ile
                165                 170                 175

Ser Gly Asn Lys Asn Leu Cys Tyr Ala Asn Thr Ile Asn Trp Lys Lys
            180                 185                 190

Leu Phe Gly Thr Ser Gly Gln Lys Thr Lys Ile Ile Ser Asn Arg Gly
        195                 200                 205

Glu Asn Ser Cys Lys Ala Thr Gly Gln Val Cys His Ala Leu Cys Ser
    210                 215                 220

Pro Glu Gly Cys Trp Gly Pro Glu Pro Arg Asp Cys Val Ser Cys Arg
225                 230                 235                 240

Asn Val Ser Arg Gly Arg Glu Cys Val Asp Lys Cys Asn Leu Leu Glu
                245                 250                 255

Gly Glu Pro Arg Glu Phe Val Glu Asn Ser Glu Cys Ile Gln Cys His
            260                 265                 270

Pro Glu Cys Leu Pro Gln Ala Met Asn Ile Thr Cys Thr Gly Arg Gly
        275                 280                 285

Pro Asp Asn Cys Ile Gln Cys Ala His Tyr Ile Asp Gly Pro His Cys
    290                 295                 300
```

Val Lys Thr Cys Pro Ala Gly Val Met Gly Glu Asn Asn Thr Leu Val
305 310 315 320

Trp Lys Tyr Ala Asp Ala Gly His Val Cys His Leu Cys His Pro Asn
325 330 335

Cys Thr Tyr Gly Cys Thr Gly Pro Gly Leu Glu Gly Cys Pro Thr Asn
340 345 350

Gly Pro Lys Ile Pro Ser Ile Ala Thr Gly Met Val Gly Ala Leu Leu
355 360 365

Leu Leu Leu Val Val Ala Leu Gly Ile Gly Leu Phe Met
370 375 380

<210> SEQ ID NO 7
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 7

Leu Glu Gly Gly Gly Glu Gly Arg Gly Ser Leu Leu Thr Cys Gly Asp
1 5 10 15

Val Glu Glu Asn Pro Gly Pro Arg
20

<210> SEQ ID NO 8
<211> LENGTH: 335
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 8

Arg Lys Val Cys Asn Gly Ile Gly Ile Gly Glu Phe Lys Asp Ser Leu
1 5 10 15

Ser Ile Asn Ala Thr Asn Ile Lys His Phe Lys Asn Cys Thr Ser Ile
20 25 30

Ser Gly Asp Leu His Ile Leu Pro Val Ala Phe Arg Gly Asp Ser Phe
35 40 45

Thr His Thr Pro Pro Leu Asp Pro Gln Glu Leu Asp Ile Leu Lys Thr
50 55 60

Val Lys Glu Ile Thr Gly Phe Leu Leu Ile Gln Ala Trp Pro Glu Asn
65 70 75 80

Arg Thr Asp Leu His Ala Phe Glu Asn Leu Glu Ile Ile Arg Gly Arg
85 90 95

Thr Lys Gln His Gly Gln Phe Ser Leu Ala Val Val Ser Leu Asn Ile
100 105 110

Thr Ser Leu Gly Leu Arg Ser Leu Lys Glu Ile Ser Asp Gly Asp Val
115 120 125

Ile Ile Ser Gly Asn Lys Asn Leu Cys Tyr Ala Asn Thr Ile Asn Trp
130 135 140

Lys Lys Leu Phe Gly Thr Ser Gly Gln Lys Thr Lys Ile Ile Ser Asn
145 150 155 160

Arg Gly Glu Asn Ser Cys Lys Ala Thr Gly Gln Val Cys His Ala Leu
165 170 175

-continued

```
Cys Ser Pro Glu Gly Cys Trp Gly Pro Glu Pro Arg Asp Cys Val Ser
            180                 185                 190

Cys Arg Asn Val Ser Arg Gly Arg Glu Cys Val Asp Lys Cys Asn Leu
        195                 200                 205

Leu Glu Gly Glu Pro Arg Glu Phe Val Glu Asn Ser Glu Cys Ile Gln
    210                 215                 220

Cys His Pro Glu Cys Leu Pro Gln Ala Met Asn Ile Thr Cys Thr Gly
225                 230                 235                 240

Arg Gly Pro Asp Asn Cys Ile Gln Cys Ala His Tyr Ile Asp Gly Pro
                245                 250                 255

His Cys Val Lys Thr Cys Pro Ala Gly Val Met Gly Glu Asn Asn Thr
            260                 265                 270

Leu Val Trp Lys Tyr Ala Asp Ala Gly His Val Cys His Leu Cys His
        275                 280                 285

Pro Asn Cys Thr Tyr Gly Cys Thr Gly Pro Gly Leu Glu Gly Cys Pro
    290                 295                 300

Thr Asn Gly Pro Lys Ile Pro Ser Ile Ala Thr Gly Met Val Gly Ala
305                 310                 315                 320

Leu Leu Leu Leu Leu Val Val Ala Leu Gly Ile Gly Leu Phe Met
                325                 330                 335


<210> SEQ ID NO 9
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Met Leu Leu Leu Val Thr Ser Leu Leu Leu Cys Glu Leu Pro His Pro
1               5                   10                  15

Ala Phe Leu Leu Ile Pro
            20


<210> SEQ ID NO 10
<211> LENGTH: 413
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Glu Ser Lys Tyr Gly Pro Pro Cys Pro Ser Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Gln Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
```

-continued

```
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys Met Phe Trp Val Leu Val Val Val Gly Gly Val
225                 230                 235                 240

Leu Ala Cys Tyr Ser Leu Leu Val Thr Val Ala Phe Ile Ile Phe Trp
                245                 250                 255

Val Arg Ser Lys Arg Ser Arg Gly Gly His Ser Asp Tyr Met Asn Met
            260                 265                 270

Thr Pro Arg Arg Pro Gly Pro Thr Arg Lys His Tyr Gln Pro Tyr Ala
        275                 280                 285

Pro Pro Arg Asp Phe Ala Ala Tyr Arg Ser Gly Gly Gly Arg Val Lys
    290                 295                 300

Phe Ser Arg Ser Ala Asp Ala Pro Ala Tyr Gln Gln Gly Gln Asn Gln
305                 310                 315                 320

Leu Tyr Asn Glu Leu Asn Leu Gly Arg Arg Glu Glu Tyr Asp Val Leu
                325                 330                 335

Asp Lys Arg Arg Gly Arg Asp Pro Glu Met Gly Gly Lys Pro Arg Arg
            340                 345                 350

Lys Asn Pro Gln Glu Gly Leu Tyr Asn Glu Leu Gln Lys Asp Lys Met
        355                 360                 365

Ala Glu Ala Tyr Ser Glu Ile Gly Met Lys Gly Glu Arg Arg Arg Gly
    370                 375                 380

Lys Gly His Asp Gly Leu Tyr Gln Gly Leu Ser Thr Ala Thr Lys Asp
385                 390                 395                 400

Thr Tyr Asp Ala Leu His Met Gln Ala Leu Pro Pro Arg
                405                 410


<210> SEQ ID NO 11
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Gly Gly Gly Ser Ser Gly Gly Gly Ser Gly
1               5                   10


<210> SEQ ID NO 12
<211> LENGTH: 12
<212> TYPE: PRT
<213> ORGANISM: Artificial Sequence
```

-continued

```
<220> FEATURE:
<221> NAME/KEY: source
<223> OTHER INFORMATION: /note="Description of Artificial Sequence:
      Synthetic peptide"

<400> SEQUENCE: 12

Glu Ser Lys Tyr Gly Pro Pro Cys Pro Pro Cys Pro
1               5                   10


<210> SEQ ID NO 13
<211> LENGTH: 12
<212> TYPE: PRT
<213> ORGANISM: Homo sapiens

<400> SEQUENCE: 13

Glu Ser Lys Tyr Gly Pro Pro Cys Pro Ser Cys Pro
1               5                   10


<210> SEQ ID NO 14
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Glu Ser Lys Tyr Gly Pro Pro Cys Pro Pro Cys Pro Gly Gly Gly Ser
1               5                   10                  15

Ser Gly Gly Gly Ser Gly
            20


<210> SEQ ID NO 15
<211> LENGTH: 39
<212> TYPE: PRT
<213> ORGANISM: Homo sapiens

<400> SEQUENCE: 15

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro
        35


<210> SEQ ID NO 16
<211> LENGTH: 48
<212> TYPE: PRT
<213> ORGANISM: Homo sapiens

<400> SEQUENCE: 16

Ala Lys Pro Thr Thr Thr Pro Ala Pro Arg Pro Pro Thr Pro Ala Pro
1               5                   10                  15

Thr Ile Ala Ser Gln Pro Leu Ser Leu Arg Pro Glu Ala Cys Arg Pro
            20                  25                  30

Ala Ala Gly Gly Ala Val His Thr Arg Gly Leu Asp Phe Ala Cys Asp
        35                  40                  45


<210> SEQ ID NO 17
<211> LENGTH: 45
<212> TYPE: PRT
<213> ORGANISM: Homo sapiens
```

<400> SEQUENCE: 17

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 18
<211> LENGTH: 129
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 18

Glu Ser Lys Tyr Gly Pro Pro Cys Pro Pro Cys Pro Gly Gly Gly Ser
1               5                   10                  15

Ser Gly Gly Gly Ser Gly Gly Gln Pro Arg Glu Pro Gln Val Tyr Thr
            20                  25                  30

Leu Pro Pro Ser Gln Glu Glu Met Thr Lys Asn Gln Val Ser Leu Thr
        35                  40                  45

Cys Leu Val Lys Gly Phe Tyr Pro Ser Asp Ile Ala Val Glu Trp Glu
    50                  55                  60

Ser Asn Gly Gln Pro Glu Asn Asn Tyr Lys Thr Thr Pro Pro Val Leu
65                  70                  75                  80

Asp Ser Asp Gly Ser Phe Phe Leu Tyr Ser Arg Leu Thr Val Asp Lys
                85                  90                  95

Ser Arg Trp Gln Glu Gly Asn Val Phe Ser Cys Ser Val Met His Glu
            100                 105                 110

Ala Leu His Asn His Tyr Thr Gln Lys Ser Leu Ser Leu Ser Leu Gly
        115                 120                 125

Lys

<210> SEQ ID NO 19
<211> LENGTH: 229
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 19

Glu Ser Lys Tyr Gly Pro Pro Cys Pro Ser Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Gln Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

-continued

```
Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225


<210> SEQ ID NO 20
<211> LENGTH: 229
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Gln Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
```

```
    210                 215                 220

Leu Ser Leu Gly Lys
225


<210> SEQ ID NO 21
<211> LENGTH: 107
<212> TYPE: PRT
<213> ORGANISM: Homo sapiens

<400> SEQUENCE: 21

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105


<210> SEQ ID NO 22
<211> LENGTH: 21
<212> TYPE: PRT
<213> ORGANISM: Homo sapiens

<400> SEQUENCE: 22

Leu Cys Tyr Leu Leu Asp Gly Ile Leu Phe Ile Tyr Gly Val Ile Leu
1               5                   10                  15

Thr Ala Leu Phe Leu
            20


<210> SEQ ID NO 23
<211> LENGTH: 27
<212> TYPE: PRT
<213> ORGANISM: Homo sapiens

<400> SEQUENCE: 23

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25


<210> SEQ ID NO 24
<211> LENGTH: 28
<212> TYPE: PRT
<213> ORGANISM: Homo sapiens

<400> SEQUENCE: 24

Met Phe Trp Val Leu Val Val Val Gly Gly Val Leu Ala Cys Tyr Ser
1               5                   10                  15

Leu Leu Val Thr Val Ala Phe Ile Ile Phe Trp Val
            20                  25


<210> SEQ ID NO 25
<211> LENGTH: 22
```

<212> TYPE: PRT
<213> ORGANISM: Homo sapiens

<400> SEQUENCE: 25

Met Ala Leu Ile Val Leu Gly Gly Val Ala Gly Leu Leu Leu Phe Ile
1               5                   10                  15

Gly Leu Gly Ile Phe Phe
            20

<210> SEQ ID NO 26
<211> LENGTH: 21
<212> TYPE: PRT
<213> ORGANISM: Homo sapiens

<400> SEQUENCE: 26

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 27
<211> LENGTH: 23
<212> TYPE: PRT
<213> ORGANISM: Homo sapiens

<400> SEQUENCE: 27

Ile Tyr Ile Trp Ala Pro Leu Ala Gly Thr Cys Gly Val Leu Leu Leu
1               5                   10                  15

Ser Leu Val Ile Thr Leu Tyr
            20

<210> SEQ ID NO 28
<211> LENGTH: 24
<212> TYPE: PRT
<213> ORGANISM: Homo sapiens

<400> SEQUENCE: 28

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 29
<211> LENGTH: 27
<212> TYPE: PRT
<213> ORGANISM: Homo sapiens

<400> SEQUENCE: 29

Ile Ile Ser Phe Phe Leu Ala Leu Thr Ser Thr Ala Leu Leu Phe Leu
1               5                   10                  15

Leu Phe Phe Leu Thr Leu Arg Phe Ser Val Val
            20                  25

<210> SEQ ID NO 30
<211> LENGTH: 112
<212> TYPE: PRT
<213> ORGANISM: Homo sapiens

<400> SEQUENCE: 30

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr

```
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110


<210> SEQ ID NO 31
<211> LENGTH: 41
<212> TYPE: PRT
<213> ORGANISM: Homo sapiens

<400> SEQUENCE: 31

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40


<210> SEQ ID NO 32
<211> LENGTH: 41
<212> TYPE: PRT
<213> ORGANISM: Homo sapiens

<400> SEQUENCE: 32

Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40


<210> SEQ ID NO 33
<211> LENGTH: 42
<212> TYPE: PRT
<213> ORGANISM: Homo sapiens

<400> SEQUENCE: 33

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40


<210> SEQ ID NO 34
<211> LENGTH: 42
<212> TYPE: PRT
<213> ORGANISM: Homo sapiens

<400> SEQUENCE: 34

Ala Leu Tyr Leu Leu Arg Arg Asp Gln Arg Leu Pro Pro Asp Ala His
1               5                   10                  15
```

-continued

```
Lys Pro Pro Gly Gly Gly Ser Phe Arg Thr Pro Ile Gln Glu Glu Gln
            20                  25                  30

Ala Asp Ala His Ser Thr Leu Ala Lys Ile
        35                  40
```

TREATMENT OF CNS LYMPHOMA AND SYSTEMIC LYMPHOMA WITH INTRACEREBROVENTRICULARLY ADMINISTERED CD19 CAR

CLAIM OF PRIORITY

This application is a National Stage application under 35 U.S.C. § 371 of International Application No. PCT/US2018/059668, filed on Nov. 7, 2018, which claims the benefit of U.S. Provisional Application No. 62/582,891, filed on Nov. 7, 2017. The entire contents of the foregoing are incorporated herein by reference.

SEQUENCE LISTING

This application contains a Sequence Listing that has been submitted electronically as an ASCII text file named "40056-0038US1_SL_ST24.txt". The ASCII text file, created on Jul. 7, 2026, is 49,879 bytes in size. The mateiral in the ASCII text file is hereby incorporated by reference in its entirety.

BACKGROUND

Tumor-specific T cell based immunotherapies, including those that employ engineered T cells and ex vivo expanded or selected T cells, have been investigated for anti-tumor treatment. In some cases, the T cells used in such therapies do not remain active in vivo for a long enough period. In some cases, the tumor-specificity of the T cells is relatively low. In some cases, the engineered T cells have insufficient access to the tumor. Therefore, there is a need in the art for tumor-specific cancer therapies with more effective anti-tumor function.

T cells that are genetically engineered with chimeric antigen receptors (CARs) targeting CD19 (CD19 CAR T cells) have broad application for adoptive therapy of B cell lineage malignancies and have shown tremendous potential in treatment of systemic lymphoma (Wang et al. 2016 *Blood* 127:2980). In CD19 CAR T cell trials, the CAR T cell are administered intravenously. CD19 CAR T cell trafficking in cerebrospinal fluid (CSF) has been reported but most if not all protocols exclude patients with active CNS involvement.

SUMMARY

Described herein are methods for treating B cell lymphoma or B cell leukemia of the central nervous system as well as peripheral B cell lymphoma or B cell leukemia by administering compositions comprising CD19 CAR T cells to the cerebrospinal fluid ("CSF") of a patient. Administration to the CNS can be accomplished, for example, by administration to the ventricular system or the central cavity of the spinal column. Administration to the CNS, as the term is used herein, is distinct from both intratumoral administration (injection or infusion into the tumor itself) and administration to a cavity created by resection of a tumor. In some cases, administration is to the ventricular system or the central cavity of the spinal column and not intratumoral and/or intracavity. However, the CNS administration methods described herein can be combined with intraturmoral and/or post-resection, intracavity administration. Surprisingly, the CAR T cells injected into the CSF are effective against peripheral lymphoma and, in some cases, are more effective against peripheral lymphoma than CAR T cells administered intravenously.

The CNS administration described herein permits, but does not require, infusion of relatively large volumes of the composition comprising T cells, for example 1 ml-2 ml or more in a single infusion. Thus, several million T cells can be administered in a single infusion.

A method of treating a patient diagnosed with a malignancy of the central nervous system, e.g., a B cell lymphoma or B cell leukemia, is thus disclosed, which comprises infusing a composition comprising an effective amount of T cells into an anatomical compartment of a patient diagnosed with a malignancy of the central nervous system, the anatomical compartment containing cerebrospinal fluid ("CSF"). The method includes infusion of a composition into a ventricular system or a portion of a central canal of a spinal cord, for example. In one embodiment of the disclosed method, the malignancy of the central nervous system includes a primary tumor or a metastasized tumor found somewhere in the central nervous system, including a portion of the brain, spinal column, or the like. Preferably the anatomical compartment contains a contiguous volume of at least about 50, 100, or 150 mL of cerebrospinal fluid.

The manipulated T cells infused in the methods described herein target CD19. The malignancies treated can be primary tumors or secondary tumors arising from cancers originating elsewhere in the body. Because administration to the cerebrospinal fluid allows the T cells access to regions beyond the local site of injection, the methods described herein can be used to attack and reduce the size of tumors remote from the site of injection but within the CNS.

Described herein is a method of treating a patient diagnosed with a CNS lymphoma or leukemia and/or peripheral lymphoma or leukemia, e.g., a B cell lymphoma or a B cell leukemia, comprising introducing into the cerebrospinal fluid (CSF) of the patient a composition comprising an effective amount of T cells, e.g., T cells targeted to CD19.

In various embodiments: the T cells are autologous or allogenic T cells; the T cells have been manipulated ex vivo by one or more of: expansion, fractionation or transfection with a recombinant nucleic acid molecule; the T cells comprise cells that have been transfected with a recombinant nucleic acid molecule encoding a polypeptide that binds to a CD19; the polypeptide is a chimeric antigen receptor; the composition is administered intraventricularly; the composition is administered to the central canal of the spinal cord; the administration is to the left ventrical or the right ventrical; the composition comprises at least $1\times10^6$ cells; the composition comprising T cells is administered at least two times; the administrations differ in the total number of T cells administered; the administrations escalate in dose; the administrations de-escalate in dose; the T cells comprise CAR T cells targeting CD19; the T cells comprise autologous tumor infiltrating lymphocytes targeting CD19; the T cells comprise TCR-engineered T cells targeting CD19; the malignancy is a diffuse, infiltrating tumor; the malignancy is a primary brain tumor; one or more tumor foci decrease in size by at least 25%; the malignancy arose from a primary cancer; the method is performed after tumor resection; the method further comprises intratumoral administration of a composition comprising T cells; the malignancy is secondary brain tumor; the method further comprises intratumoral administration of a composition comprising therapeutic T cells expressing a chimeric antigen receptor that binds to CD19; T cells comprise both CD4+ cells and CD8+ cells; the T cells have undergone ex vivo expansion; the T cells comprise at least 10%, 20%, 30% or 40% $T_{CM}$ cells; the T cells comprise at least 10%, 20%, 30% or 40% $T_{N/MEM}$ cells; at least 40%, 50%, 60%, 70% or more of the cells infused are CD4+; at least at least 40%, 50%, 60%, 70% or more of the cells infused express a cell surface receptor that targets CD19; and the dose of cells is based on the number of infused cells that express a cell surface receptor that targets CD19.

In some embodiments the T cells comprise CAR T cells that target CD19 and the cells comprise a nucleic acid molecule encoding a chimeric antigen receptor comprising: scFV targeted to CD19 or a variant thereof having 1-10 (e.g., no more than 5 or no more than 2) amino acid modifications; a transmembrane domain selected from: a CD4 transmembrane domain or variant thereof having 1-10 (e.g., no more than 5 or no more than 2) amino acid modifications, a CD8 transmembrane domain or variant thereof having 1-10 (e.g., no more than 5 or no more than 2) amino acid modifications, a CD28 transmembrane domain or a variant thereof having 1-10 (e.g., no more than 5 or no more than 2) amino acid modifications, and a CD3ζ transmembrane domain or a variant thereof having 1-10 (e.g., no more than 5 or no more than 2) amino acid modifications; at least one costimulatory domain; and CD3 ζ signaling domain of a variant thereof having 1-10 (e.g., no more than 5 or no more than 2) amino acid modifications. In some embodiments: the costimulatory domain is selected from the group consisting of: a CD28 costimulatory domain or a variant thereof having 1-10 (e.g., no more than 5 or no more than 2) amino acid modifications, a 4IBB costimulatory domain or a variant thereof having 1-10 (e.g., no more than 5 or no more than 2) amino acid modifications and an OX40 costimulatory domain or a variant thereof having 1-10 (e.g., no more than 5 or no more than 2) amino acid modifications; the scFv targeted to CD19 comprises the amino acid sequence of SEQ ID NO:3 or SEQ ID NO:3 with 1 to 5 amino acid modifications; the chimeric antigen receptor comprises two different costimulatory domains selected from the group consisting of: a CD28 costimulatory domain or a variant thereof having 1-10 (e.g., no more than 5 or no more than 2) amino acid modifications, a 4IBB costimulatory domain or a variant thereof having 1-10 (e.g., no more than 5 or no more than 2) amino acid modifications and an OX40 costimulatory domain or a variant thereof having 1-10 (e.g., no more than 5 or no more than 2) amino acid modifications; the chimeric antigen receptor comprises two different costimulatory domains selected from the group consisting of: a CD28 costimulatory domain or a variant thereof having 1-2 amino acid modifications, a 4IBB costimulatory domain or a variant thereof having 1-2 amino acid modifications and an OX40 costimulatory domain or a variant thereof having 1-2 amino acid modifications; the chimeric antigen receptor comprises: CD19 scFv or a variant thereof having 1-2 amino acid modifications; a transmembrane domain selected from: a CD4 transmembrane domain or variant thereof having 1-2 amino acid modifications, a CD8 transmembrane domain or variant thereof having 1-2 amino acid modifications, a CD28 transmembrane domain or a variant thereof having 1-2 amino acid modifications, and a CD3 transmembrane domain or a variant thereof having 1-2 amino acid modifications; a costimulatory domain; and CD3 signaling domain of a variant thereof having 1-2 amino acid modifications; the CAR comprises a spacer region located between the CD19 scFv or variant thereof and the transmembrane domain; the spacer region comprises an amino acid sequence selected from the group consisting of SEQ ID NO: 11-21; the chimeric antigen receptor comprises an amino acid sequence selected from the group consisting of any of SEQ ID NOs: 10, 1, 2, 4 and 5 or any of SEQ ID NOs: 10, 1, 2, 4 and 5 having no more than 5 (e.g., 4, 3, 2, or 1) single amino acid substitutions.

Also described herein is a method of treating a patient diagnosed with a malignancy of the central nervous system comprising infusing a composition comprising an effective amount of T cells into an anatomical compartment of a patient diagnosed with a malignancy of the central nervous system, the anatomical compartment containing cerebrospinal fluid (CSF). In various embodiments: the anatomical compartment comprises a portion of a ventricular system; the anatomical compartment comprises a portion of a central canal of a spinal cord; the malignancy of the central nervous system includes a brain tumor; the malignancy of the central nervous system includes a metastasized tumor; the anatomical compartment contains a contiguous volume of at least about 50 mL of cerebrospinal fluid; the anatomical compartment contains a contiguous volume of at least about 100 mL of cerebrospinal fluid; and the anatomical compartment contains a contiguous volume of at least about 150 mL of cerebrospinal fluid.

In some embodiments, the malignancy treated according to the disclosed methods comprises a tumor. In some embodiments, treatment results in at least a 50% reduction in tumor volume, at least a 60% reduction in tumor volume, at least a 70% reduction in tumor volume, at least an 80% reduction in tumor volume, or at least a 90% reduction in tumor volume. In some embodiments, the treatment results in elimination of the malignancy.

In some embodiments, the patient does not experience any grade 3 or higher toxicity.

In some embodiments, the patient was administered a regimen of steroids prior to treatment with the composition comprising an effective amount of T cells, and in some embodiments the regimen of steroids is reduced to a lower dose following the treatment.

In some embodiments, the patient has an increased life expectancy compared to a patient receiving standard of care treatment, including radiation therapy, small molecule drug therapy, antibody therapeutics, or a combination thereof. And in some embodiments, in which the patient receiving standard of care ("SOC") treatment can expect to survive about 15 months from initial diagnosis (overall survival or OS), the patient receiving the disclosed treatment can expect an OS of 15, 20, 25, 26, 27, 28, 29, 30, 31, 32, 33, 34, 35, 36 months or more. In some embodiments, the patient receiving the claimed treatment can expect an OS of 42, 48, 54, 60, 66, 72, 78, 84, 90 months or more.

In some embodiments, the composition comprises at least $2\times10^6$ T cells or $2\times10^6$ T cells expressing a cell surface receptor targeting a tumor antigen, while in some embodiments, the composition comprises at least $1\times10^6$ T cells or $2\times10^6$ T cells expressing a cell surface receptor targeting a tumor antigen. In some embodiments, the composition comprises at least $5\times10^6$ T cells or $5\times10^6$ T cells expressing a cell surface receptor targeting a tumor antigen, while in some embodiments, the composition comprises at least $5v\times10^6$ T cells or $10\times10^6$ T cells expressing a cell surface receptor targeting a tumor antigen. In some embodiments, the disclosed methods comprised repeated administrations of the compositions, for instance repeating administration of the composition at least five times, repeating administration of the composition at least ten times, or repeating administration until the patient receives a total dose of at least $90\times10^6$ T cells or T cells expressing a cell surface receptor targeting a tumor antigen. In some embodiments, the administration is repeated once a week or once every two weeks. In some embodiments, the repeated administrations are continued over the course of 15 weeks.

Also disclosed herein are methods of sustaining for at least about five days an increased number of T cells, compared to a baseline number, observed in a cerebrospinal fluid (CSF) of a patient diagnosed with a malignancy of a central nervous system, comprising infusing an effective amount of T cells into a CSF of a patient diagnosed with a malignancy of a central nervous system, in which an increased number of T cells observed, compared to a baseline number observed prior to the infusion step, is sustained for at least about five days.

In some embodiments, an effective amount of T cells (or T cells expressing a cell surface receptor that targets the tumor antigen) ranges from about $1\times10^6$ cells to about $100\times10^6$ cells, and in some embodiments, an effective amount of T cells ranges from about $2\times10^6$ cells to about $50\times10^6$ cells.

In some embodiments, the increased number of T cells observed is sustained for at least about six days, or the number of T cells observed does not return to the baseline number for about seven days.

In some embodiments, the T cells observed include infused T cells (e.g. CAR-expressing T cells), and in some embodiments, the T cells observed include endogenous T cells.

Also disclosed herein are methods of increasing a number of T cells in the cerebrospinal fluid (CSF) of a patient comprising, administering a composition comprising an effective amount of T cells into the CSF of a patient with a malignancy of the central nervous system, wherein the number of T cells detectable in the CSF is increased compared to pre-administration levels.

TIL are tumor infiltrating lymphocytes that can be isolated from a patient or a donor, expand ex vivo and re-infused into the patient in need thereof.

CAR T cells express chimeric T cell receptors that comprise an extracellular domain, a transmembrane region and an intracellular signaling domain. The extracellular domain includes a portion that binds the targeted cell and, optionally, a spacer, comprising, for example a portion human Fc domain. The transmembrane portion includes suitable transmembrane domain, for example, a CD4 transmembrane domain, a CD8 transmembrane domain, a CD28 transmembrane domain, a CD3 transmembrane domain or a 4IBB transmembrane domain. The intracellular signaling domain includes the signaling domain from the zeta chain of the human CD3 complex (CD3ζ) and one or more costimulatory domains, e.g., a 4-1BB costimulatory domain. The target cell binding portion of extracellular domain (for example a scFv targeted to CD19) enables the CAR, when expressed on the surface of a T cell, to direct T cell activity to those cells expressing CD19.

A variety of different T cells, for example, patient-specific, autologous T cells, can be engineered to express a TCR or a CAR targeted to CD19. Various T cell subsets can be used. In addition, CAR can be expressed in other immune cells such as NK cells. Where a patient is treated with an immune cell expressing a CAR or TCR the cell can be an autologous or allogenic T cell. In some cases, the cells used are CD4+ and CD8+ central memory T cells ($T_{CM}$), which are CD45RO+CD62L+. This cell population is enriched for CD62L expressing cells and substantially depleted for CD45RA expressing cells, CD14 expressing cells and CD25 expressing cells. The $T_{CM}$ cells can include CD4+ cells and CD8+ cells.

In some cases, the cells used comprise a mixture of naive T cells ($T_N$) and memory T cells ($T_{MEM}$). Memory T cells include central memory T cells ($T_{CM}$) and stem central memory cells ($T_{SCM}$). Thus, the T cell population that is a mixture of naïve T cells, central memory T cells and stem central memory T cells can be referred to as "$T_{N/MEM}$" or "$T_{CM/SCM/N}$" and these two notations are used interchangeably herein. This cell population is enriched for CD62L expressing cells and substantially depleted for CD14 expressing cells and CD25 expressing cells. Thus, a population of cells comprising (e.g., more that 50%, 60%, 70%, 80%, 90% or 95%) CD62L+ T cells can be administered.

The T cells used in the methods described herein can contain a nucleic acid molecule encoding a chimeric antigen receptor (CAR), wherein the chimeric antigen receptor comprises: scFv targeted to CD19 or a variant thereof having 1-10 (e.g., 1 or 2) amino acid modifications; a transmembrane domain selected from: a CD4 transmembrane domain or variant thereof having 1-10 (e.g., 1 or 2) amino acid modifications, a CD8 transmembrane domain or variant thereof having 1-10 (e.g., 1 or 2) amino acid modifications, a CD28 transmembrane domain or a variant thereof having 1-10 (e.g., 1 or 2) amino acid modifications, and a CD3ζ transmembrane domain or a variant thereof having 1-10 (e.g., 1 or 2) amino acid modifications; a costimulatory domain; and CD3 signaling domain of a variant thereof having 1-10 (e.g., 1 or 2) amino acid modifications.

The inclusion of a costimulatory domain, such as the 4-1BB (CD137) or CD28 costimulatory domain in series with CD3ζ in the intracellular region enables the T cell to receive co-stimulatory signals. Thus, in various embodiments, the costimulatory domain is selected from the group consisting of: a CD28 costimulatory domain or a variant thereof having 1-10 (e.g., 1 or 2) amino acid modifications, a 4-IBB costimulatory domain or a variant thereof having 1-10 (e.g., 1 or 2) amino acid modifications and an OX40 costimulatory domain or a variant thereof having 1-10 (e.g., 1 or 2) amino acid modifications. In certain embodiments, a 4IBB costimulatory domain or a variant thereof having 1-10 (e.g., 1 or 2) amino acid modifications is present.

In additional embodiments of the methods, the CAR expressed by the T cells comprises: a variant a scFv targeted to CD19 having 1-10 (e.g., 1 or 2) amino acid modifications compared to SEQ ID NO: 3; two different costimulatory domains selected from the group consisting of: a CD28 costimulatory domain or a variant thereof having 1-10 (e.g., 1 or 2) amino acid modifications, a 4IBB costimulatory domain or a variant thereof having 1-10 (e.g., 1 or 2) amino acid modifications and an OX40 costimulatory domain or a variant thereof having 1-10 (e.g., 1 or 2) amino acid modifications; two different costimulatory domains selected from the group consisting of: a CD28 costimulatory domain or a variant thereof having 1-2 amino acid modifications, a 4IBB costimulatory domain or a variant thereof having 1-2 amino acid modifications and an OX40 costimulatory domain or a variant thereof having 1-2 amino acid modifications; human IL-13 or a variant thereof having 1-2 amino acid modifications; a transmembrane domain selected from: a CD4 transmembrane domain or variant thereof having 1-2 amino acid modifications, a CD8 transmembrane domain or variant thereof having 1-2 amino acid modifications, a CD28 transmembrane domain or a variant thereof having 1-2 amino acid modifications, and a CD3 transmembrane domain or a variant thereof having 1-2 amino acid modifications; a costimulatory domain; and CD3 signaling domain of a variant thereof having 1-2 amino acid modifications; a spacer region located between the IL-13 or variant thereof and the transmembrane domain (e.g., the spacer region comprises an amino acid sequence selected from the group consisting of SEQ ID NO: 11-22); the spacer comprises an IgG hinge region; the spacer region comprises 10-150 amino acids; the 4-1BB signaling domain comprises the amino acid sequence of SEQ ID NO:33; the CD3 signaling domain comprises the amino acid sequence of SEQ ID NO:30; and a linker of 3 to 15 amino acids that is located between the costimulatory domain and the CD3 signaling domain or variant thereof. In certain embodiments where there are two costimulatory domains, one is a 4-IBB costimulatory domain and the other a costimulatory domain selected from: CD28 and CD28gg In some embodiments of the methods described herein the T cells harbor a nucleic acid molecule that expresses a polypeptide comprising an amino acid sequence selected from SEQ ID NOs: 10, 1, 2, 4 and 5; the chimeric antigen receptor comprises a CD19 scFv region comprising the amino acid of SEQ ID NO:3 and a CD3 signaling domain comprising the amino acid sequence of SEQ ID NO:30; and the chimeric antigen receptor comprises the amino acid sequence of any of SEQ ID NOs: 10, 1, 2, 4 and 5.

Also disclosed are methods comprising intraventricular administration of a population of human T cells transduced by a vector comprising an expression cassette encoding a chimeric antigen receptor, wherein chimeric antigen receptor comprises: human IL-13 or a variant thereof having 1-10 amino acid modifications; a transmembrane domain selected from: a CD4 transmembrane domain or variant thereof having 1-10 amino acid modifications, a CD8 transmembrane domain or variant thereof having 1-10 amino acid modifications, a CD28 transmembrane domain or a variant thereof having 1-10 amino acid modifications, and a CD3ζ transmembrane domain or a variant thereof having 1-10 amino acid modifications; a costimulatory domain; and CD3ζ signaling domain of a variant thereof having 1-10 amino acid modifications. In various embodiments: the population of human T cells comprise a vector expressing a chimeric antigen receptor comprising an amino acid sequence selected from SEQ ID NOs: 10, 1, 2, 4 and 5; the population of human T cells are comprises of central memory T cells ($T_{CM}$ cells) (e.g., at least 20%, 30%, 40%, 50% 60%, 70%, 80% of the cells are $T_{CM}$ cells; at least 10%, 15%, 20%, 25%, 30% or 35% of the T cells or the $T_{CM}$ cells are CD4+ and at least 10%, 15%, 20%, 25%, 30% or 35% of the T cells or the $T_{CM}$ cells are CD8+ cells).

The population of human T cells comprises $T_{N/MEM}$ ($T_{CM}$ cells) (e.g., at least 20%, 30%, 40%, 50% 60%, 70%, 80% of the cells are $T_{N/MEM}$ cells; at least 10%, 15%, 20%, 25%, 30% or 35% of the T cells or the $T_{N/MEM}$ cells are CD4+ and at least 10%, 15%, 20%, 25%, 30% or 35% of the T cells or the $T_{N/MEM}$ cells are CD8+ cells).

Also described is a method of treating cancer in a patient comprising CNS administration of a population of autologous or allogeneic human T cells (e.g., autologous or allogeneic T cells comprising $T_{CM}$ cells, e.g., at least 20%, 30%, 40%, 50% 60%, 70%, 80% of the cells are $T_{CM}$ or $T_{N/MEM}$ cells; at least 15%, 20%, 25%, 30%, 35% of the $T_{CM}$ or $T_{N/MEM}$ cells are CD4+ and at least 15%, 20%, 25%, 30%, 35% of the $T_{CM}$ or $T_{N/MEM}$ cells are CD8+ cells) transduced by a vector comprising an expression cassette encoding a chimeric antigen receptor, wherein chimeric antigen receptor comprises an amino acid sequence selected from SEQ ID NOs: 10, 1, 2, 4 and 5; comprises an amino acid sequence that is identical to an amino acid sequence selected from SEQ ID NO: 10, 1, 2, 4 and 5 except for the presence of no more than 5 amino acid (e.g., 4, 3, 2, 1) substitutions, deletions or insertions; comprises an amino acid sequence that is identical to an amino acid sequence selected from SEQ ID NOs: 10, 1, 2, 4 and 5 except for the presence of no more than 5 amino acid substitutions; and comprises an amino acid sequence that is identical to an amino acid sequence selected from SEQ ID NOs: 10, 1, 2, 4 and 5 except for the presence of no more than 2 amino acid substitutions. In various embodiments: the population of human T cells comprise central memory T cells; the cancer is B cell leukemia or B cell lymphoma; and the transduced human T cells where prepared by a method comprising obtaining T cells from the patient, treating the T cells to isolate central memory T cells, and transducing at least a portion of the central memory cells to with a viral vector comprising an expression cassette encoding a chimeric antigen receptor, wherein chimeric antigen receptor comprises an amino acid sequence selected from SEQ ID NOs: 10, 1, 2, 4 and 5; comprises an amino acid sequence that is identical to an amino acid sequence selected from SEQ ID NO: 10, 1, 2, 4 and 5 except for the presence of no more than 5 amino acid (e.g., 4, 3, 2, 1) substitutions, deletions or insertions; comprises an amino acid sequence that is identical to an amino acid sequence selected from SEQ ID NOs: 10, 1, 2, 4 and 5 except for the presence of no more than 5 amino acid substitutions; and comprises an amino acid sequence that is identical to an amino acid sequence selected from SEQ ID NOs: 10, 1, 2, 4 and 5 except for the presence of no more than 2 amino acid substitutions.

Also described are method is which the T cells administered to the patient harbor a nucleic acid molecule encoding an polypeptide comprising an amino acid sequence that is at least 95% identical to an amino acid sequence selected from and SEQ ID NOs: 10, 1, 2, 4 and 5; a nucleic acid molecule encoding an polypeptide comprising an amino acid sequence that is identical to an amino acid sequence selected from SEQ ID NO: 10, 1, 2, 4 and 5 except for the presence of no more than 5 amino acid (e.g., 4, 3, 2, 1) substitutions, deletions or insertions; a nucleic acid molecule encoding an polypeptide comprising an amino acid sequence that is identical to an amino acid sequence selected from SEQ ID NOs: 10, 1, 2, 4 and 5 except for the presence of no more than 5 amino acid substitutions; and a nucleic acid molecule encoding an polypeptide comprising an amino acid sequence that is identical to an amino acid sequence selected from SEQ ID NOs: 10, 1, 2, 4 and 5 except for the presence of no more than 2 amino acid substitutions.

In some cases, the CD19 CAR comprises the amino acid sequence of SEQ ID NO: 10 and an amino acid sequence of an ScFv that binds human CD19.

In some cases: the T cells expressing a CD19 targeted CAR are T cells have been cultured in a culture medium having 60 mg/dL glucose and 2.8 mEq/L potassium; the T cells expressing a CD19 targeted CAR are T cells have been activated by exposure to CD19 prior to administration; the T cells have been activated by exposure to cells expressing CD19 prior to administration; and the T cells cells have been cultured in a culture medium having 60 mg/dL glucose and 2.8 mEq/L potassium and have been activated by exposure to CD19 prior to administration or by exposure to cells expressing CD19 prior to administration.

In some cases, the CD19 CAR comprises the amino acid sequence of any of SEQ ID Nos: 10, 10, 1, 2, 4 and 5 except for the presence of no more than 2 single amino acid substitutions.

The CAR described herein can include a spacer region located between the targeting domain and the transmembrane domain. A variety of different spacers can be used.

Some of them include at least portion of a human Fc region, for example a hinge portion of a human Fc region or a CH3 domain or variants thereof. Table 1 below provides various spacers that can be used in the CARs described herein.

TABLE 1

Examples of Spacers

| Name | Length | Sequence |
| --- | --- | --- |
| a3 | 3 aa | AAA |
| linker | 10 aa | GGGSSGGGSG (SEQ ID NO: 11) |
| IgG4 hinge (S→P) (S228P) | 12 aa | ESKYGPPCPPCP (SEQ ID NO: 12) |
| IgG4 hinge | 12 aa | ESKYGPPCPSCP (SEQ ID NO: 13) |
| IgG4 hinge + linker | 22 aa | ESKYGPPCPPCPGGGSSGGGSG (SEQ ID NO: 14) |
| CD28 hinge | 39 aa | IEVMYPPPYLDNEKSNGTIIHVKGKHLCPSP LFPGPSKP (SEQ ID NO: 15) |
| CD8 hinge-48 aa | 48 aa | AKPTTTPAPRPPTPAPTIASQPLSLRPEACR PAAGGAVHTRGLDFACD (SEQ ID NO: 16) |
| CD8 hinge-45 aa | 45 aa | TTTPAPRPPTPAPTIASQPLSLRPEACRPAA GGAVHTRGLDFACD (SEQ ID NO: 17) |
| IgG4 (HL-CH3) | 129 aa | ESKYGPPCPPCPGGGSSGGGSGGQPREPQVY TLPPSQEEMTKNQVSLTCLVKGFYPSDIAVE WESNGQPENNYKTTPPVLDSDGSFFLYSRLT VDKSRWQEGNVFSCSVMHEALHNHYTQKSLS LSLGK (SEQ ID NO: 18) |
| IgG4 (L235E, N297Q) | 229 aa | ESKYGPPCPSCPAPEFEGGPSVFLFPPKPKD TLMISRTPEVTCVVVDVSQEDPEVQFNWYVD GVEVHNAKTKPREENFNSTYRVVSVLTVLHQ DWLNGKEYKCKVSNKGLPSSIEKTISKAKGQ PREPQVYTLPPSQEEMTKNQVSLTCLVKGFY PSDIAVEWESNGQPENNYKTTPPVLDSDGSF FLYSRLTVDKSRWQEGNVFSCSVMHEALHNH YTQKSLSLSLGK (SEQ ID NO: 19) |
| IgG4 (S228P, L235E, N297Q) | 229 aa | ESKYGPPCPPCPAPEFEGGPSVFLFPPKPKD TLMISRTPEVTCVVVDVSQEDPEVQFNWYVD GVEVHNAKTKPREENFNSTYRVVSVLTVLHQ DWLNGKEYKCKVSNKGLPSSIEKTISKAKGQ PREPQVYTLPPSQEEMTKNQVSLTCLVKGFY PSDIAVEWESNGQPENNYKTTPPVLDSDGSF FLYSRLTVDKSRWQEGNVFSCSVMHEALHNH YTQKSLSLSLGK (SEQ ID NO: 20) |

Some spacer regions include all or part of an immunoglobulin (e.g., IgG1, IgG2, IgG3, IgG4) hinge region, i.e., the sequence that falls between the CH1 and CH2 domains of an immunoglobulin, e.g., an IgG4 Fc hinge or a CD8 hinge. Some spacer regions include an immunoglobulin CH3 domain or both a CH3 domain and a CH2 domain. The immunoglobulin derived sequence can include one or more amino acid modifications, for example, 1, 2, 3, 4 or 5 substitutions, e.g., substitutions that reduce off-target binding.

An "amino acid modification" refers to an amino acid substitution, insertion, and/or deletion in a protein or peptide sequence. An "amino acid substitution" or "substitution" refers to replacement of an amino acid at a particular position in a parent peptide or protein sequence with another amino acid. A substitution can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. The following are examples of various groupings of amino acids: 1) Amino acids with nonpolar R groups: Alanine, Valine, Leucine, Isoleucine, Proline, Phenylalanine, Tryptophan, Methionine; 2) Amino acids with uncharged polar R groups: Glycine, Serine, Threonine, Cysteine, Tyrosine, Asparagine, Glutamine; 3) Amino acids with charged polar R groups (negatively charged at pH 6.0): Aspartic acid, Glutamic acid; 4) Basic amino acids (positively charged at pH 6.0): Lysine, Arginine, Histidine (at pH 6.0). Another grouping may be those amino acids with phenyl groups: Phenylalanine, Tryptophan, and Tyrosine.

A variety of transmembrane domains can be used in CAR expressed by the cells used in the methods described herein. Table 2 includes examples of suitable transmembrane domains. Where a spacer region is present, the transmembrane domain is located carboxy terminal to the spacer region.

TABLE 2

Examples of Transmembrane Domains

| Name | Accession | Length | Sequence |
| --- | --- | --- | --- |
| CD3z | J04132.1 | 21 aa | LCYLLDGILFIYGVILTALFL (SEQ ID NO: 22) |
| CD28 | NM_006139 | 27 aa | FWVLVVVGGVLACYSLLVTVA FIIFWV (SEQ ID NO: 23) |
| CD28(M) | NM_006139 | 28 aa | MFWVLVVVGGVLACYSLLVTV AFIIFWV (SEQ ID NO: 24) |
| CD4 | M35160 | 22 aa | MALIVLGGVAGLLLFIGLGIF F (SEQ ID NO: 25) |
| CD8tm | NM_001768 | 21 aa | IYIWAPLAGTCGVLLLSLVIT (SEQ ID NO: 26) |
| CD8tm2 | NM_001768 | 23 aa | IYIWAPLAGTCGVLLLSLVIT LY (SEQ ID NO: 27) |
| CD8tm3 | NM_001768 | 24 aa | IYIWAPLAGTCGVLLLSLVIT LYC (SEQ ID NO: 28) |
| 41BB | NM_001561 | 27 aa | IISFFLALTSTALLFLLFFLT LRFSVV (SEQ ID NO: 29) |

Many of the CAR expressed by the cells used in the methods described herein include one or more (e.g., two) costimulatory domains. The costimulatory domain(s) are located between the transmembrane domain and the CD3ζ signaling domain. Table 3 includes examples of suitable costimulatory domains together with the sequence of the CD3ζ signaling domain.

TABLE 3

| CD3ζ Signaling Domain and Examples of Costimulatory Domains | | | |
|---|---|---|---|
| Name | Accession | Length | Sequence |
| CD3ζ | J04132.1 | 113 aa | RVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR (SEQ ID NO: 30) |
| CD28 | NM_006139 | 42 aa | RSKRSRLLHSDYMNMTPRRPGPTRKHYQPYAPPRDFAAYRS (SEQ ID NO: 31) |
| CD28gg* | NM_006139 | 42 aa | RSKRSRGGHSDYMNMTPRRPGPTRKHYQPYAPPRDFAAYRS (SEQ ID NO: 32) |
| 41BB | NM_001561 | 42 aa | KRGRKKLLYIFKQPFMRPVQTTQEEDGCSCRFPEEEEGGCEL (SEQ ID NO: 33) |
| OX40 | | 42 aa | ALYLLRRDQRLPPDAHKPPGGGSFRTPIQEEQADAHSTLAKI (SEQ ID NO: 34) |

DESCRIPTION OF DRAWINGS

FIGS. 1A-1B: Amino acid sequence of a CD19 CAR with a Signal Sequence. SEQ ID NO: 1 is the sequence of the CD19 CAR (including the signal sequence; GMCSFRa signal peptide (SEQ ID NO: 9)) used in the studies described herein. The various domains are labelled and indicated by underlining or lack of underling with the exception of the GGG linker which is indicated by a double underline. (A). Example of selected surface marker expression profiles for PBMC, $T_{CM}$, and $T_{SCM/CM/N}$ (B).

FIGS. 19A-19C: Amino Acid Sequence of a Marker and a CD19 scFv. (A) SEQ ID NO:6 is the sequence of a marker that can follow the sequence of a CD19 CAR. It includes a T2A skip sequence (SEQ ID NO: 7) and a modified EGFR that lacks signaling activity (SEQ ID NO:8) as well as a GMCSFRa signal peptide (SEQ ID NO: 9) and can follow an CAR sequence to provide a useful marker that is expressed separately from the mature CAR as a surface maker and by the same cell. (B) Sequence of scFv (SEQ ID NO: 3) used in the CD19 CAR described herein. (C) Sequence of the CD19 CAR used in the studies described herein without the CD19 scFv sequence (SEQ ID NO:10).

Figure 2:
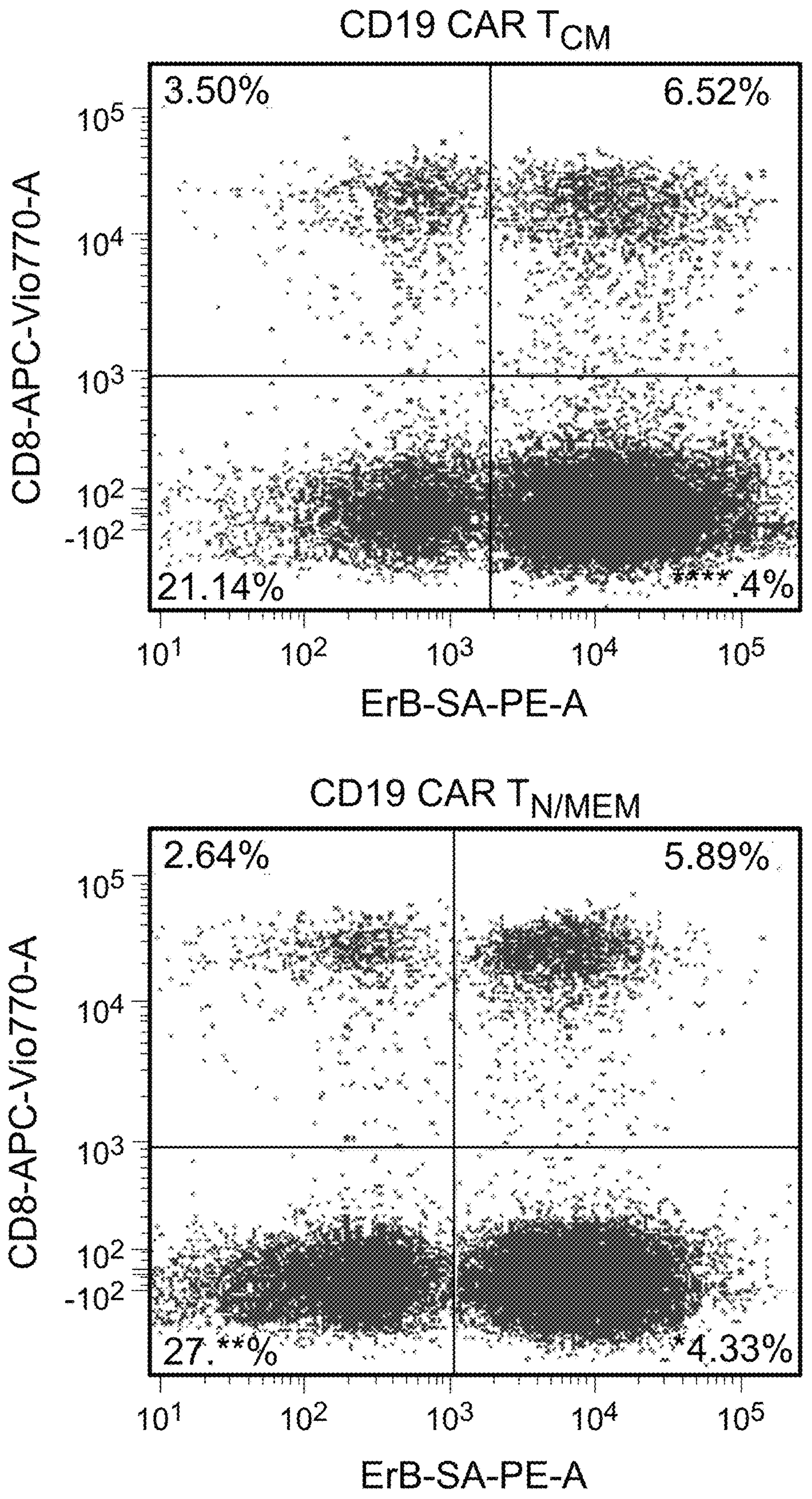
FIG. 2: Phenotype of $T_{CM}$ and $T_{N/MEM}$-derived CD19CAR T cells. $T_{CM}$ (CD62L+CD45RO+) and $T_{N/MEM}$ (CD62L+) cells were isolated from healthy donor PBMCs and transduced to express a second generation CD19 specific chimeric antigen receptor (CAR) with a truncated EGFR (EGFRt). CAR T cells were expanded in the presence of IL-2 50 U/mL and IL-15 0.5 ng/mL for 14 days. CAR expression was defined by Erbitux-biotin and streptavidin (SA) staining.

This sequence can be joined to any suitable CD19 scFv sequence to create an alternative CD19 CAR.

FIG. 20: Amino acid sequence of a CD19 CAR (Mature). SEQ ID NO:2 is the sequence of an alternate mature CD19 CAR (lacking signal sequence). The various domains are labelled and indicated by underlining or lack of underling with the exception of the GGG linker which is indicated by a double underline.

FIG. 21: Amino acid sequence of a CD19 CAR with a Signal Sequence. SEQ ID NO:4 is the sequence of this CD19 CAR (including the signal sequence; GMCSFRa signal peptide (SEQ ID NO: 9) which differs from the CD19 used in the studies described herein in that the IgG4 spacer lacks the S to P mutation (spacer is SEQ ID NO:19 rather than SEQ ID NO:20). The various domains are labelled and indicated by underlining or lack of underling with the exception of the GGG linker which is indicated by a double underline.

FIG. 22: Amino acid sequence of a CD19 CAR (Mature). SEQ ID NO:5 is the sequence of this CD19 CAR (lacking signal sequence) which differs from the CD19 CAR used in the studies described herein in that the IgG4 spacer lacks the S to P mutation (spacer is SEQ ID NO:19 rather than SEQ ID NO:20). The various domains are labelled and indicated by underlining or lack of underling with the exception of the GGG linker which is indicated by a double underline.

DETAILED DESCRIPTION

Described below is the structure, construction and characterization of various CD19 CAR T cells and their use in treating lymphoma of the central nervous system as well a peripheral lymphoma. A chimeric antigen (CAR) is a recombinant biomolecule that contains, at a minimum, an extracellular recognition domain, a transmembrane region, and an intracellular signaling domain. The term “antigen,” therefore, is not limited to molecules that bind antibodies, but to any molecule that can bind specifically to a target. For example, a CAR can include a ligand that specifically binds a cell surface receptor. The extracellular recognition domain (also referred to as the extracellular domain or simply by the recognition element which it contains) comprises a recognition element that specifically binds to a molecule present on the cell surface of a target cell. The transmembrane region anchors the CAR in the membrane. The intracellular signaling domain comprises the signaling domain from the zeta chain of the human CD3 complex and one or more costimulatory signaling domains. CARs can both to bind antigen and transduce T cell activation, independent of MHC restriction. Thus, CARs are “universal” immunoreceptors which can treat a population of patients with antigen-positive tumors irrespective of their HLA genotype. Adoptive immunotherapy using T lymphocytes that express a tumor-specific CAR can be a powerful therapeutic strategy for the treatment of cancer.

In some cases the CAR described herein can be produced using a vector in which the CAR open reading frame is followed by a T2A ribosome skip sequence and a truncated CD19 (CD19t), which lacks the cytoplasmic signaling tail (truncated at amino acid 323). In this arrangement, co-expression of CD19t provides an inert, non-immunogenic surface marker that allows for accurate measurement of gene modified cells, and enables positive selection of gene-modified cells, as well as efficient cell tracking and/or imaging of the therapeutic T cells in vivo following adoptive transfer. Co-expression of CD19t provides a marker for immunological targeting of the transduced cells in vivo using clinically available antibodies and/or immunotoxin reagents to selectively delete the therapeutic cells, and thereby functioning as a suicide switch. In other cases, the CD19 CAR can be expressed with a truncated EGFR. The truncated EGFR provides a marker for immunological targeting of the transduced cells in vivo using clinically available antibodies and/or immunotoxin reagents to selectively delete the therapeutic cells, and thereby functioning as a suicide switch.

The disclosed methods of treatment using CAR T cells can be performed at various doses and across various timeframes. For example, a patient receiving an infusion, administration, or injection of CD19 CAR T cells may receive a single dose comprising between $1\times10^6$ and $15\times10^6$ cells. In other words, a single dose for use in the disclosed methods can comprise $1\times10^6$, $2\times10^6$, $3\times10^6$, $4\times10^6$, $5\times10^6$, $6\times10^6$, $7\times10^6$, $8\times10^6$, $9\times10^6$, $10\times10^6$, $11\times10^6$, $12\times10^6$, $13\times10^6$, $14\times10^6$, or $15\times10^6$ cells. Over the entire course of treatment, a patient may receive a cumulative or total dose of cells between $20\times10^6$ and $150\times10^6$ T cells. For instance, the patient may receive about $20\times10^6$, about $25\times10^6$, about $30\times10^6$, about $35\times10^6$, about $40\times10^6$, about $45\times10^6$, about $50\times10^6$, about $55\times10^6$, about $60\times10^6$, about $65\times10^6$, about $70\times10^6$, about $75\times10^6$, about $80\times10^6$, about $85\times10^6$, about $90\times10^6$, about $95\times10^6$, about $100\times10^6$, about $105\times10^6$, about $110\times10^6$, about $115\times10^6$, about $120\times10^6$, about $125\times10^6$, about $130\times10^6$, about $135\times10^6$, about $140\times10^6$, about $145\times10^6$, or about $150\times10^6$ or more T cells over the course of treatment. In some embodiments, a patient can receive a total dose of at least $90\times10^6$ T cells. In one embodiment, a patient can receive a total dose of $94\times10^6$ T cells.

Furthermore, the doses may be administered according to different regimens and timetables. For example, the disclosed methods can comprise an infusion, administration, or injection once a day, once every two days, once every three days, once every four days, once every five days, once every six days, a week, once every two weeks, once every three weeks, once every four weeks, once a month, once every other month, once every three months, or once every six months. In some embodiments, the disclosed methods can comprise continuous infusion, for instance, from a wearable pump. Similarly, the total time course of treatment may be about 5 weeks, about 10 weeks, about 15 weeks, about 20 weeks, about 25 weeks, about 30 weeks, about 35 weeks, about 40 weeks, about 45 weeks, about 50 weeks, about 55 weeks, about 60 weeks, about 65 weeks, about 70 weeks, about 75 weeks, or more. The patient may receive 1, 2, 3, 4, 5, 6, 7, 8, 9, 10, 11, 12, 13, 14, 15, 16, 17, 18, 19, or 20 or more infusions, administrations, or injections of T cells over the course of treatment according to the disclosed methods. For example, in one embodiment, a patient can receive 11 infusions of T cells over the course of 15 weeks.

Treating cancer, and more specifically lymphoma, according to the disclosed methods can result in numerous therapeutic effects. For instance, treatment with the disclosed CAR T cells can result in an increase in the level of cytokines (e.g., Thl cytokines) and chemokines in the CSF of a patient being treated according to the disclosed methods. Cytokine and/or chemokine expression may increase by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or at least 100%, or cytokine and/or chemokine expression may increase by at least 1-fold, at least 2-fold, at least 3-fold, at least 4-fold, at least 5-fold, at least 6-fold, at least 7-fold, at least 8-fold, at least 9-fold, or at least 10-fold compared to baseline levels, as measured prior to treatment with a composition comprising CAR T cells. This increase in expression may be observed for 1, 2, 3, 4, 5, 6, 7, 8, 9, 10, 11, 12, 13, 14, or 15 or more cytokines or chemokines.

In particular, the expression of at least one of EGF, Eotaxin, FGF, G-CSF, GM-CSF, HGF, IFN-α, IFN-γ, IL-10, IL-12, IL-13, IL-15, IL-17, IL-1Rα, IL-1β, IL-2, IL-2R, IL-4, IL-5, IL-6, IL-7, IL-8, IP-10, MCP-1, MIG, MIP-1α, MIP-1β, RANTES, TNF-α, and VEGF may increase as a result of treatment with CAR T cells as disclosed herein. Furthermore, the increase in cytokine and/or chemokine expression may be local (i.e. the increase is only observable in the CNS and CFS, while serum levels of cytokines and chemokines remain unchanged.

Treatment according to the disclosed methods may also result in an increase in T cells detectable in the CSF. While at least some of the T cells detectable in the CSF following treatment will likely be CAR-expressing T cells, there may also be an increase in endogenous T cells that are recruited to the CSF. Although not wanting to be bound by theory, the increase in endogenous T cells may be a result of the recruitment of Type 1 and Type 2 T helper cells due to the increase in local cytokine levels. Additionally, the detectable T cells can comprise CD3+ T cells, as well as CD14+ CD11b+ HLA-DR+ mature myeloid populations, CD19+ B cells and CD11b+ CD15+ granulocytes, and/or reactive lymphocytes, monocytes, and macrophages.

The increase in the number of T cells in the CSF may be detectable for a specific period of time following treatment according to the disclosed methods. A detectable increase in T cells in the CSF may persist or be sustained for 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 or more days following administration of a composition comprising T cells. For example, an increase in the number of T cells observed in the CSF may not return to baseline levels (i.e. the number of T cells detectable prior to treatment) for about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days. The number of T cells detectable in the CSF may increase by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or at least 100%, or by at least 1-fold, at least 2-fold, at least 3-fold, at least 4-fold, at least 5-fold, at least 6-fold, at least 7-fold, at least 8-fold, at least 9-fold, at least 10-fold, at least 11-fold, at least 12-fold, at least 13-fold, at least 14-fold, or at least 15-fold compared to baseline levels, as measured prior to treatment with a composition comprising CAR T cells.

As used herein, the term "intraventricular" refers to the space inside the ventricular system, specifically the cerebral ventricles. Accordingly, the term "intraventricular" and "intracerebroventricular" may be used interchangeably throughout this disclosure. Accordingly, "intraventricular administration" or "intraventricular injection" refer to delivery of a composition into the ventricals of the brain (i.e. the cerebral ventricles). The cerebral ventricles are a series of interconnected, fluid-filled spaces that lie in the core of the forebrain and brainstem. This system comprises four ventricles: the right and left lateral ventricles (one of which is found in each hemisphere of the brain), the third ventricle, and the fourth ventricle.

The disclosed methods comprise various routes of administering the compositions comprising T cells. For instance, in some embodiments, the disclosed compositions may be delivered or administered intraventricularly. In some embodiments, the disclosed compositions may be delivered or administered into the spinal canal (i.e. intrathecal delivery). In some embodiments, the disclosed compositions may be delivered or administered into the epidural space of the spinal cord (i.e. epidural delivery). In some embodiments, the disclosed compositions may be delivered or administered directly into a tumor (i.e. intratumoral delivery). In some embodiments, the disclosed compositions may be delivered or administered into a cavity formed by the resection of tumor tissue (i.e., intracavity delivery). Furthermore, in some embodiments, the disclosed methods can comprise a combination of the aforementioned routes of administration. For instance, a patient may receive at least one dose of the composition comprising T cells via intracavity delivery, followed by at least one dose of the composition via intraventricular delivery.

The disclosed methods of treatment improve clinical prognosis in patients compared to current standards. For instance, the disclosed methods can increase 1-year, 2-year, and 5-year survival rates. In some embodiments, the 1-year survival rate of a patient being treated according to the disclosed methods can at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or at least 100%. In some embodiments, the 2-year survival rate of a patient being treated according to the disclosed methods can at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or at least 100%. In some embodiments, the 5-year survival rate of a patient being treated according to the disclosed methods can at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or at least 100%.

In some embodiments, the disclosed methods also increase the life expectancy of a patient compared to another patient receiving conventional treatments or SOC treatment, including radiation therapy, small molecule drug therapy, therapeutic biologics like therapeutic antibodies, or a combination thereof. In some embodiments, in which the patient receiving SOC treatment can expect to survive about 15 months from initial diagnosis (overall survival or OS), the patient receiving the disclosed treatment can expect an OS of 25, 26, 27, 28, 29, 30, 31, 32, 33, 34, 35, 36 months or more. In some embodiments, the patient receiving the claimed treatment can expect an OS of 42, 48, 54, 60, 66, 72, 78, 84, 90 months or more.

The disclosed methods may improve a patient's prognosis through a variety of clinical outcomes. For instance, the disclosed methods can result in a reduction in tumor volume in a patient being treated with a composition comprising T cells. In some embodiments, the disclosed methods of treatment can result in at least a 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or at least 100% reduction in tumor volume. In some embodiments, the tumors in a patient may be completely eliminated and the patient can be cured of the malignancy.

Additionally, the disclosed methods are safe and well-tolerated. Patients being treated according to the disclosed methods may not experience significant side effects, and furthermore, may be able to discontinue taking auxiliary medications. For instance, in some embodiments, the disclosed methods will not result in any grade 3 or higher toxicities according to NCI Common Toxicity Criteria (CTC). The CTC provides a quantifiable scale of 0-5, with 0 meaning no adverse event, 1 meaning mild, 2 meaning moderate, 3 meaning sever and undesirable, 4 meaning life threatening or disabling, and 5 meaning death. Thus, side effects and or toxicities may include events like mild or moderate headaches, fatigue, myalgia, and minor nervous system disorders such as olfactory aura, but high grade toxicities will be avoided.

The CAR described herein can be produced by any means known in the art, though preferably they are produced using recombinant DNA techniques. Nucleic acids encoding the several regions of the chimeric receptor can be prepared and assembled into a complete coding sequence by standard techniques of molecular cloning known in the art (genomic library screening, PCR, primer-assisted ligation, site-directed mutagenesis, etc.) as is convenient. The resulting coding region is preferably inserted into an expression vector and used to transform a suitable expression host cell line, preferably a T lymphocyte cell line, and most preferably an autologous T lymphocyte cell line.

Various T cell subsets isolated from the patient, including unselected PBMC or enriched CD3 T cells or enriched CD3 or memory T cell subsets, can be transduced with a vector for CAR expression. Central memory T cells are one useful T cell subset. Central memory T cell can be isolated from peripheral blood mononuclear cells (PBMC) by selecting for CD45RO+/CD62L+ cells, using, for example, the CliniMACS® device to immunomagnetically select cells expressing the desired receptors. The cells enriched for central memory T cells can be activated with anti-CD3/CD28, transduced with, for example, a SIN lentiviral vector that directs the expression of the CAR as well as a truncated human CD19 (CD19t) or a truncated EGFR, a non-immunogenic surface marker for both in vivo detection and potential ex vivo selection. The activated/genetically modified central memory T cells can be expanded in vitro with IL-2/IL-15 and then cryopreserved.

In some cases, a patient suffering from a lymphoma, e.g., relapsed intermediate-grade B-cell non-Hodgkin lymphoma (NHL), will have undergone myeloablative autologous hematopoietic stem cell transplantation (HSCT) prior to treatment with CD19 CAR T cells.

Example 1

Construction and Structure of a CD19-Specific CAR

Figure 17A:
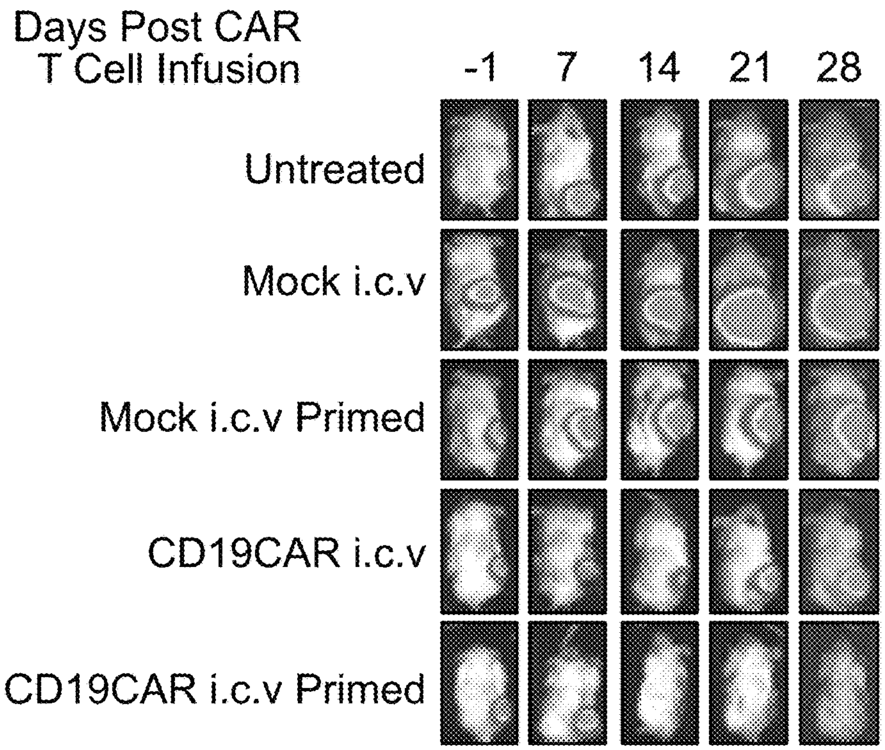
FIGS. 17A-17H: Antigen primed CAR T cells possess better effector and memory function and are able to resist tumor re-challenge. NSG mice were inoculated with SC injections of $3\times10^6$ Daudi cells on the right flank 19 days prior to CAR T cell treatment. On the day of CAR T cell infusion, $2\times10^6$CD19-CAR T cells were primed with irradiated Daudi cells at a 10:1 (CAR:tumor) ratio for 1 hr and then infused into tumor bearing mice through ICV (A-D) and IV (E-H). Mock T cells were used as controls. CD19+ fflu+ tumor burden was monitored weekly. Flux (photons/sec) was determined by measuring bioluminescence by live imaging once a week. 135 days post initial CAR T treatment, mice were re-challenged with live tumor cells by SC injection. Naïve mice were added as controls. Survival analysis was performed. N=5 mice per group. Log-rank (Mantel-Cox) and Kruskal-Wallis tests were used to ascertain the statistical significance.
Figure 17B:
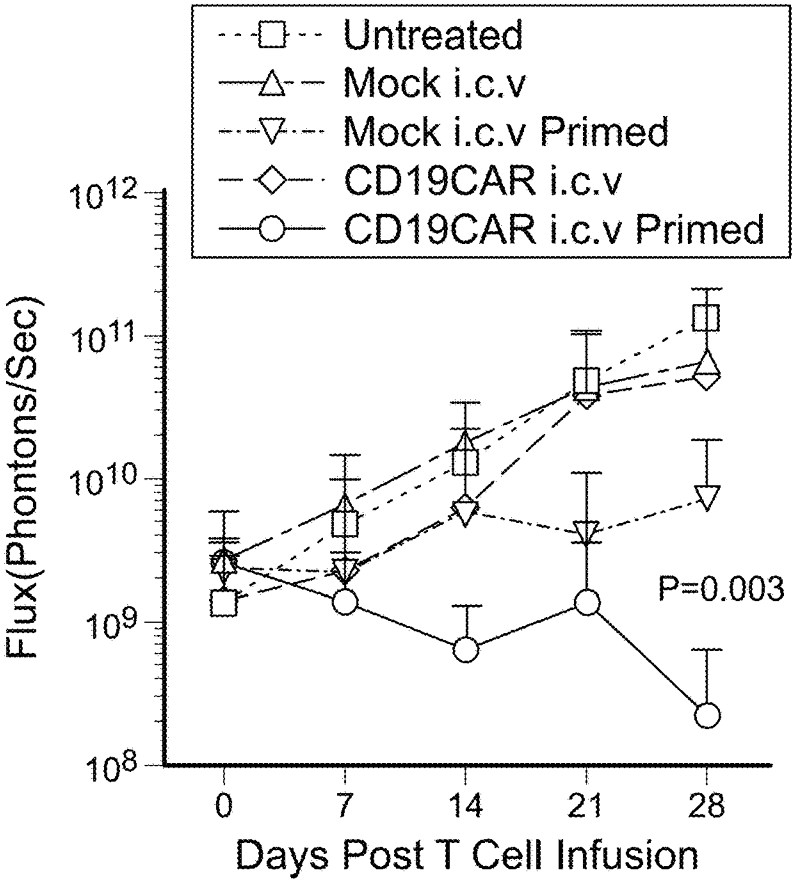

The mature amino acid sequence of the CD19-specific CAR used in the studies described below is depicted in FIG. 22 (SEQ ID NO:2). The codon optimized CAR sequence contains scFv targeted to CD19 (e.g., an scFv derived from FMC63; SEQ ID NO:3; FIG. 19B), an IgG4 Fc spacer containing two mutations (L235E; N297Q) that greatly reduce Fc receptor-mediated recognition models (the S228P mutation is also present), a CD28(M) transmembrane domain (SEQ ID NO: 24), a costimulatory CD28(gg) (SEQ ID NO: 32) cytoplasmic signaling domain, and a CD3ζ cytoplasmic signaling domain SEQ ID NO:30). A T2A ribosome skip sequence (SEQ ID NO:7) can separates this CD19 CAR sequence from a modified EGFR (SEQ ID NO:8), a cell surface detection/selection marker lacking signaling activity. This T2A linkage results in the coordinate expression of both CD19 CAR and a modified EGFR from a single transcript. The amino acid sequence the CD19 CAR used in the studies described below is shown in FIG. 22 with the various domains indicated. In this drawing, the GMCSFRa signal sequence, the CD19 scFv, IgG4(EQ) Fc, CD28 transmembrane, CD28 cytoplasmic signaling, three-glycine linker, and CD3 cytoplasmic signaling domains of the CD19 CAR are indicated. FIG. 17A depicts an amino acid sequence (SEQ ID NO:6) that can directly follow the CD3 amino acid sequence to permit coordinate express of the modified EGFR marker. The CD19 CAR was described and characterized previously (Wang et al. 2016 *Blood* 127: 2980).

Example 2

Construction and Structure of epHIV7 used for Expression of a CD19 CAR

The pHIV7 plasmid is the parent plasmid from which the clinical vector CD19-T2A-CD19t_epHIV7 was derived in the T Cell Therapeutics Research Laboratory (TCTRL) at City of Hope (COH). The epHIV7 vector used for expression of the CAR was produced from pHIV7 vector. Importantly, this vector uses the human EF1 promoter to drive expression of the CAR. Both the 5' and 3' sequences of the vector were derived from pv653RSN as previously derived from the HXBc2 provirus. The polypurine tract DNA flap sequences (cPPT) were derived from HIV-1 strain pNL4-3 from the NIH AIDS Reagent Repository. The woodchuck post-transcriptional regulatory element (WPRE) sequence was previously described.

Construction of pHIV7 is described in U.S. Pat. No. 7,446,179. Briefly, pv653RSN, containing 653 bp from gag-pol plus 5' and 3' long-terminal repeats (LTRs) with an intervening SL3-neomycin phosphotransferase gene (Neo), was subcloned into pBluescript, as follows: In Step 1, the sequences from 5' LTR to rev-responsive element (RRE) made p5'HIV-1 51, and then the 5' LTR was modified by removing sequences upstream of the TATA box, and ligated first to a CMV enhancer and then to the SV40 origin of replication (p5'HIV-2). In Step 2, after cloning the 3' LTR into pBluescript to make p3'HIV-1, a 400-bp deletion in the 3' LTR enhancer/promoter was made to remove cis-regulatory elements in HIV U3 and form p3'HIV-2. In Step 3, fragments isolated from the p5'HIV-3 and p3'HIV-2 were ligated to make pHIV-3. In Step 4, the p3'HIV-2 was further modified by removing extra upstream HIV sequences to generate p3'HIV-3 and a 600-bp BamHI-SalI fragment containing WPRE was added to p3'HIV-3 to make the p3'HIV-4. In Step 5, the pHIV-3 RRE was reduced in size by PCR and ligated to a 5' fragment from pHIV-3 (not shown) and to the p3'HIV-4, to sequence from HIV-1 pNL4-3 (55) was amplified from pNL4-3 and placed between the RRE and the WPRE sequences in pHIV6 to make pHIV-7. This parent plasmid pHIV7-GFP (GFP, green fluorescent protein) was used to package the parent vector using a four-plasmid system.

A packaging signal, psi ψ, is required for efficient packaging of viral genome into the vector. The RRE and WPRE enhance the RNA transcript transport and expression of the transgene. The flap sequence, in combination with WPRE, has been demonstrated to enhance the transduction efficiency of lentiviral vector in mammalian cells.

The helper functions, required for production of the viral vector), are divided into three separate plasmids to reduce the probability of generation of replication competent lentivirus via recombination: 1) pCgp encodes the gag/pol protein required for viral vector assembly; 2) pCMV-Rev2 encodes the Rev protein, which acts on the RRE sequence to assist in the transportation of the viral genome for efficient packaging; and 3) pCMV-G encodes the glycoprotein of the vesiculo-stomatitis virus (VSV), which is required for infectivity of the viral vector.

There is minimal DNA sequence homology between the pHIV7 encoded vector genome and the helper plasmids. The regions of homology include a packaging signal region of approximately 600 nucleotides, located in the gag/pol sequence of the pCgp helper plasmid; a CMV promoter sequence in all three helper plasmids; and a RRE sequence in the helper plasmid pCgp. It is highly improbable that replication competent recombinant virus could be generated due to the homology in these regions, as it would require multiple recombination events. Additionally, any resulting recombinants would be missing the functional LTR and tat sequences required for lentiviral replication.

The CMV promoter was replaced by the EF1α-HTLV promoter (EF1p), and the new plasmid was named epHIV7. The EF1p has 563 bp and was introduced into epHIV7 using NruI and NheI, after the CMV promoter was excised.

The lentiviral genome, excluding gag/pol and rev that are necessary for the pathogenicity of the wild-type virus and are required for productive infection of target cells, has been removed from this system. In addition, the CD19-T2ACD19t_epHIV7 vector construct does not contain an intact 3'LTR promoter, so the resulting expressed and reverse transcribed DNA proviral genome in targeted cells will have inactive LTRs. As a result of this design, no HIV-I derived sequences will be transcribed from the provirus and only the therapeutic sequences will be expressed from their respective promoters. The removal of the LTR promoter activity in the SIN vector is expected to significantly reduce the possibility of unintentional activation of host genes.

Example 3

Production of Vectors for Transduction of Patient T Cells

For each plasmid (CD19-T2A-CD19t_epHIV7; pCgp; pCMV-G; and pCMV-Rev2), a seed bank is generated, which is used to inoculate the fermenter to produce sufficient quantities of plasmid DNA. The plasmid DNA is tested for identity, sterility and endotoxin prior to its use in producing lentiviral vector.

Briefly, cells are expanded from the 293T working cell (WCB), which has been tested to confirm sterility and the absence of viral contamination. A vial of 293T cells from the 293T WCB is thawed. Cells are grown and expanded until sufficient numbers of cells exists to plate an appropriate number of 10 layer cell factories (CFs) for vector production and cell train maintenance. A single train of cells can be used for production.

The lentiviral vector is produced in sub-batches of up to 10 CFs. Two sub-batches can be produced in the same week leading to the production of approximately 20 L of lentiviral supernatant/week. The material produced from all sub-batches is pooled during the downstream processing phase, in order to produce one lot of product. 293T cells are plated in CFs in 293T medium (DMEM with 10% FBS). Factories are placed in a 37° C. incubator and horizontally leveled in order to get an even distribution of the cells on all the layers of the CF. Two days later, cells are transfected with the four lentiviral plasmids described above using the $CaPO_4$ method, which involves a mixture of Tris:EDTA, 2M CaC12, 2×HBS, and the four DNA plasmids. Day 3 after transfection, the supernatant containing secreted lentiviral vectors is collected, purified and concentrated. After the supernatant is removed from the CFs, End-of-Production Cells are collected from each CF. Cells are trypsinized from each factory and collected by centrifugation. Cells are resuspended in freezing medium and cryopreserved. These cells are later used for replication-competent lentivirus (RCL) testing.

To purify and formulate vectors crude supernatant is clarified by membrane filtration to remove the cell debris. The host cell DNA and residual plasmid DNA are degraded by endonuclease digestion (Benzonase®). The viral supernatant is clarified of cellular debris using a 0.45 μm filter. The clarified supernatant is collected into a pre-weighed container into which the Benzonase® is added (final concentration 50 U/mL). The endonuclease digestion for residual plasmid DNA and host genomic DNA as performed at 37° C. for 6 h. The initial tangential flow ultrafiltration (TFF) concentration of the endonuclease-treated supernatant is used to remove residual low molecular weight components from the crude supernatant, while concentrating the virus ~20 fold. The clarified endonuclease-treated viral supernatant is circulated through a hollow fiber cartridge with a NMWCO of 500 kD at a flow rate designed to maintain the shear rate at ~4,000 sec-1 or less, while maximizing the flux rate. Diafiltration of the nuclease-treated supernatant is initiated during the concentration process to sustain the cartridge performance. An 80% permeate replacement rate is established, using 4% lactose in PBS as the diafiltration buffer. The viral supernatant is brought to the target volume, representing a 20-fold concentration of the crude supernatant, and the diafiltration is continued for 4 additional exchange volumes, with the permeate replacement rate at 100%.

Further concentration of the viral product is accomplished by using a high speed centrifugation technique. Each sub-batch of the lentivirus is pelleted using a Sorvall RC-26 plus centrifuge at 6000 RPM (6,088 RCF) at 6° C. for 16-20 h. The viral pellet from each sub-batch is then reconstituted in a 50 mL volume with 4% lactose in PBS. The reconstituted pellet in this buffer represents the final formulation for the virus preparation. The entire vector concentration process resulted in a 200-fold volume reduction, approximately. Following the completion of all of the sub-batches, the material is then placed at −80° C., while samples from each sub-batch are tested for sterility. Following confirmation of sample sterility, the sub-batches are rapidly thawed at 37° C. with frequent agitation. The material is then pooled and manually aliquoted in the Class II Type A/B3 biosafety cabinet in the viral vector suite. A fill configuration of 1 mL of the concentrated lentivirus in sterile USP class 6, externally threaded O-ring cryovials is used. Center for Applied Technology Development (CATD)'s Quality Systems (QS) at COH released all materials according to the Policies and Standard Operating Procedures for the CBG and in compliance with current Good Manufacturing Practices (cGMPs).

To ensure the purity of the lentiviral vector preparation, it is tested for residual host DNA contaminants, and the transfer of residual host and plasmid DNA. Among other tests, vector identity is evaluated by RT-PCR to ensure that the correct vector is present. All release criteria are met for the vector intended for use in this study.

Example 4

Preparation of T Cells Suitable for Use in ACT

T lymphocytes are obtained from a patient by leukopheresis, and the appropriate allogenic or autologous T cell subset, for example, Central Memory T cells ($T_{CM}$), are genetically altered to express the CAR, then administered back to the patient by any clinically acceptable means, to achieve anti-cancer therapy.

Suitable $T_{CM}$ can be prepared as follows. Apheresis products obtained from consented research participants are ficolled, washed and incubated overnight. Cells are then depleted of monocyte, regulatory T cell and naïve T cell populations using GMP grade anti-CD14, anti-CD25 and anti-CD45RA reagents (Miltenyi Biotec) and the CliniMACS™ separation device. Following depletion, negative fraction cells are enriched for CD62L+ $T_{CM}$ cells using DREG56-biotin (COH clinical grade) and anti-biotin microbeads (Miltenyi Biotec) on the CliniMACS™ separation device.

Following enrichment, $T_{CM}$ cells are formulated in complete X-Vivo15 plus 50 IU/mL IL-2 and 0.5 ng/mL IL-15 and transferred to a Teflon cell culture bag, where they are stimulated with Dynal ClinEx™ Vivo CD3/CD28 beads. Up to five days after stimulation, cells are transduced CD19 CAR-T2A-CD19t_epHIV7 lentiviral vector at a multiplicity of infection (MOI) of 1.0 to 0.3. Cultures are maintained for up to 42 days with addition of complete X-Vivo15 and IL-2 and IL-15 cytokine as required for cell expansion (keeping cell density between $3\times10^5$ and $2\times10^6$ viable cells/mL, and cytokine supplementation every Monday, Wednesday and Friday of culture). Cells typically expand to approximately $10^9$ cells under these conditions within 21 days. At the end of the culture period cells are harvested, washed twice and formulated in clinical grade cryopreservation medium (Cryostore CSS, BioLife Solutions).

On the day(s) of T cell infusion, the cryopreserved and released product is thawed, washed and formulated for re-infusion. The cryopreserved vials containing the released cell product are removed from liquid nitrogen storage, thawed, cooled and washed with a PBS/2% human serum albumin (HSA) Wash Buffer. After centrifugation, the supernatant is removed and the cells resuspended in a Preservative-Free Normal Saline (PFNS)/2% HSA infusion diluent. Samples are removed for quality control testing.

A variety of methods can be used to produce a population of human $T_{CM/SCM/N}$ (also referred to as $T_{N/MEM}$) cells. For example, a population of $T_{CM/SCM/N}$ cells can be prepared from amixed population T lymphocytes. The population of T lymphocytes can be allogenic to or autologous to the subject ultimately treated using the cells and can be obtained from a subject by leukopheresis or blood draw.

The following method is an example of one that can be used to obtain a population of $T_{CM/SCM/N}$ cells from T lymphocytes obtained by leukapheresis or other means. Peripheral blood is collected by leukapheresis or peripheral blood draw. Day 1 of a typical manufacturing cycle is the day the ficoll procedure takes place. The subject's leukapheresis product is diluted with EDTA/PBS and the product is centrifuged at 1200 RPM for 10 minutes at room temperature with maximum brake. After centrifugation, the platelet-rich supernatant is removed and the cell pellet is gently vortexed. EDTA/PBS is used to re-suspend the vortexed cell pellets in each conical tube. Each tube is then underlayed with ficoll and centrifuged at 2000 RPM for 20 minutes with no brake at room temperature. Following centrifugation, the PBMC layer from each tube is transferred into another conical tube. The cells are centrifuged at 1800 RPM for 15 minutes with maximum brake at 4° C.

After centrifugation, the cell-free supernatant is discarded and the cell pellet is gently vortexed. The cells are washed twice using EDTA/PBS each time, and a third time using PBS. Cells are centrifuged each time at 1200 RPM for 10 minutes with maximum brake at 4° C. After the final PBS wash, the vortexed cell pellet is resuspended in complete X-VIVO 15 media (X-VIVO™ media with 10% FBS) and transferred to a transfer bag. The bag with washed PBMC is kept overnight on a rotator at room temperature on the bench top for immunomagnetic selection the next day.

Next, selection procedures are used to both to deplete the cell population of cells expressing certain markers and to enrich the cell population for cells expressing certain other markers. These selection steps preferably occur on day two of the manufacturing cycle. The cell population is substantially depleted for cells expressing CD25 and CD14. Importantly, the cell population is not substantially depleted for cells expressing CD45RA. Briefly, cells resuspended in labeling buffer (LB; EDTA/PBS with 0.5% HSA), and incubated with anti-CD14 and anti-CD25 Miltenyi antibodies for CliniMACS® depletion, and the composition is gently mixed and then incubated for 30 minutes on a rotator at room temperature on the bench top.

The depletion step is performed on a CliniMACS® device using a depletion tubing set. The recovered cells following the depletion step are transferred into tubes and centrifuged at 1400 RPM for 15 minutes with maximum brake at 4° C.

The cell-free supernatant is removed and the cell pellet is gently vortexed and resuspended. To enrich for cells expressing CD62L, the cell suspension is treated with anti-CD62L-biotin (made at the City of Hope Center for Biomedicine and Genetics), gently mixed and incubated for 30 minutes on a rotator at room temperature on the bench top.

Following the incubation period, LB is added to the tube and cells are centrifuged at 1400 RPM for 15 minutes at maximum brake at 4° C. The cell-free supernatant is removed and the cell pellet is gently vortexed. LB is added to resuspend the cell pellet in the tube and the resuspended cells are transferred to a new transfer bag. Anti-biotin (Miltenyi Biotec) reagent is added and the mixture is gently mixed and incubated for 30 minutes on a rotator at room temperature on the bench top.

The CD62L enrichment step is performed on a CliniMACS® device using a tubing set. The product of this enrichment can be frozen for storage and later thawed and activated To provide an intermediate holding step in the manufacturing, the option exists to freeze cells following the selection process. The cells are pelleted by centrifugation at 1400 RPM for 15 minutes with max break at 4° C. The cells are resuspended in Cryostor® and aliquoted into cryovials. The vials are transferred to a controlled cooling device that can cool at about 1° C./minute (e.g., a Nalgene® Mr. Frosty; Sigma-Aldrich) the cooling device is immediately transferred to a −80° C. freezer. After three days in the −80° C. freezer, the cells are transferred into a GMP LN2 freezer for storage.

We have found that cryopreserved cells exhibit good recovery and viability, maintain the appropriate cell surface phenotype when thawed several months after cryopreservation, and can be successfully transduced and expanded in vitro upon thawing.

Alternatively, freshly enriched Tcm/scm/n cells can be activated, transduced or expanded as described in Example 3, below.

Example 5

Lentiviral Transduction of $T_{CM/SCM/N}$ Cells

A $T_{CM/SCM/N}$ cell population can be transduced with a lentivirus capable of expressing a protein or proteins of interests. The following is an example of one method that can be used to transduce the T cells with a lentivirus vector with protamine sulfate/cytokine solution.

If the cells are frozen subsequent to the selection process, the cells will need to be thawed upon continuation of the manufacturing process. The cryopreserved vials are thawed in a 37° C. water bath until mostly liquid remains. The contents of the vials are placed in a conical tube containing cold X-Vivo 15 media. The cells are centrifuged at 1200 RPM for 10 minutes with max brake at 4° C. After centrifugation, the cell-free supernatant is decanted, the pellets are vortexed, and all the pellets combined into one tube in X-Vivo 15 media to be transduced with lentivirus. The cell numbers are determined and the manufacturing process continues with Dynal bead activation.

The cells are centrifuged at 1400 RPM for 10 minutes at 25° C. After centrifugation, the cell-free supernatant is removed and the cell pellet is gently vortexed and resuspended in complete X Vivo 15 media to be transduced with lentivirus. If thawed cells are being used, the centrifugation step is not necessary.

Tcm/scm/n cells are stimulated with Dynabeads® Human T expander CD3/CD28 (Invitrogen) at a 1:3 ratio (T cell: bead), then cultured in the presence of 50 U/mL rhIL-2 (Chiron) and 0.5 ng/ml rhIL-15 (CellGenix).

After incubation for 1-3 days, T cells are transduced with the lentiviral vector at a MOI typically ranging from 0.1 to 1.5 in X Vivo15 containing 10% FCS with 5 μg/mL protamine sulfate (APP Pharmaceutical), 50 U/mL rhIL-2 and 0.5 ng/mL rhIL-15. The day following the lentivirus transduction, one volume of media is added of freshly prepared media/cytokine mastermix containing complete X-VIVO 15 media and cytokines (10 μL rhuIL-2 and 0.5 μL rhuIL-15).

Cultures are then maintained at 37° C., 5% $CO_2$ in X-Vivo15 10% FCS as required to keep cell density between $3\times10^5$ and $2\times10^6$ viable cells/mL, with cytokine supplementation (final concentration of 50 U/mL rhIL-2 and 0.5 ng/mL rhIL-15) every Monday, Wednesday and Friday of culture.

CD3/CD28 Dynabead bead removal takes between days 7 to 9 after bead stimulation. The Dynal beads are removed using the DynaMag-50 or MPC magnet. After bead removal, a sample of the cell suspension is taken for counts. Based on the counts, the concentration is adjusted to approximately $0.5\times10^6$/mL.

Cultures are propagated until sufficient numbers of cells are achieved, which is typically between 8 and 18 days. During this time, a full replacement of cytokines are added to the T cell cultures. Starting on day 12 and every Monday, Wednesday and Friday thereafter, counts are taken to maintain a concentration of approximately $0.5\times10^6$ cells/mL Final harvest and cryopreservation proceeds as follows. The cell product is cryopreserved once the expanded cells reach the necessary number of viable cells required for clinical administration or research purposes. The cells are counted and in-culture samples are harvested for mycoplasma testing. The remaining cells are centrifuged at 1800 RPM for 20 minutes, maximum brake at 4° C. The cell-free supernatant is removed and all cell pellets are gently vortexed, resuspended and combined into Isolyte buffer (Braun). The tube is centrifuged at 1800 RPM for 20 minutes, max brake at 4° C. The cells are resuspended in Isolyte for a second wash.

After the second Isolyte wash, the cell-free supernatant is removed and the cell pellet is gently vortexed and resuspended in an appropriate volume of the cryopreservation media, CryoStor® 5 (BioLife Solutions), in order to have cells at an appropriate concentration. Cells are cyropreserved by placing in a controlled cooling device that can cool at about 1° C./minute (e.g., a Nalgene® Mr. Frosty; Sigma-Aldrich) or a control rate freezer system (Custom Biogenics). At completion of the freeze procedure, the cassette(s)/bag(s) and cryovials are immediately transferred into a LN2 freezer for storage.

Example 6

Phenotype of $T_{CM}$ and $T_{N/MEM}$-Derived CD19 CAR T Cells $T_{CM}$ (CD62L+CD45RO+) and $T_{N/MEM}$ (CD62L+) cells were isolated from healthy donor PBMCs and transduced to express a second generation CD19 specific chimeric antigen receptor (CAR) with a truncated EGFR (EGFRt). CAR T cells were expanded in the presence of IL-2 50 U/mL and IL-15 0.5 ng/mL for 14 days. CAR expression was defined by Erbitux-biotin and streptavidin (SA) staining as shown in FIG. 2. Both $T_{CM}$ and $T_{N/MEM}$ T cell populations express comparable levels of CD19 CAR as indicated by EGFR staining and CD8 T cells.

Example 7

Figure 3A:
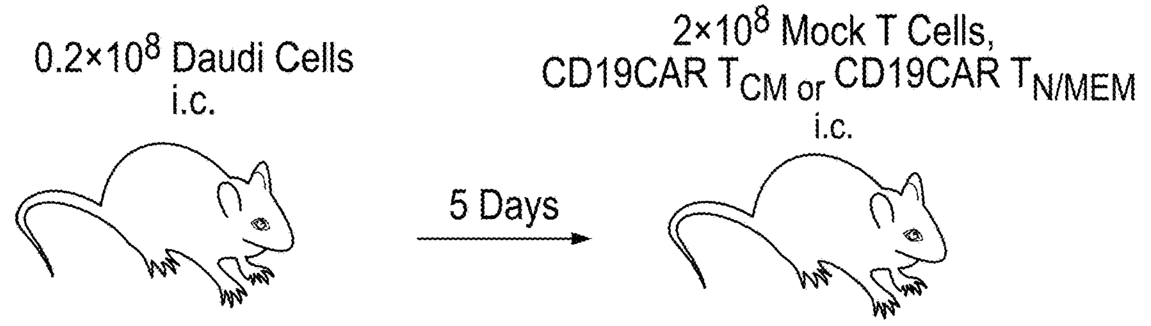
FIGS. 3A-3C: $T_{N/MEM}$-derived CD19CAR T cells exhibit superior anti-CNSL activity to $T_{CM}$-derived CD19CAR T cells. (A) NSG mice were injected intracranially (IC) with $0.2\times10^6$GFP+ ffluc+ Daudi cells. Five days later, mice received an IC local infusion of $2\times10^6$ untransduced mock T cells, $T_{CM}$ or $T_{N/MEM}$-derived CD19 CAR T cells. (B) Tumor signals were monitored by bioluminescent imaging once a week. (C) Kaplan-Meier survival curves are presented. N=5.
Figure 3B:
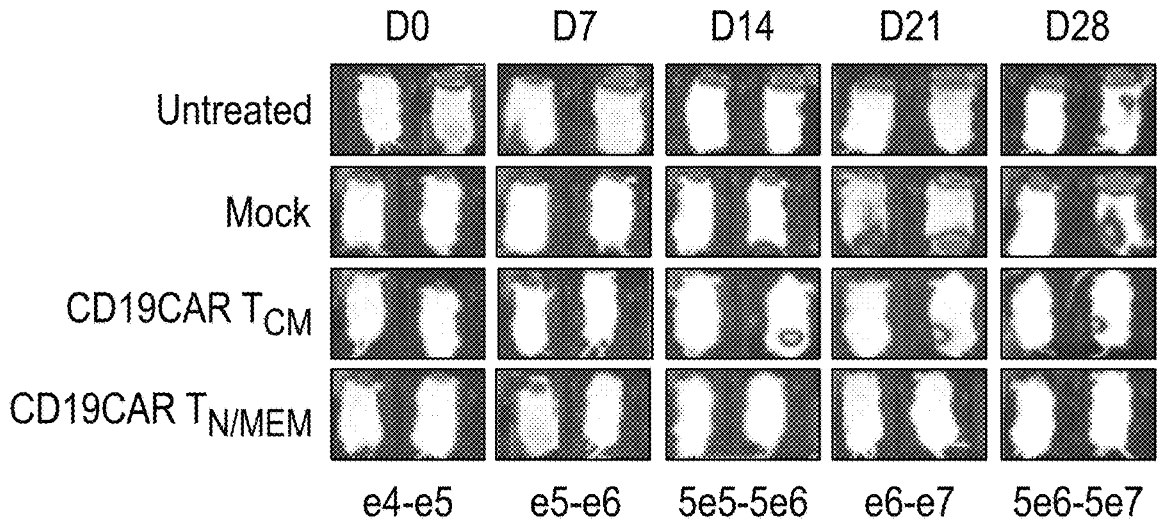
Figure 3C:
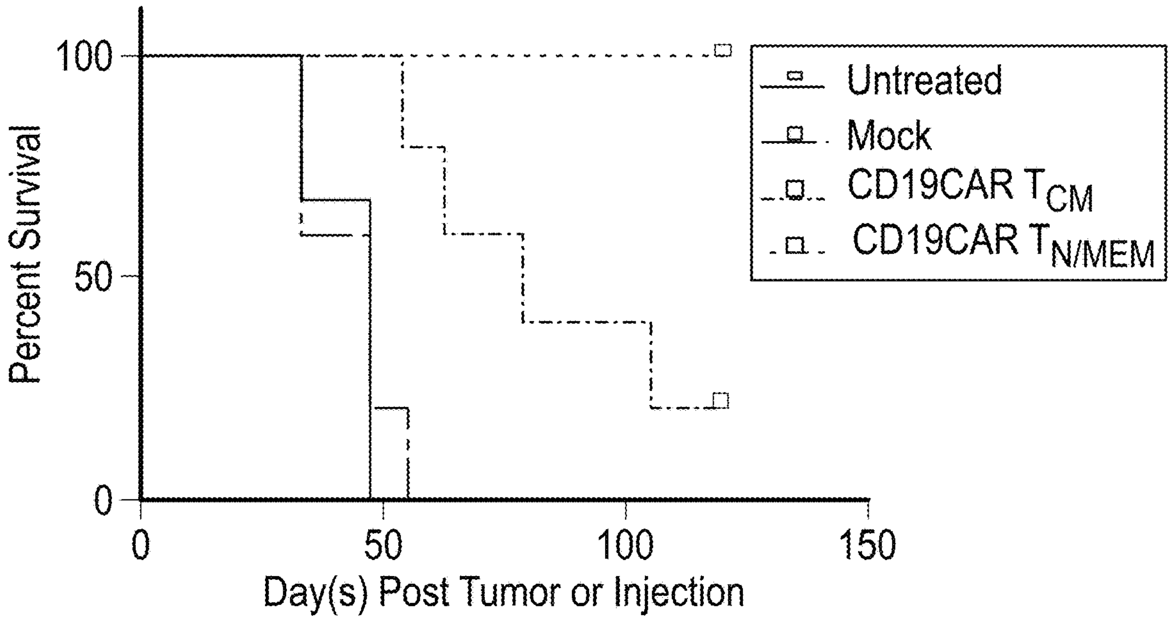

$T_{N/MEM}$-Derived CD19CAR T Cells Exhibit Superior Anti-CNSL Activity to $T_{CM}$-Derived CD19CAR T Cells NSG mice were injected intracranially (IC) with $0.2\times10^6$GFP+ ffluc+ Daudi cells (FIG. 3A). Five days later, mice received an IC local infusion of $2\times10^6$ untransduced mock T cells, $T_{CM}$ or $T_{N/MEM}$-derived CD19 CAR T cells and tumor signals were monitored by bioluminescent imaging once a week (FIG. 3B). Kaplan-Meier survival curves (FIG. 3C; N=5) show that $T_{N/MEM}$ CD19 CAR are superior to $T_{CM}$ CD19 CAR.

Example 8

Figure 4:
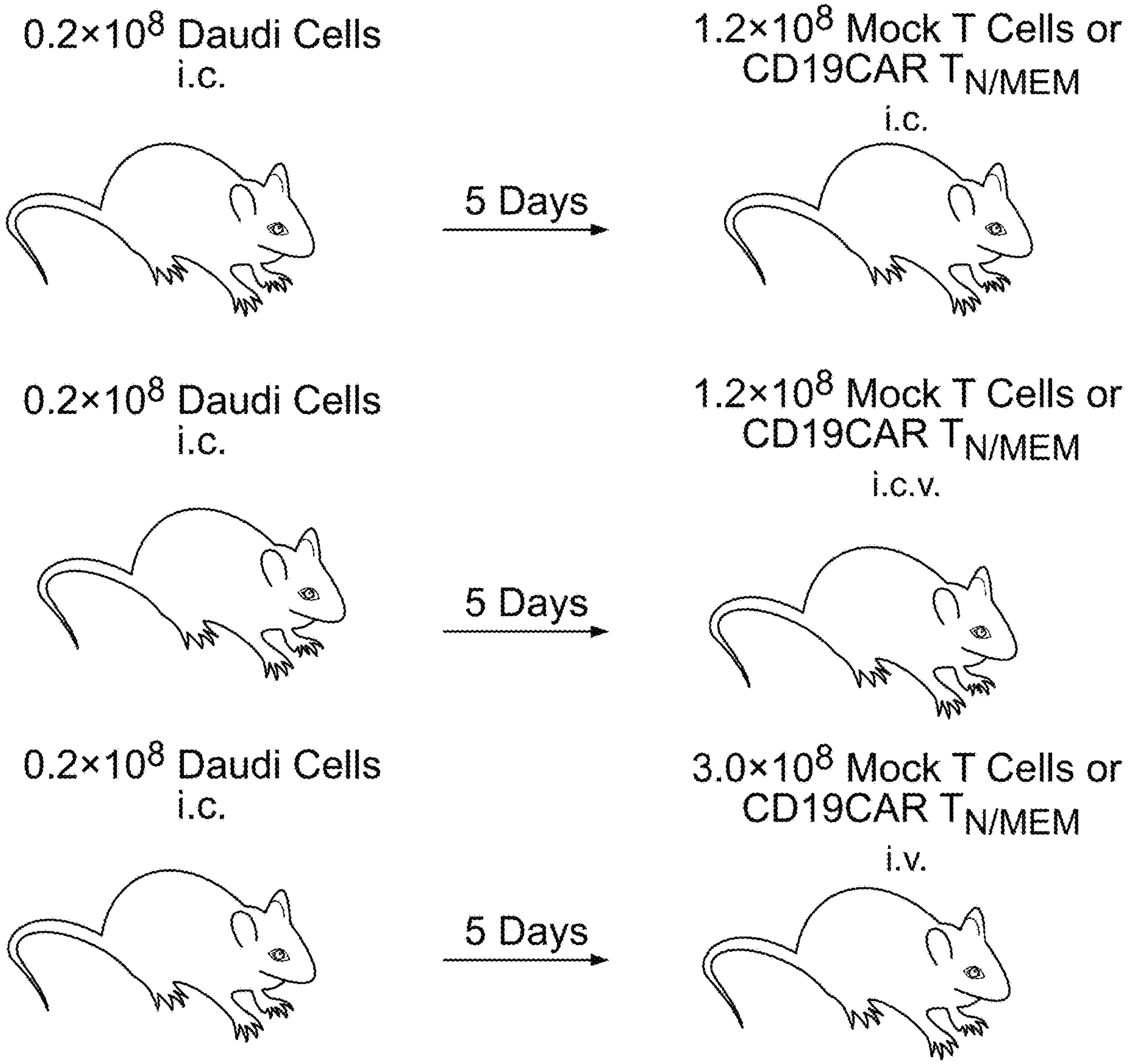
FIG. 4: Comparing efficacy of $T_{N/MEM}$-derived CD19CAR T cells against CNSL via three different delivery routes. NSG mice were injected intracranially (IC) with $0.2\times10^6$ GFP+ ffluc+ Daudi cells. Tumor was allowed to engraft for five days before mice received $T_{N/MEM}$-derived CD19 CAR T cells via three different delivery routes: 1) intracranial (IC) local infusion with $1.2\times10^6$ CD19 CAR T cells, 2) intracerebroventricular (ICV) administration with $1.2\times10^6$ CD19 CAR, and 3) intravenous (IV) injection with $3\times10^6$ CD19 CAR T cells. Tumor growth was evaluated by bioluminescent imaging once a week.

Comparing Efficacy of $T_{N/MEM}$-Derived CD19CAR T Cells Against CNSL Via Three Different Delivery Routes As shown schematically in FIG. 4, NSG mice were injected intracranially (IC) with $0.2\times10^6$ GFP+ ffluc+ Daudi cells. Tumor was allowed to engraft for five days before mice received $T_{N/MEM}$-derived CD19 CAR T cells via three different delivery routes: 1) intracranial (IC) local infusion with $1.2\times10^6$ CD19 CAR T cells, 2) intracerebroventricular (ICV) administration with $1.2\times10^6$ CD19 CAR, and 3) intravenous (IV) injection with $3\times10^6$ CD19 CAR T cells. Tumor growth was evaluated by bioluminescent imaging once a week.

Figure 5A:
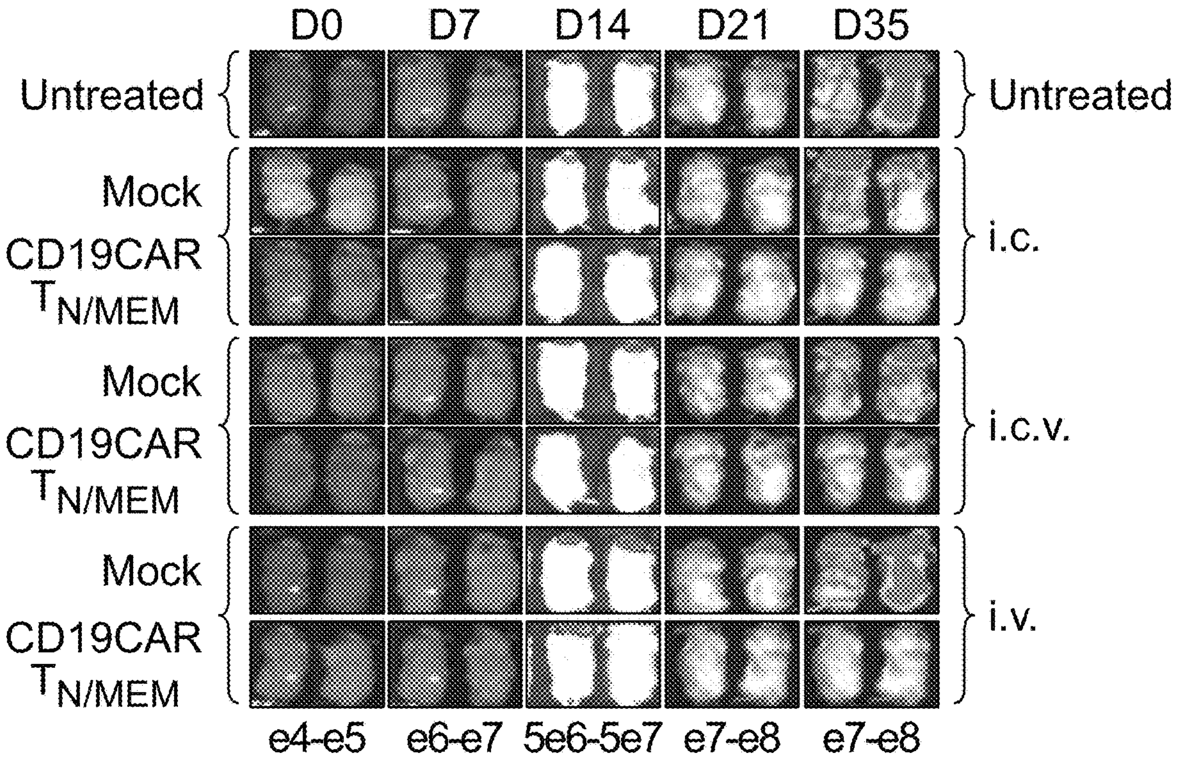
FIG. 5: Administration of $T_{N/MEM}$-derived CD19CAR T cells by all routes is able to eradicate CNSL. Both IC and ICV delivery of CD19 CAR T cells were able to completely eradicate CNS lymphoma in all mice by day 14 post CAR T cell infusion. Intravenous (IV) infusion induced significant antitumor activity 21 days post T cell infusion.
Figure 5B:
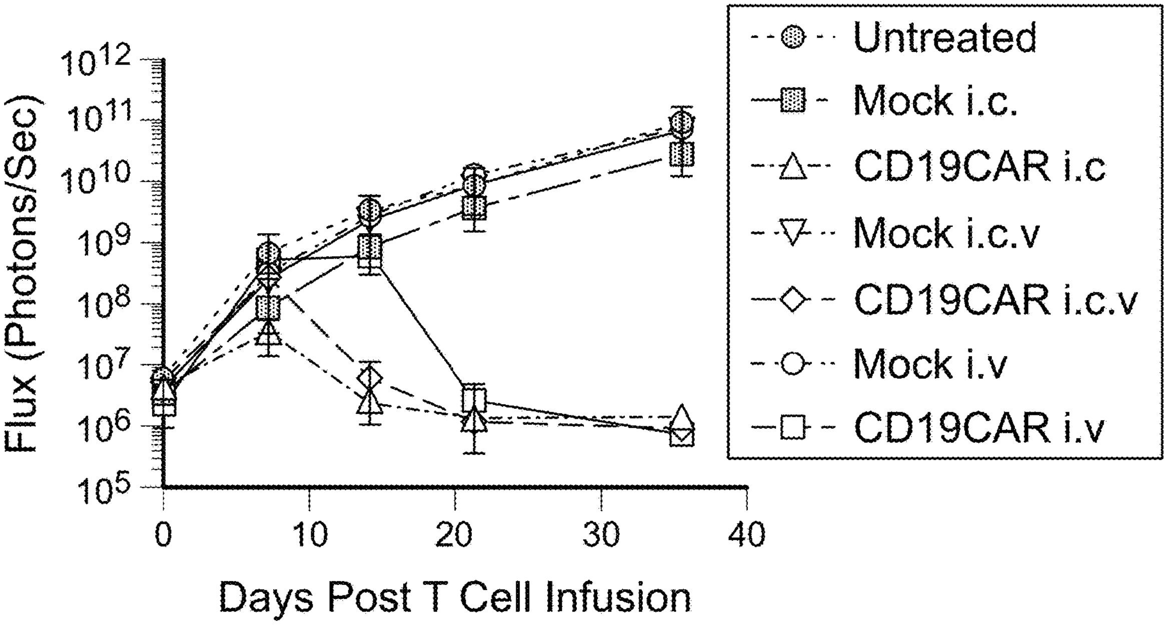

Both IC and ICV delivery of CD19 CAR T cells were able to completely eradicate CNS lymphoma in all mice by day 14 post CAR T cell infusion. IV infusion induced significant delayed antitumor activity 21 days post T cell infusion (FIG. 5) as compared with ICV delivered CD19CAR T cells.

Example 9

Figure 6:
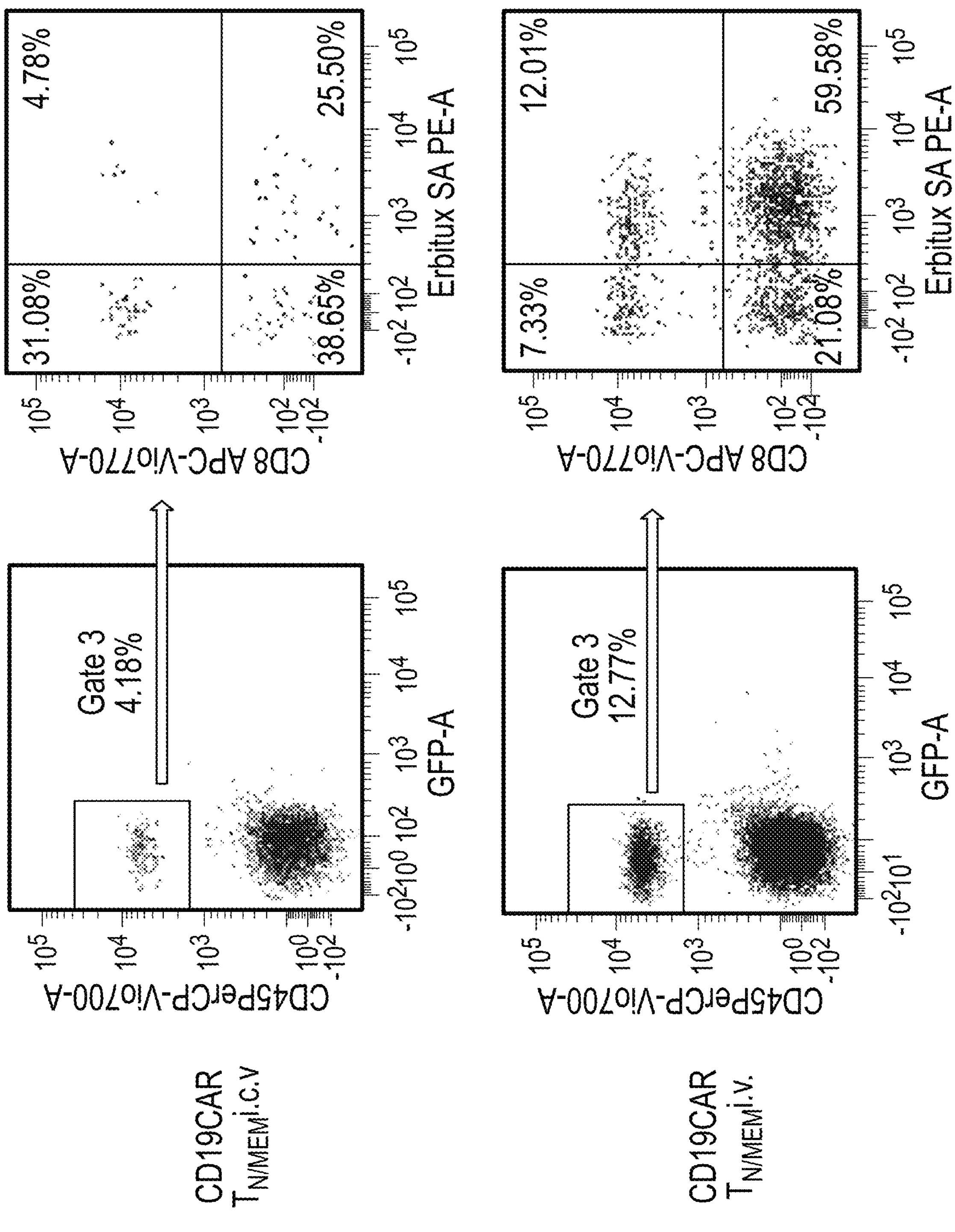
FIG. 6: CD19CAR T cells are detected in the peripheral blood of IV and ICV treated mice. 28 days after CAR T cell infusion, peripheral blood was collected retro-orbitally. Percentages of CAR T cells (CD45+ Erbitux+) are depicted.

CD19 CAR T Cells are Detected in the Peripheral Blood of IV and ICV Treated Mice Twenty-eight days after CAR T cell infusion, peripheral blood was collected retro-orbitally. Percentages of CAR T cells (CD45+ Erbitux+) are depicted in FIG. 6.

Example 10

Comparison of $T_{N/MEM}$-Derived CD19 CAR T Cells Administered IV and ICV

Figure 7:
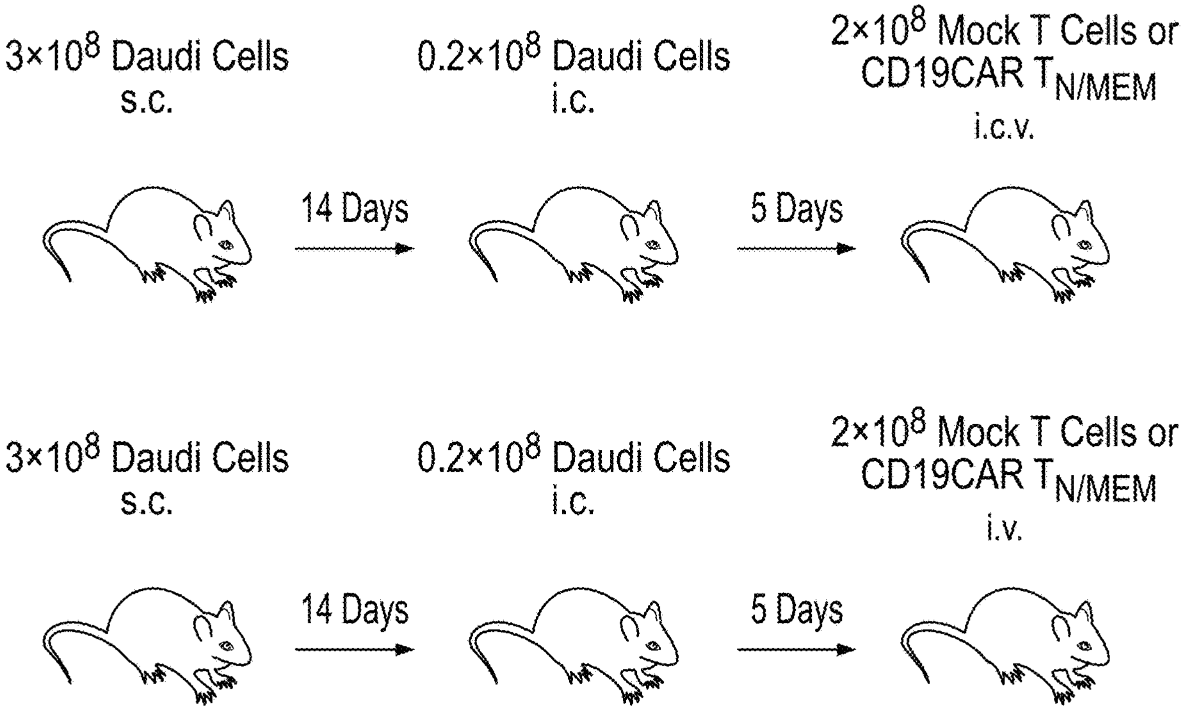
FIG. 7: Comparison of $T_{N/MEM}$-derived CD19 CAR T cells administered IV and ICV. NSG mice were injected subcutaneously (SC) with $3\times10^6$ GFP+ ffluc+ Daudi cells and 14 days later intracranially (IC) with $0.2\times10^6$ Daudi cells. Five days following IC tumor inoculation, $2\times10^6$ untransduced mock T cells or $T_{N/MEM}$-derived CD19 CAR T cells were administered either ICV or IV.
Figure 8:
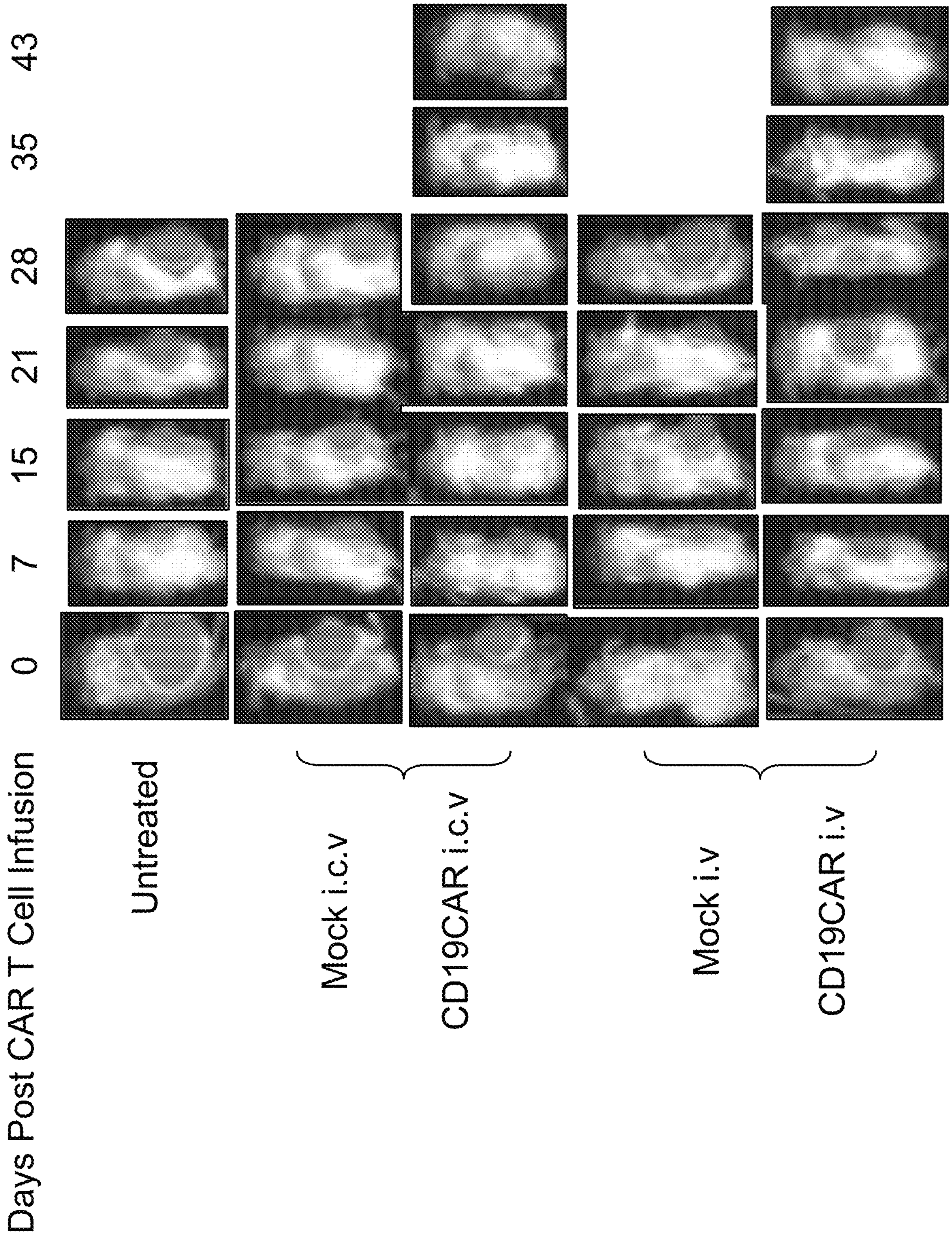
FIG. 8: $T_{N/MEM}$-derived CD19CAR T cells administered ICV are more efficacious than IV delivered CAR T cells in controlling both CNSL and systemic lymphoma. Both brain and flank tumors show faster regression in mice treated with CD19 CAR T cells administered ICV as compared to those treated with IV delivered CD19 CAR T cells.

NSG mice were injected subcutaneously (SC) with $3\times10^6$ GFP+ ffluc+ Daudi cells and 14 days later intracranially (IC) with $0.2\times10^6$ Daudi cells. Five days following IC tumor inoculation, $2\times10^6$ untransduced mock T cells or $T_{N/MEM}$-derived CD19 CAR T cells were administered either ICV or IV. This protocol is shown schematically in FIG. 7. Both brain and flank tumors show faster regression in mice treated with CD19 CAR T cells administered ICV as compared to those treated with IV delivered CD19 CAR T cells (FIG. 8).

Example 11

Figure 9A:
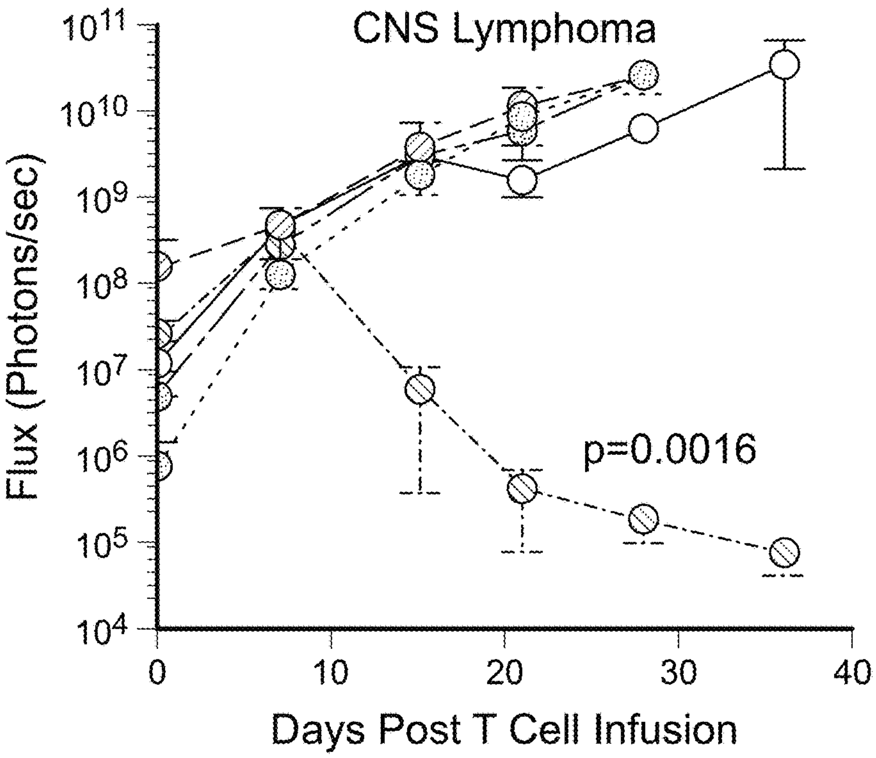
FIGS. 9A-9B: $T_{N/MEM}$-derived CD19CAR T cells administered ICV are more efficacious than IV delivered CAR T cells in controlling both CNSL and systemic lymphoma. CD19+ fflu+ tumor burden was monitored weekly. Flux (photons/sec) was determined by measuring bioluminescence with imaging once a week. CD19 CAR T cells administered ICV demonstrate the greatest ability to target both systemic (A) and CNS lymphoma (B).
Figure 9B:
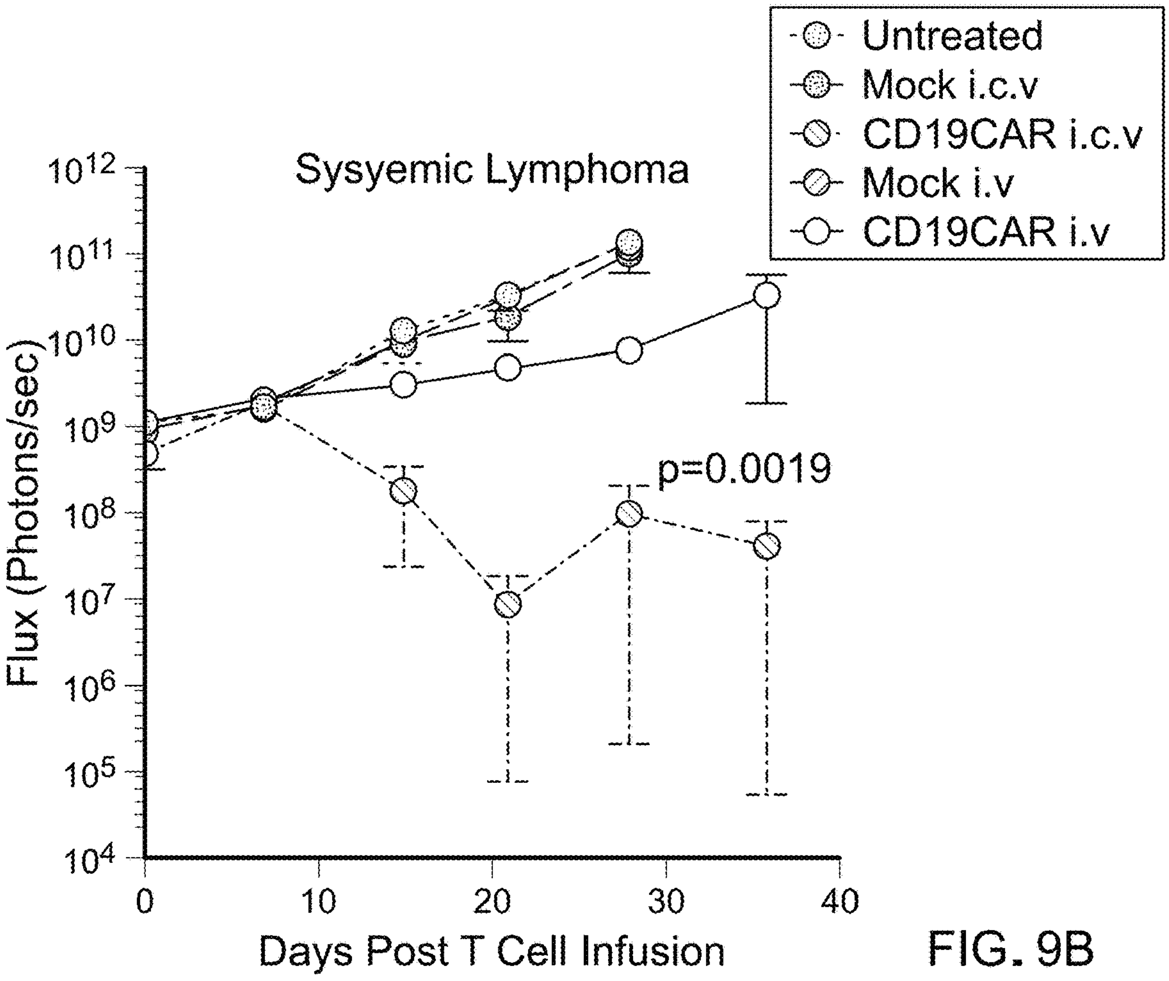

$T_{N/MEM}$-Derived CD19 CAR T Cells Administered ICV are More Efficacious Than IV Delivered CAR T Cells in Controlling Both CNSL and Systemic Lymphoma CD19+ fflu+ tumor burden was monitored weekly. Flux (photons/sec) was determined by measuring bioluminescence with imaging once a week. CD19 CAR T cells administered ICV demonstrate the greatest ability to target both systemic (FIG. 9A) and CNS lymphoma (FIG. 9B).

Example 12

Figure 10A:
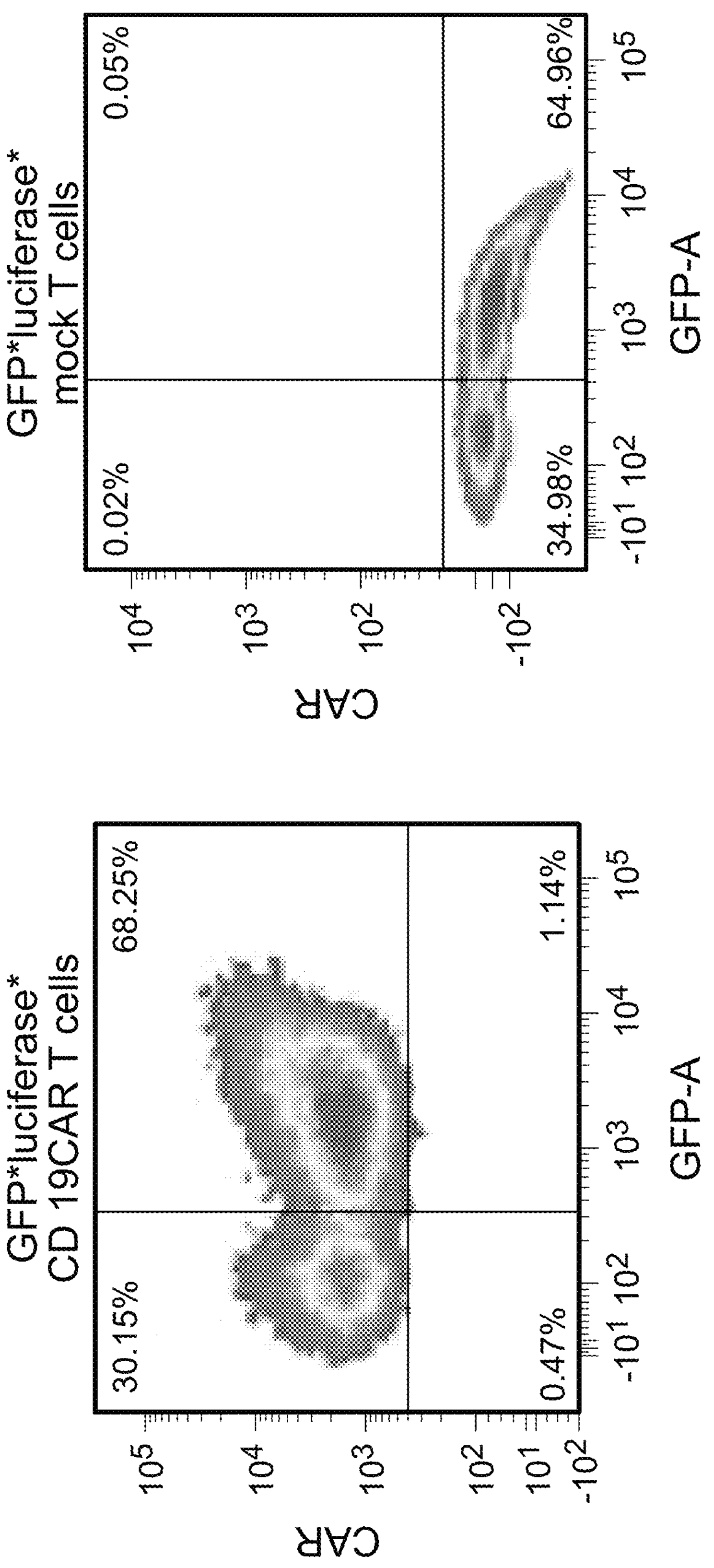
FIGS. 10A-10B: ICV administered $T_{N/MEM}$-derived CD19 CAR T cells exhibited greater proliferative capacity than IV delivered ones in lymphoma mice. CD19+ fflu+ tumor was grafted on the right flank of the mice. Nineteen days after tumor engraftment, CAR T cells that were transduced with GFPffluc were administered via ICV or IV. CAR T cell proliferation was determined by measuring bioluminescence with imaging every other day.
Figure 10B:
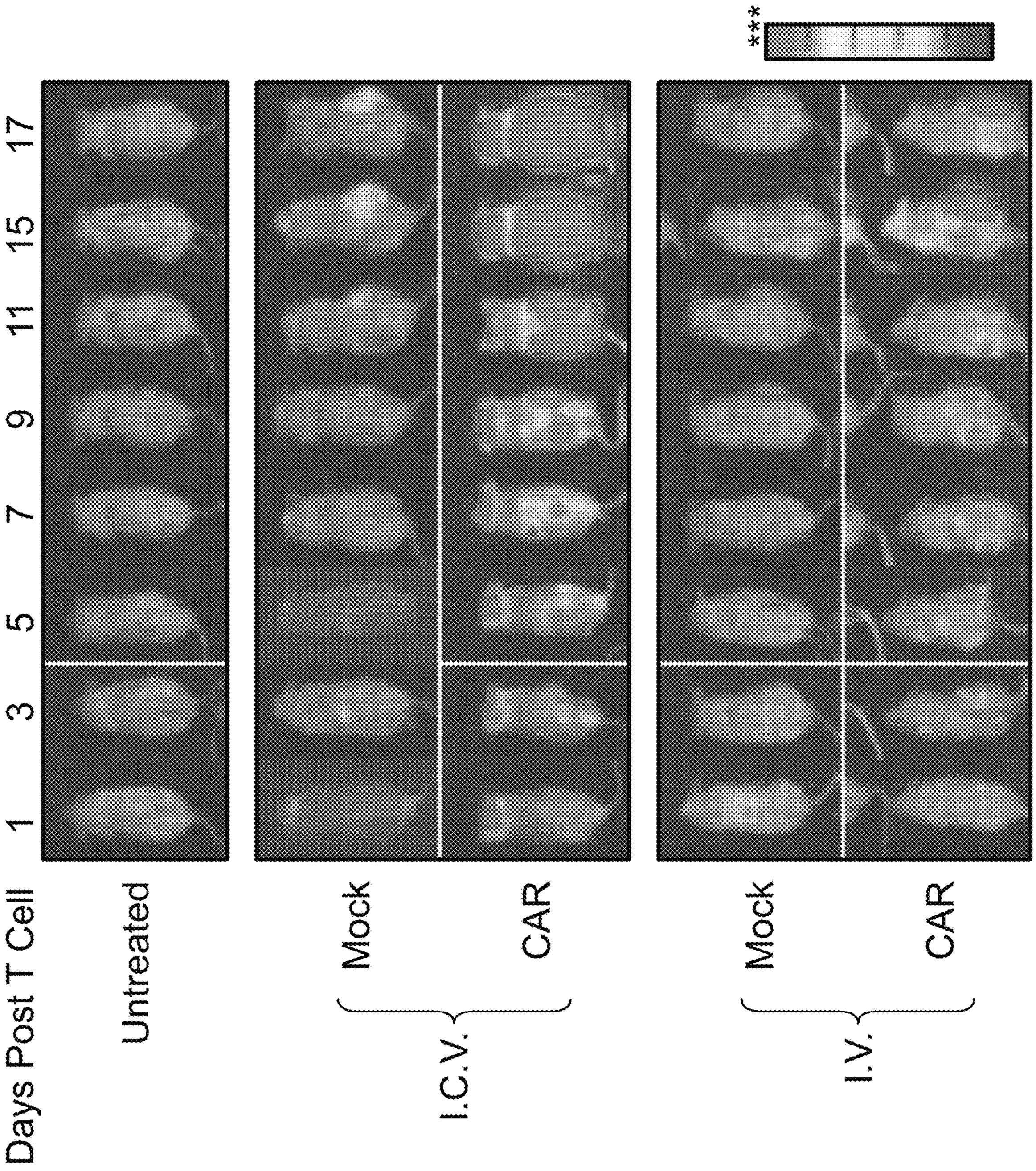

ICV Administered $T_{N/MEM}$-Derived CD19CAR T Cells Exhibited Greater Proliferative Capacity than IV Delivered Ones in Lymphoma Mice CD19+ fflu+ tumor was grafted on the right flank of the mice. Nineteen days after tumor engraftment, CAR T cells that were transduced with GFPffluc were administered via ICV or IV. CAR T cell proliferation was determined by measuring bioluminescence with imaging every other day. The results are depicted in FIG. 10.

Example 13

Figure 11A:
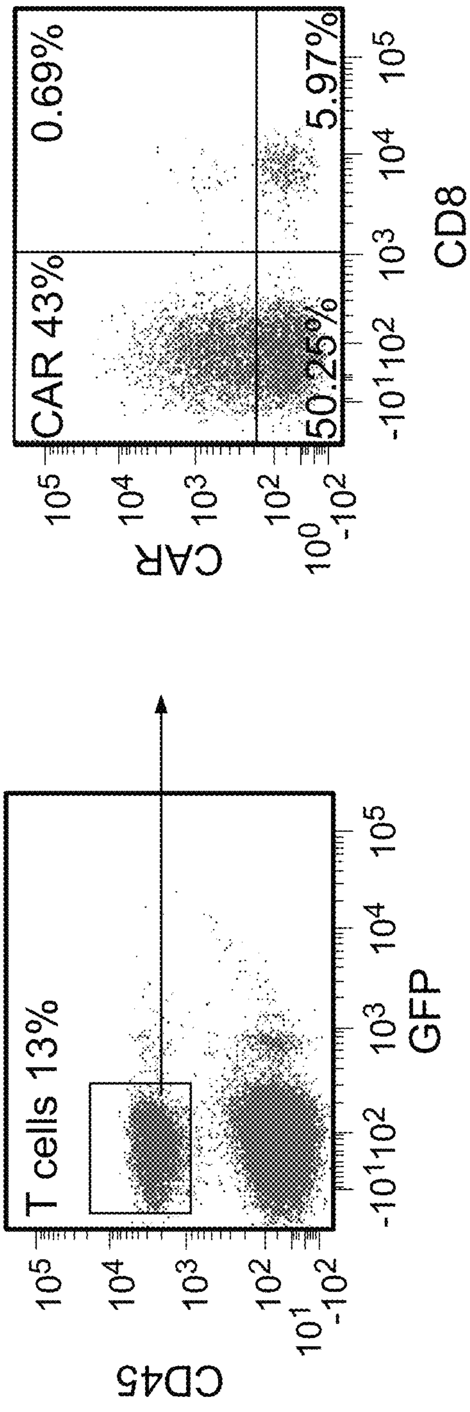
FIGS. 11A-11B: CD19 CAR T cells administered ICV persist long in vivo and maintain antitumor activity against tumor re-challenge. Daudi lymphoma cells were engineered to express firefly luciferase and injected into mouse brain as CNS lymphoma model. After tumor engraftment, mice received $2\times10^6$ CD19 CAR T cells administered intracerebroventricularly. One hundred days post CAR T cell treatment, blood was collected from the mice and human T cells and CAR T cells were analyzed with flow cytometry (A). These mice were re-challenged by injecting new daudi tumor cells on the right flank of mice. Tumor growth was monitored by measuring bioluminescence with imaging (B).
Figure 11B:
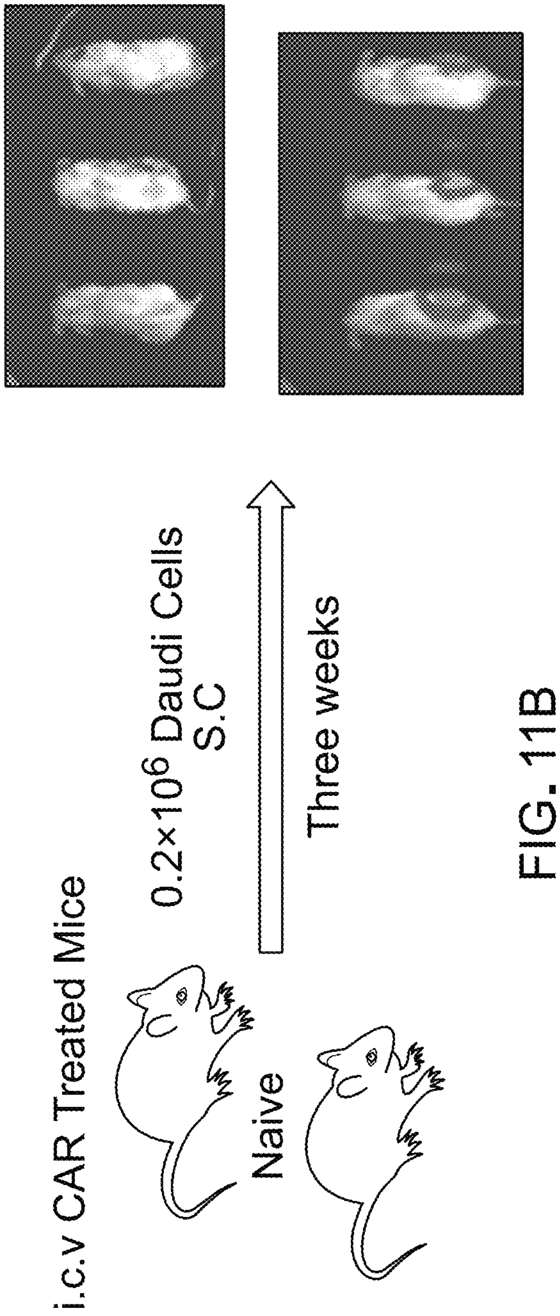

CD19 CAR T Cells Administered ICV Persist In Vivo and Maintain Antitumor Activity Against Tumor Re-Challenge Daudi lymphoma cells were engineered to express firefly luciferase and injected into mouse brain as CNS lymphoma model. After tumor engraftment, mice received $2\times10^6$ CD19 CAR T cells administered intracerebroventricularly. One hundred days post CAR T cell treatment, blood was collected from the mice and human T cells and CAR T cells were analyzed with flow cytometry (FIG. 11A). These mice were re-challenged by injecting new Daudi tumor cells on the right flank of mice. Tumor growth was monitored by measuring bioluminescence with imaging (FIG. 11B).

Example 14

Figure 12A:
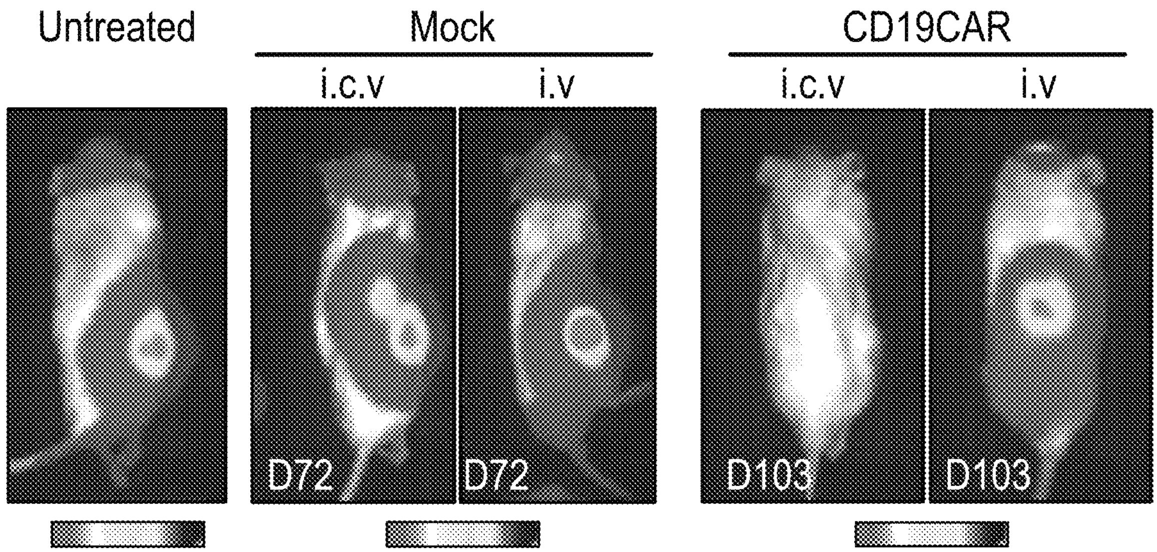
FIGS. 12A-12F: CD19-CAR T cells administered by ICV infusion are able to completely eradicate both CNS and systemic lymphoma. NSG mice were injected subcutaneously (SC) with $3\times10^6$ GFP+ ffluc+ Daudi cells and 14 days later intracranially (IC) with $0.2\times10^6$ Daudi cells. Five days following IC tumor inoculation, $2\times10^6$ untransduced mock T cells or CD19-CAR T cells were administered either ICV or IV Flux (photons/sec) was determined by measuring bioluminescence by live imaging once a week (A). N=5 mice per group. P-values were determined by comparing mean flux of each mock or CAR treated group with the untreated group using Kruskal-Wallis test. Log-rank (Mantel-Cox) test was used for survival analysis (B). Each in vivo experiment was repeated twice and representative data are presented. At the time of euthanization (day 334 for ICV group and up to 180 for IV group) blood was collected, stained with antibodies against human CD45, CD8, CD4, and CAR (Erbitux) and central memory T cell immune receptors, and analyzed by flow cytometry. Percentages of human T cells expressing CD62L, CD127, CD28, and CAR+ CD4 and CD8 T cell subsets are presented (mean±SEMs, N=3-4 mice per group). P value is depicted with two-way ANOVA analysis (C-D). Human T cells harvested from mouse spleens 334 day after ICV and 180 days post IV CAR T cell infusion were re-stimulated with REM method containing OKT3, irradiated PBMC, and LCL for 14 days and TCR repertoire was analyzed (E-F).
Figure 12B:
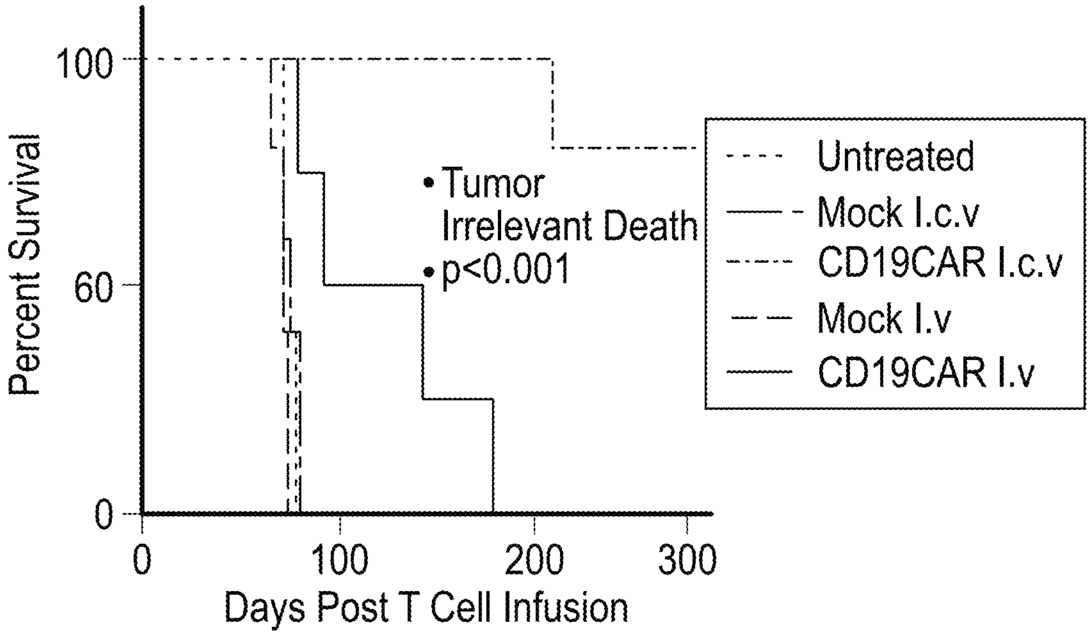
Figure 12C:
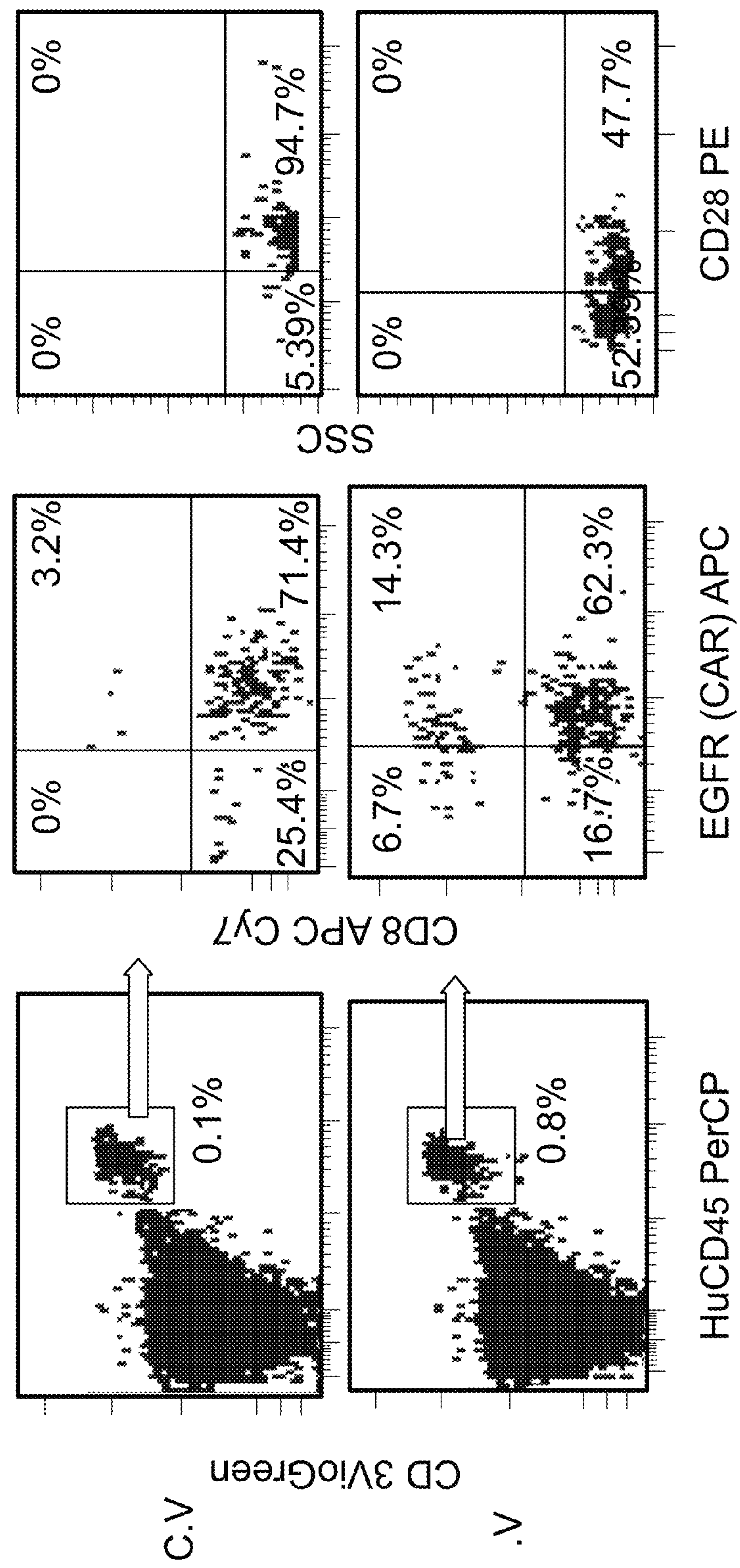
Figure 12D:
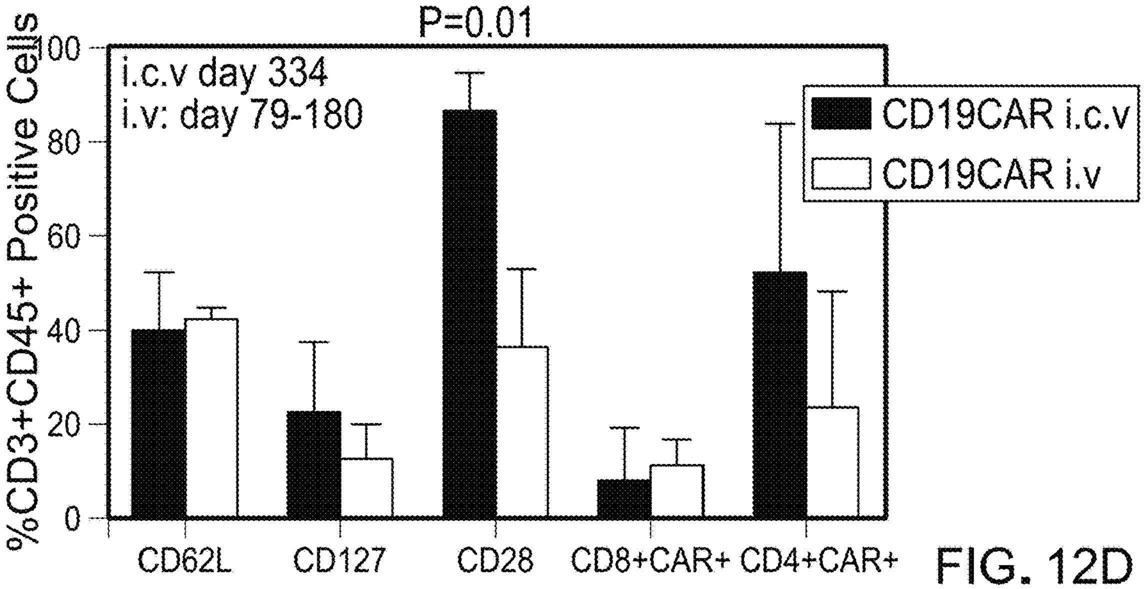
Figure 12E:
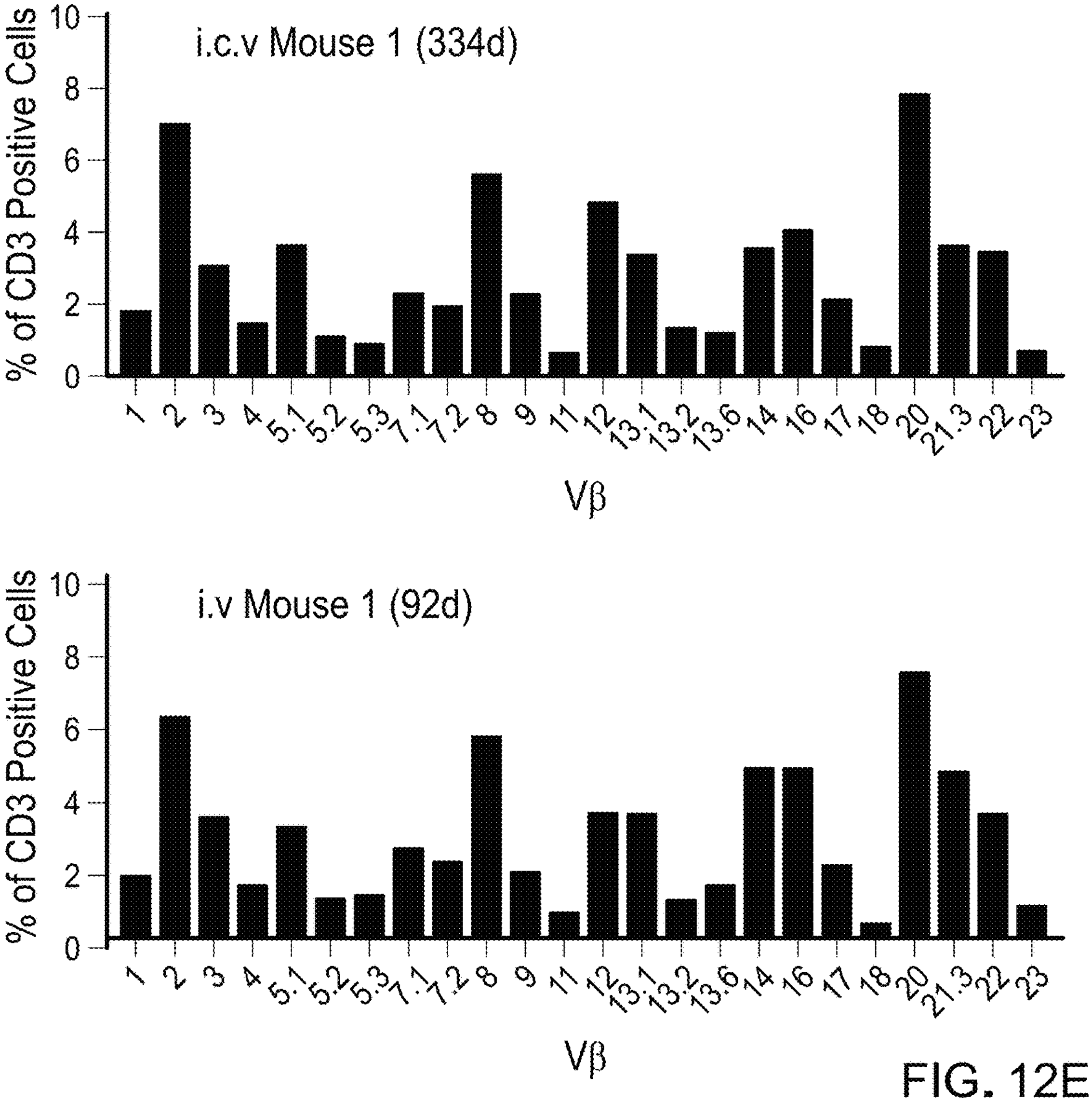
Figure 12F:
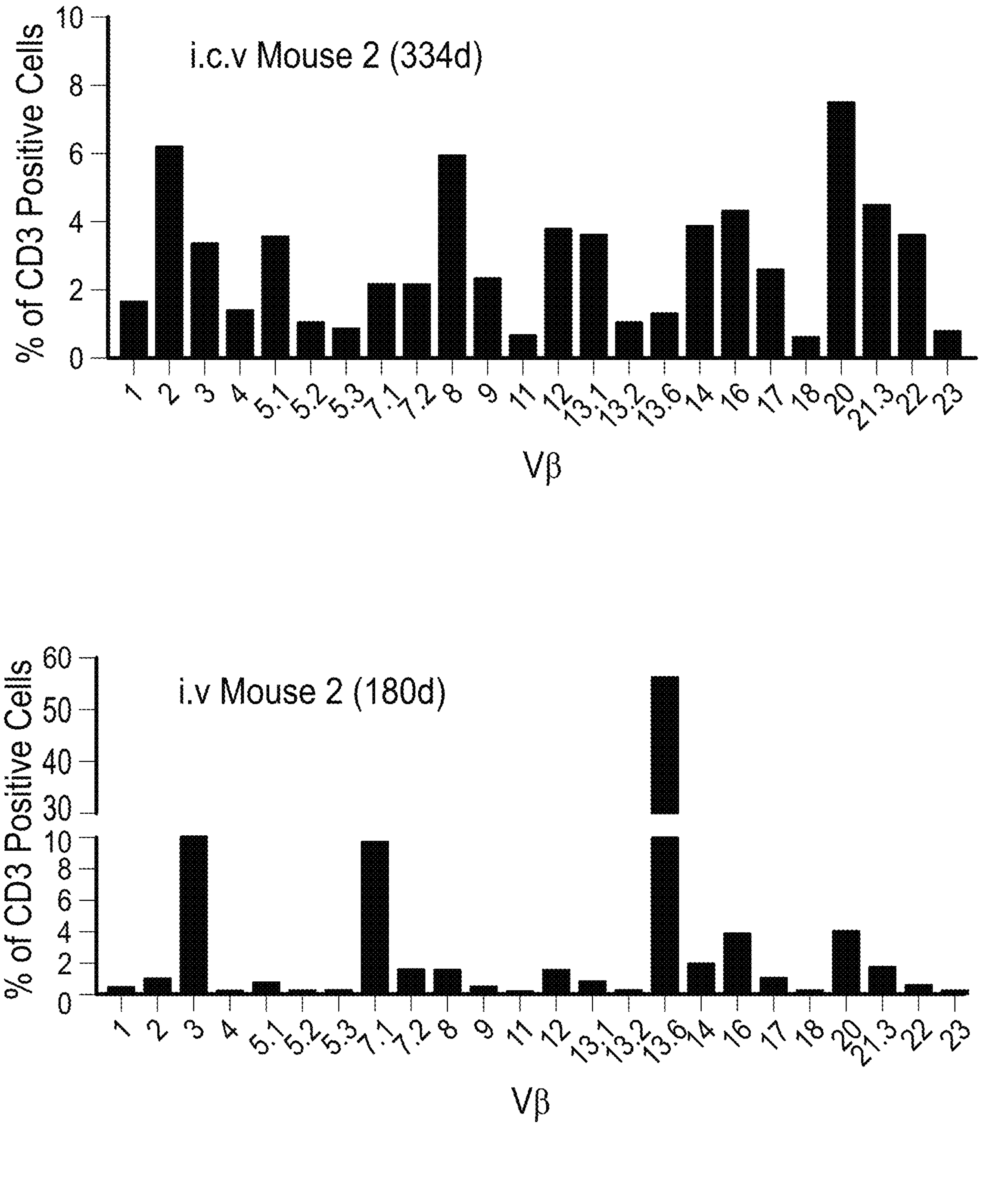

Intracerebroventricularly Administered CAR T Cells Completely Eradicate Not Only CNS Lymphoma, but Also Systemic Lymphoma As described above, CNS lymphoma and systemic lymphoma was established in mouse model by inoculating Daudi cells in the brain and SC in the right flank into the same mouse. Fifteen days post CAR T cell infusion, both CNS lymphoma and systemic tumor disappeared in the ICV treated mice (FIG. 8, FIGS. 9A-9B and FIG. 12A) and all mice survived tumor-free for over 300 days until the experiment was terminated (FIG. 12E). However, the same number of CAR T cells delivered through IV showed a dramatically delayed response. Complete remission was observed 43 days post CAR T cell infusion, but tumors eventually relapsed. All IV treated mice died before day 200 and imaging data indicate that mice died of both CNS lymphoma and systemic lymphoma relapse (FIG. 12A), suggesting that IV CAR T cells failed to completely eradicate either CNS or systemic lymphoma, which could be the result of impaired CAR T cell function and persistence.

Example 15

Intracerebroventricularly Administered CAR T Cells Retain Memory Phenotype and Function with a Broad TCR Vbeta Repertoire and Ability to Proliferate in Vitro Blood samples were collected at the end points (334 days for ICV and up to 180 days for IV) and analyzed by flow cytometry. CAR T cells were detected in both ICV and IV treated groups. Interestingly, even though no tumors were detected in the ICV treated mice, human CAR T cells were detected in the blood and the majority of CAR T cells were CD4 positive (FIGS. 12C-D), indicating that ICV-infused CAR T cells have the capability of homeostatic proliferation and the persisting CD4 CAR T cells, which express significantly higher levels of CD28 (p=0.01), contribute to curing disease. To understand whether the superior antitumor activity is due to clonal or polyclonal expansion, human T cells harvested from mouse spleen 334 day after ICV treatment and 180 days post IV treatment were re-stimulated with REM method containing OKT3, irradiated PBMC, and lymphoblastoid cell lines (LCL) for 14 days and their TCR repertoire was analyzed. The data indicate that there is no skewed TCR Vbeta usage of the ICV-delivered CAR T cells, therefore it is a generalizable feature of CAR T cells (FIG. 12E), similar to input cell product before infusion.

Figure 13A:
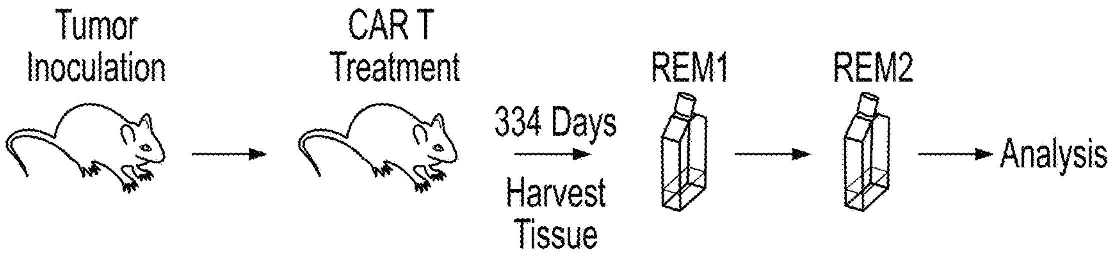
FIGS. 13A-13E: ICV administered CD19-CAR T cells exhibit greater proliferative capacity than IV delivered CD19-CAR T cells in tumor-bearing mice. T cells harvested from mouse spleens (334 days for ICV mice and 180 days for IV mice) were stimulated with OKT3 and feeders, including PBMC and LCL, for 2 cycles (14 days/cycle) (A). Percentages of CAR T cells and fold changes post first and second stimulation are presented after staining with an antibody against EGFR (B-C). Phenotypic analysis for CD161, CD127, and CD62L expression was performed after the second stimulation (D-E).
Figure 13B:
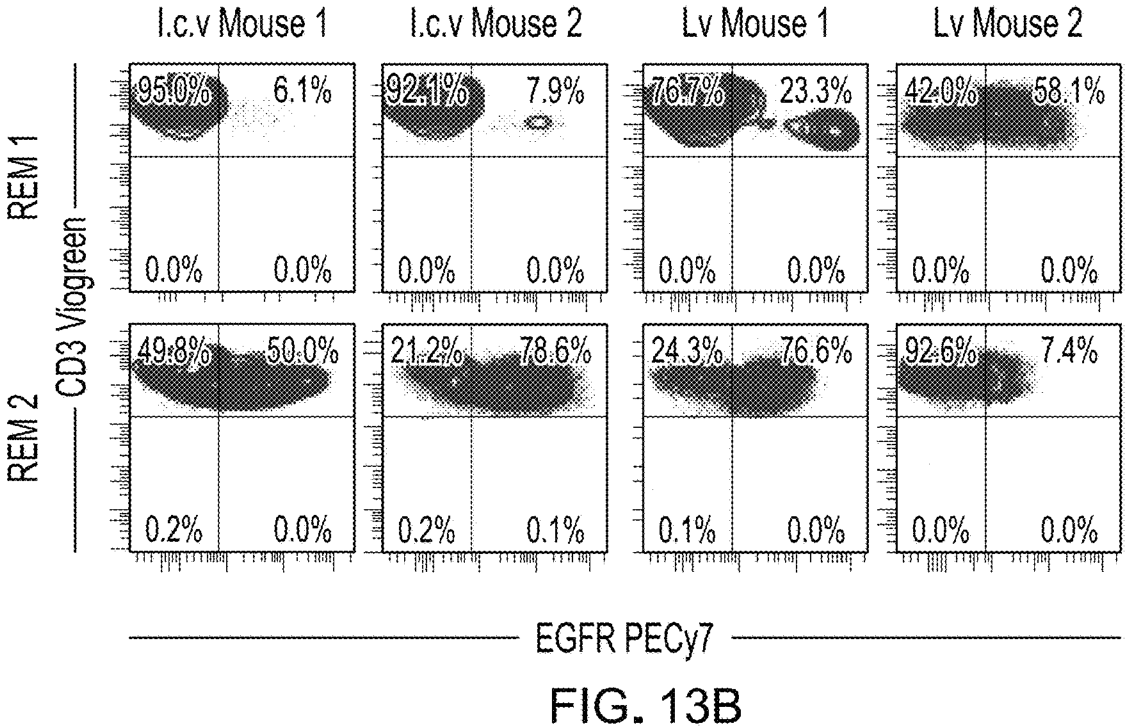
Figure 13C:
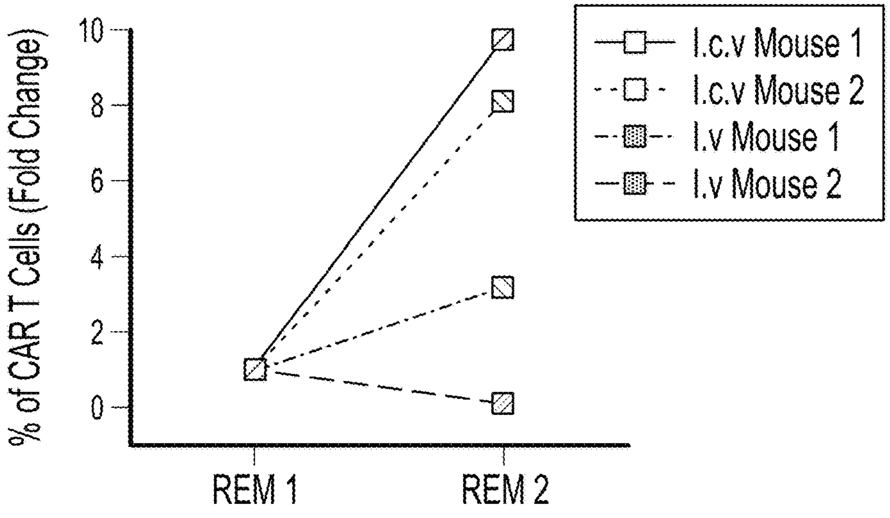
Figure 13D:
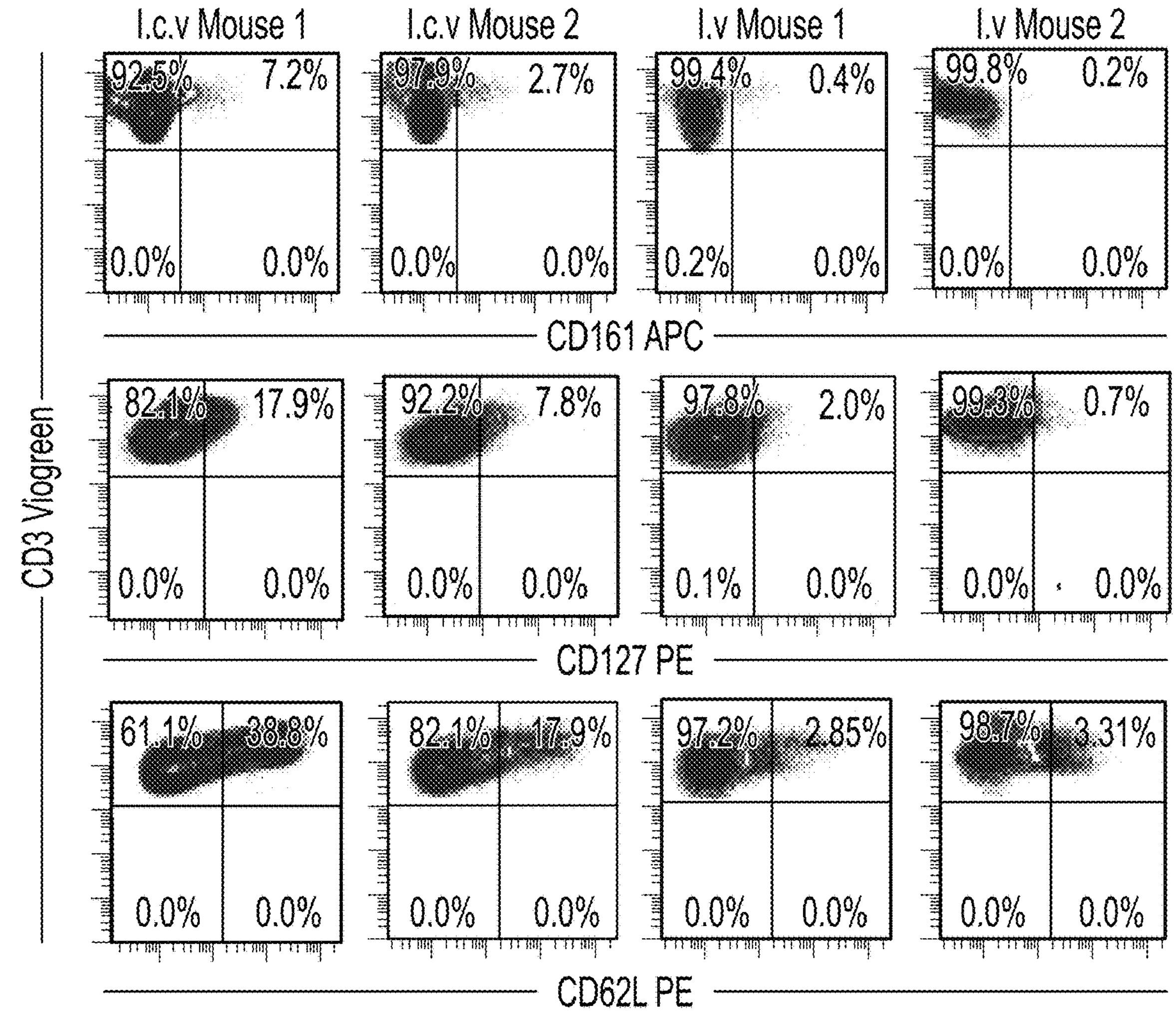
Figure 13E:
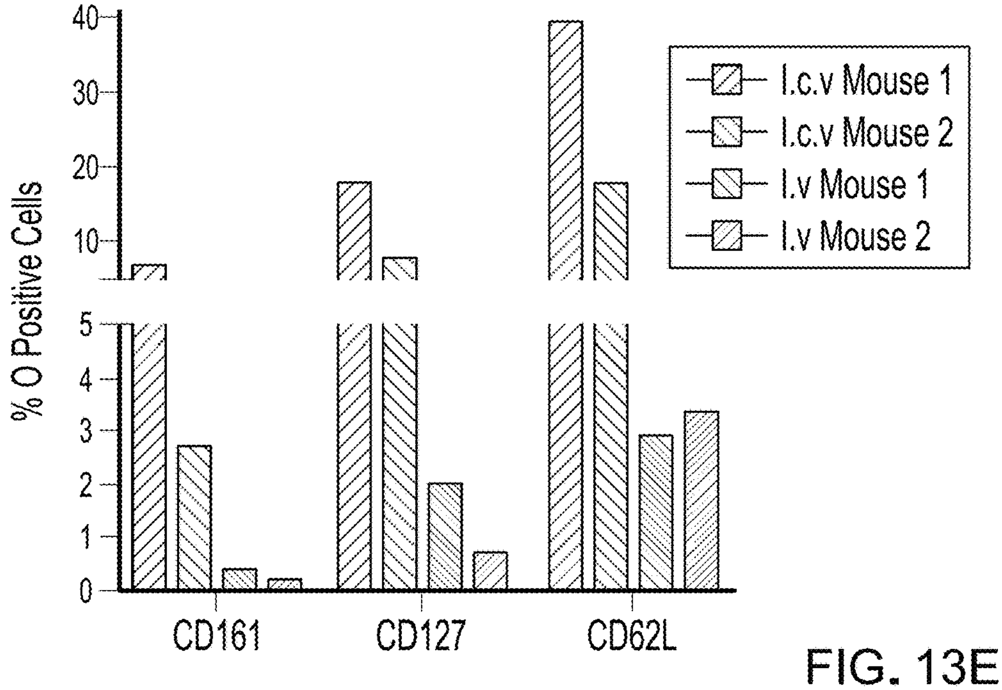
Figure 14A:
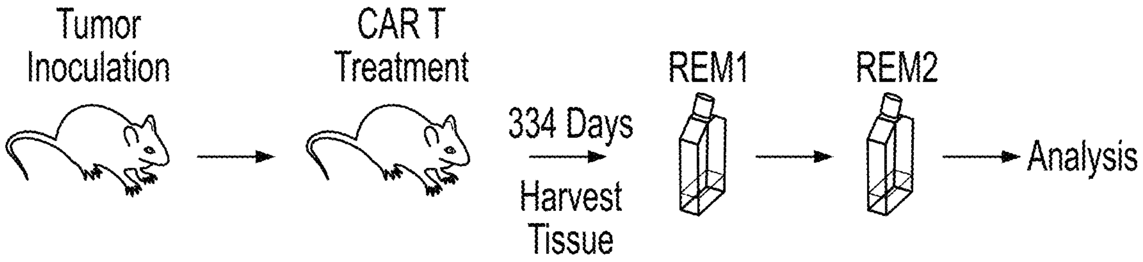
FIGS. 14A-14D: ICV and IV administered CD19-CAR T cells exhibit differences in glucose uptake and mitochondrial morphology. T cells harvested from mice (334 days for ICV mice and 180 days for IV mice) were stimulated with OKT3 and feeders, including PBMC and LCL for 2 cycles (14 days/cycle) (A). Uptake of NBDG was analyzed after different time points. Data from the 30 min time point are presented (B). Percentages of 2-NBDG positive cells in CD62L positive and CD62L negative cell populations are presented (C). T Cells were incubated in T cell medium with 100 nM MitoTracker (Green) Mitochondrial selective probe for 30 mins at 37° C. $1\times10^5$ cells were embedded onto slides by cytospin and fixed with 4% PFA before staining with DAPI for 1 min. The mitochondrial photos were taken using a LSM880 confocal microscope (D).
Figure 14B:
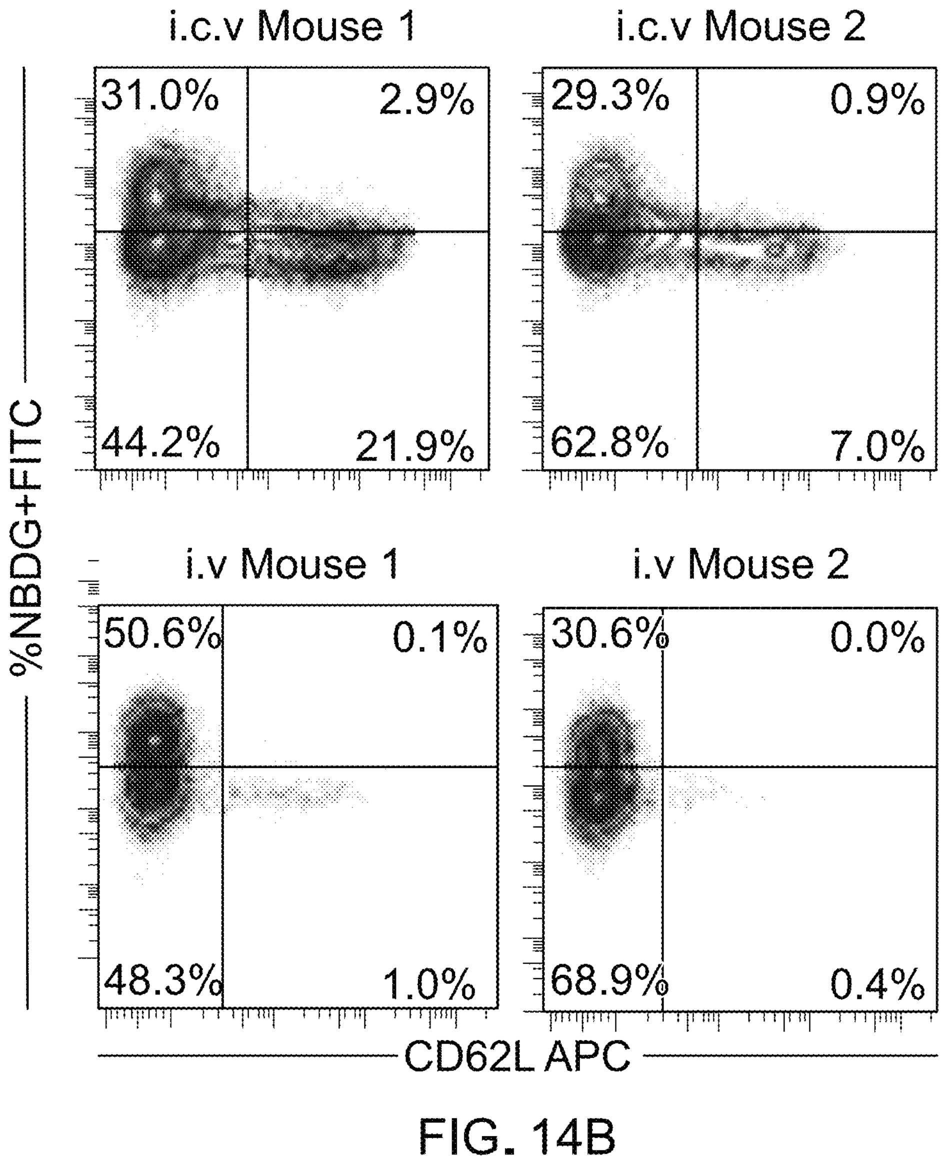
Figure 14C:
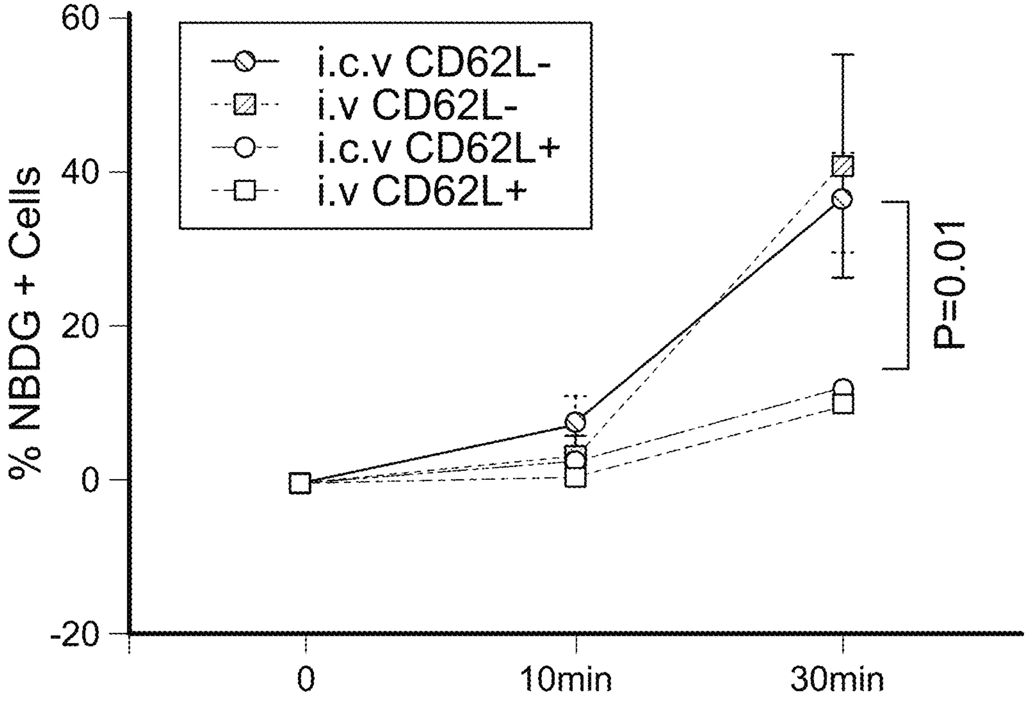
Figure 14D:
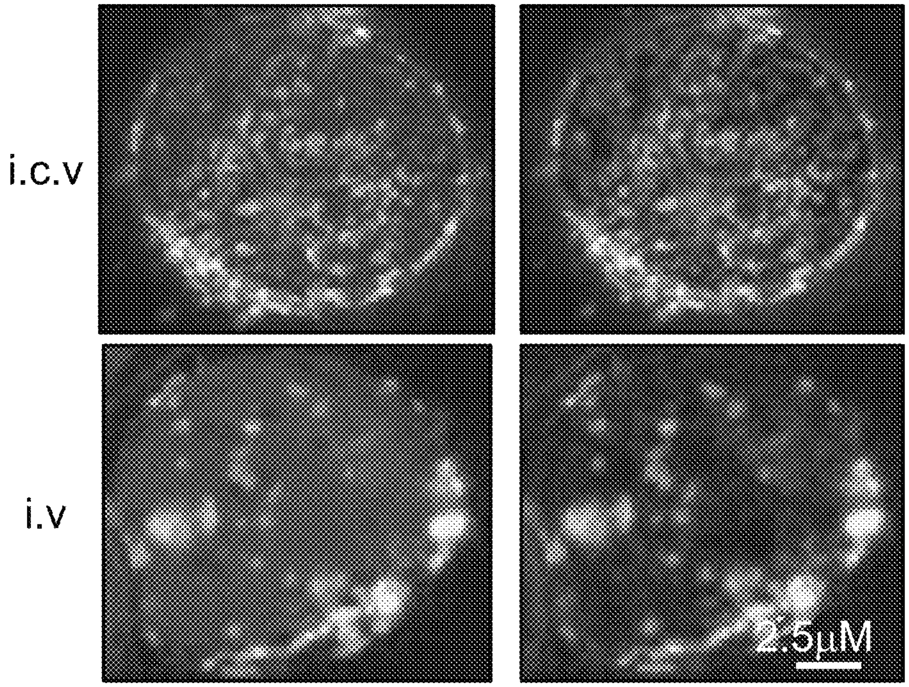

To further investigate the stem-like feature of CSF nurtured CAR T cells, an in vitro serial re-stimulation with the T cells harvested from mice (334 days of ICV mice and 180 days of IV mice) was performed. T cells were stimulated with OKT3 and feeders, including PBMC and LCL, for 2 cycles (14 days/cycles). CAR T cells from 2 of 2 ICV treated group expanded from 8% after REM1 to 79% after REM2, whereas CAR T cells from IV treated mice were less expanded or decreased (FIGS. 13A-C), suggesting ICV CAR T cells, but not IV CAR T cells, are able to continue to expand with repetitive in vitro stimulation. In spite of 334 days of in vivo incubation and repeated in vitro stimulation, the CAR T cells from ICV treated mice maintained higher levels of CD127, CD62L, and CD161—markers that represent central memory T cells and memory stem cells with high efflux capacity when compared with CAR T cells from IV treated mice (FIGS. 13D-E). Furthermore, functional studies of the T cells demonstrated that the CD62L positive cells exhibited significantly lower levels (p=0.01) of uptake of a glucose analog, NBDG, than CD62L negative cells (FIGS. 14A-C), supporting the memory function and phenotype of the cells. To meet different bioenergetic requirements, effector T cell development involves activation of mitochondrial fission and subsequent fragmentation, while memory T cell development involves inhibition of mitochondrial fission, leading to mitochondrial elongation. Here T cells from CAR-treated mice were harvested, in vitro expanded and analyzed for mitochondrial morphology. Data shows that T cells from ICV and IV treated mice possess distinct mitochondrial morphologies. ICV treated mice maintain fused networks and appear elongated, while T cells form IV treated mice have punctate mitochondria (FIG. 14D). This observation is in line with the memory phenotype and function of T cells seen post ICV delivery, suggesting that mitochondrial remodeling is a signaling mechanism that instructs T cell metabolic programming, which is acquired during CSF conditioning.

Example 16

Figure 15A:
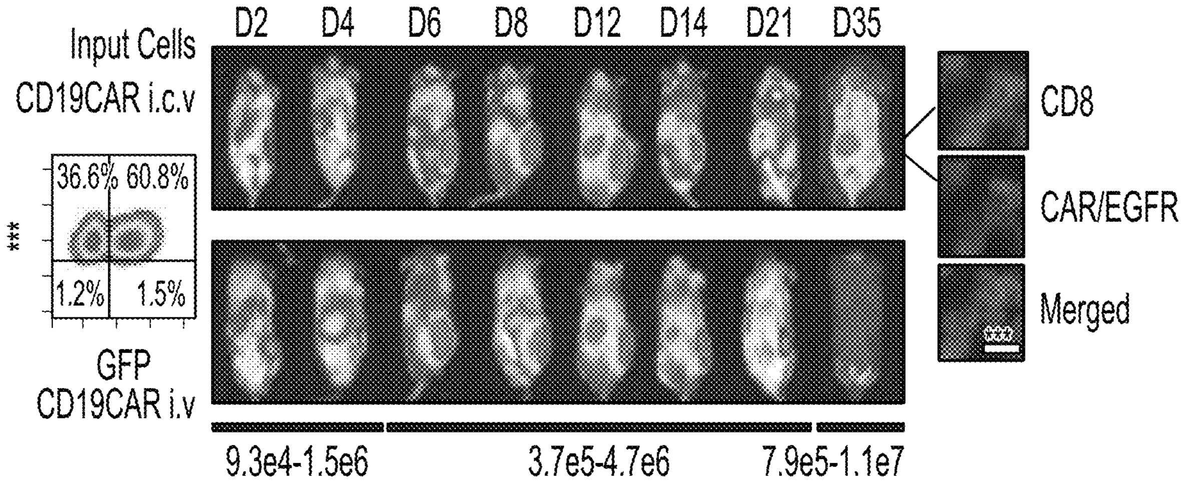
FIGS. 15A-15D: ICV delivered CAR T cells exhibit similar trafficking, but superior proliferative and persistence potential when compared with IV delivered CAR T cells. CD19-CAR T cells were transduced with GFPffluc (A) and expanded in vitro. NSG mice were implanted with Daudi tumors (SC) on the right flank. Nineteen days after tumor engraftment, $2\times10^6$ GFPffluc CAR T cells were administered via ICV or IV and CAR T cell proliferation was determined by measuring bioluminescence by live imaging every other day (A-B). The tumors were harvested 4 weeks after T cell infusion and stained for both CD3 and CAR (EGFR) using standard IHC (A). Blood was collected at different time points after CAR infusion and T cell (anti-human CD45) and CAR+ T cell (anti-EGFR) levels were detected by flow cytometry (C-D). N=5 mice per group. P-values were determined with the Mann-Whitney test. Experiments were repeated twice and representative data are presented.
Figure 15B:
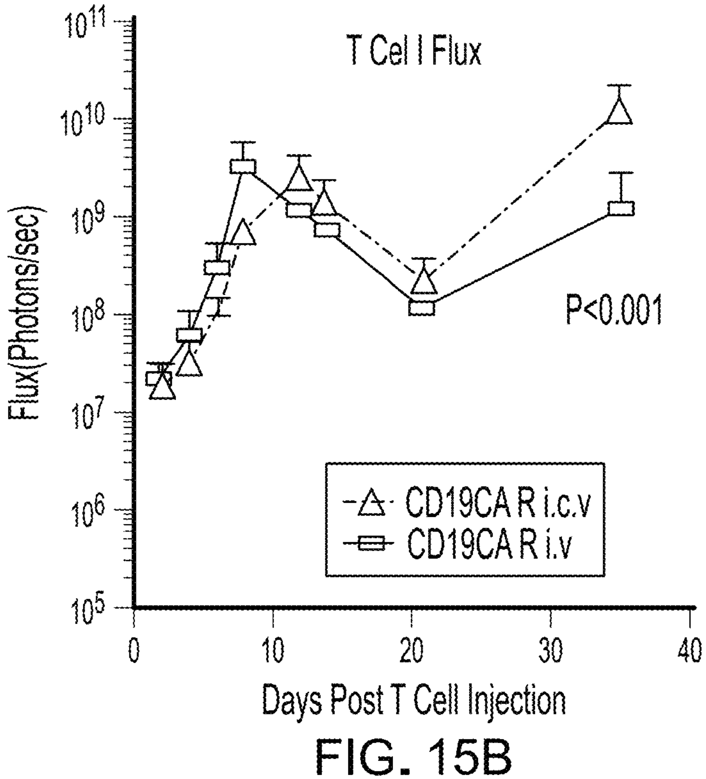
Figure 15C:
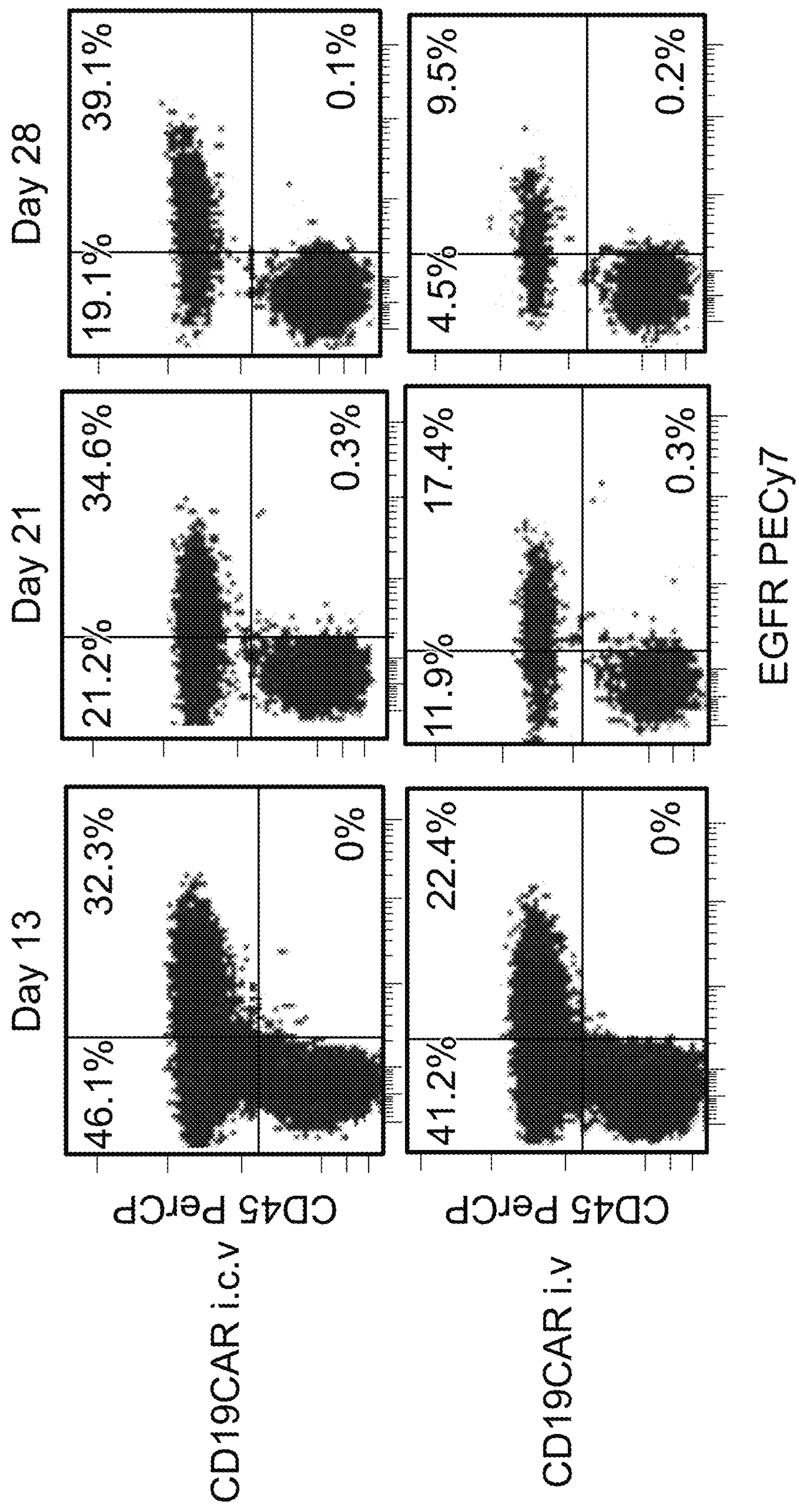
Figure 15D:
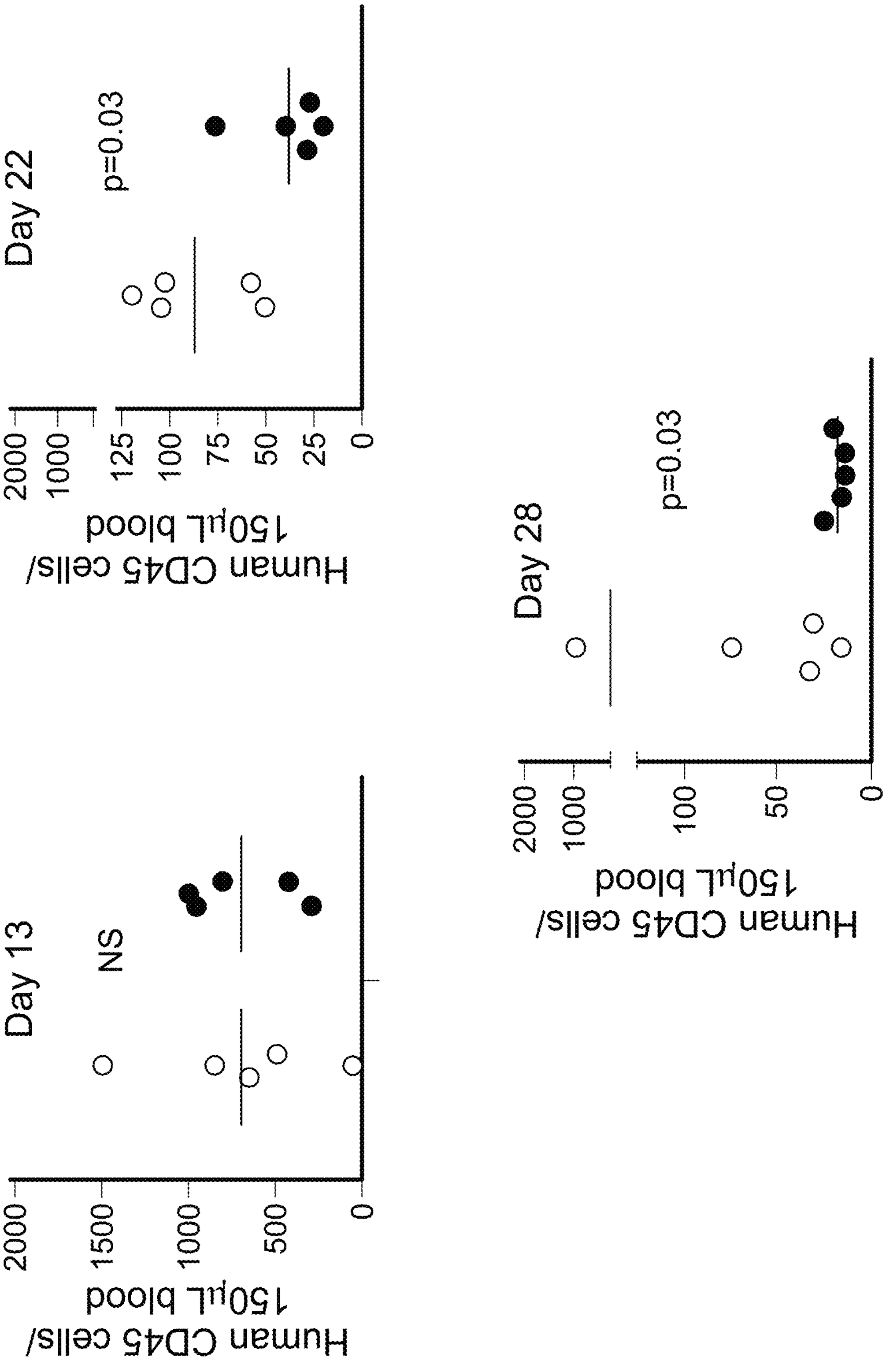

Intracerebroventricularly Administered CAR T Cells Exhibit Efficient Trafficking and Superior Proliferative and Persistence Potential when Compared With IV Delivered CAR T Cells To understand and compare the differences in trafficking and expansion following ICV and IV CAR delivery, CD19-CAR T cells were transduced with GFPffluc (FIG. 15A) and administrated ICV and IV into NSG mice bearing SC Daudi tumors in the right flank. ICV delivered CAR T cells were able to migrate to the SC tumors as quickly and efficiently as IV delivered CAR T cells. Supportively, the CAR T cells infiltrated SC tumors and were double positive for CD3 and CAR by IHC staining. Interestingly CAR T cell signals were significantly higher in ICV mice than IV mice ($P<0.001$) (FIGS. 15A-B) and CAR T cells persist in ICV mice while CAR T cells in IV mice decline dramatically from 70% on day 13 to 13% on day 28 ($P<0.05$) (FIGS. 15C-D). This expansion is antigen dependent as mock T cells did not expand in vivo. Consistently, in a separate short-term experiment, ICV CAR T cells exhibited more tremendous expansion ($P<0.01$) and superior antitumor activity than IV CAR treated mice.

Example 17

CSF Microenvironment Reprograms CAR T Cell for Better Memory and Less Exhaustion The results described above raise the possibility that exposure of CAR T cells to the CSF via ICV infusion may reprogram CAR T cells to execute potent anti-CNS lymphoma, and subsequently, anti-systemic lymphoma activity once they migrate to peripheral circulation, as well as to maintain T cell memory.

Compared with blood, CSF is cell-free and protein-free. In addition, there are other elements of difference between CSF and blood such as the lower levels of glucose and potassium in the CSF compared with serum. Glucose and potassium are known to play a key role in T cell memory and function.

Figure 16A:
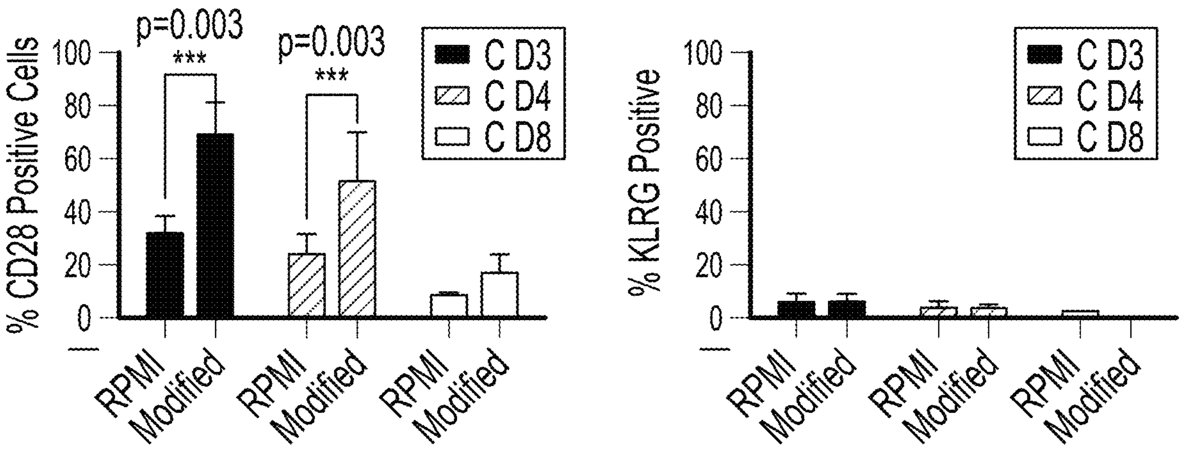
FIGS. 16A-16D: CSF environment-reprogrammed CAR T cells exhibit enhanced memory features and downregulated glycolytic metabolism. CAR T cells were activated, transduced, and expanded for 13 days in modified RPMI (60 mg/dL glucose and 2.8 mEq/L potassium) or in regular RPMI (200 mg/dL glucose and 5.3 mEq/L potassium). Phenotypic analysis was performed by flow cytometry. Data from 4 different human donors are presented. ($P<0.01$ with two-way ANOVA) (A). CD19-CAR T cells were co-cultured in RPMI and human CSF for 48 hrs. Phenotypic analysis was performed by flow cytometry. Means±SEM of 4 different donors are presented (B). RT-PCR array with the CD19-CAR T cells co-cultured in RPMI and CSF for 48 hrs was performed. Fold changes of genes in CSF over RPMI>1.3 are listed (N=4 donors) (C). CAR T cells were stimulated with Daudi cells in CSF and RPMI for 48 hrs overnight. Cytokines in the supernatant were measured with cytometric bead array using the Bio-Plex Human Cytokine 17-Plex Panel (D). N=6 replicates. Two-way ANOVA was used for statistical analysis.
Figure 16B:
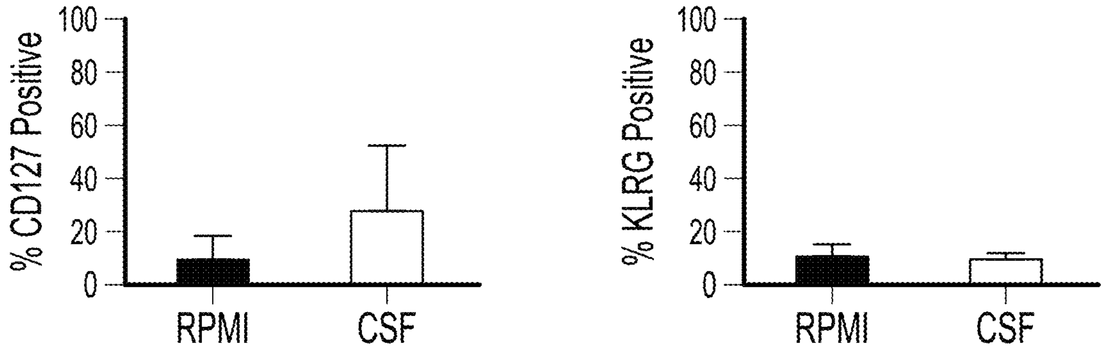

To confirm that levels of glucose and potassium and other factors in CSF play a role in CAR T cell phenotype and to understand the characteristics of CSF and RPMI treated CAR T cells, RPMI 1640 (Invitrogen) was modified to contain 60 mg/dL glucose 2.8 mEq/L potassium, the same concentrations of glucose and potassium as in CSF, in comparison to regular RPMI containing 200 mg/dL glucose and 5.3 mEq/L potassium. CAR T cells from 4 different donors were transduced and expanded in the modified RPMI (13 days). These cells expressed elevated levels of CD28, which is known to be associated with better expansion and persistence upon adoptive transfer, than cells cultured in regular RPMI medium ($N=4$, $P<0.01$). This change was mainly reflected in the CD4 subset (FIG. 16A), which is consistent with the dominant CD4 CAR persistence in the in vivo experiment. No differences in exhaustion were observed between the two culture conditions (FIG. 16A). Based on these data, CD19-CAR T cells were cultured in RPMI and human CSF for 48 hours in the presence of target Daudi cells. As shown in FIG. 16B, CD19-CAR T cells in CSF tend to express comparable levels of exhaustion markers as those in RPMI, but higher levels of memory markers, such as IL-7alpha. These observations were consistent among cells collected from four different healthy donors, and indicate that metabolic conditions may contribute to better CAR T cell function through T cell lineage polarization and improved CAR T cell memory of ICV infused CAR T cells.

Figure 16C:
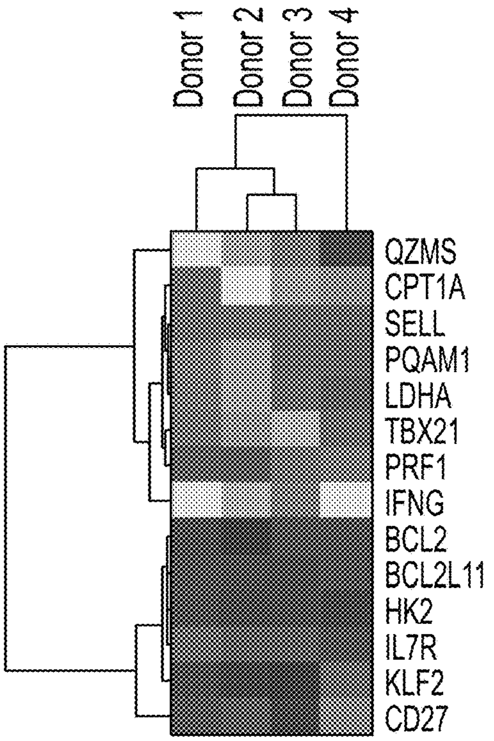

Next, CD19-CAR T cells were cultured in in RPMI and CSF for 48 hours and an RT-PCR array of genes associated with memory, effector function, and metabolism was run. Across 4 different donors, elevated expression (>1.3 fold change) of genes related to better survival and memory function, such as BCL2, BCL2L11 KLF2, and IL7Ralpha (CD127) was observed and decreased expression of terminal differentiation genes like PRF1, IFNgamma, GZMB, and TBX21 (>1.3 fold change) was observed in the cells treated with CSF when compared with RPMI treated CAR T cells (FIG. 16C). In spite of upregulated HK2, which may be due to compensation for the low glucose condition, glycolytic flux enhancer, Pgam-1, that impairs the memory T cell formation, was downregulated in CSF cultures. In addition, numerous other genes regulating glucose metabolism such as CPT1A, an enzyme that controls the rate-limiting step for fatty oxidation (FAO) and glycolysis was decreased. Along with down regulated LDHA, the metabolic pathway of CAR T cells in CSF may switch to mitochondrial oxidative phosphorylation as the main source of ATP, favoring the establishment of T cell memory that is supported by elongated mitochondria in ICV CAR T cells as shown in FIGS. 14A-14D.

Figure 16D:
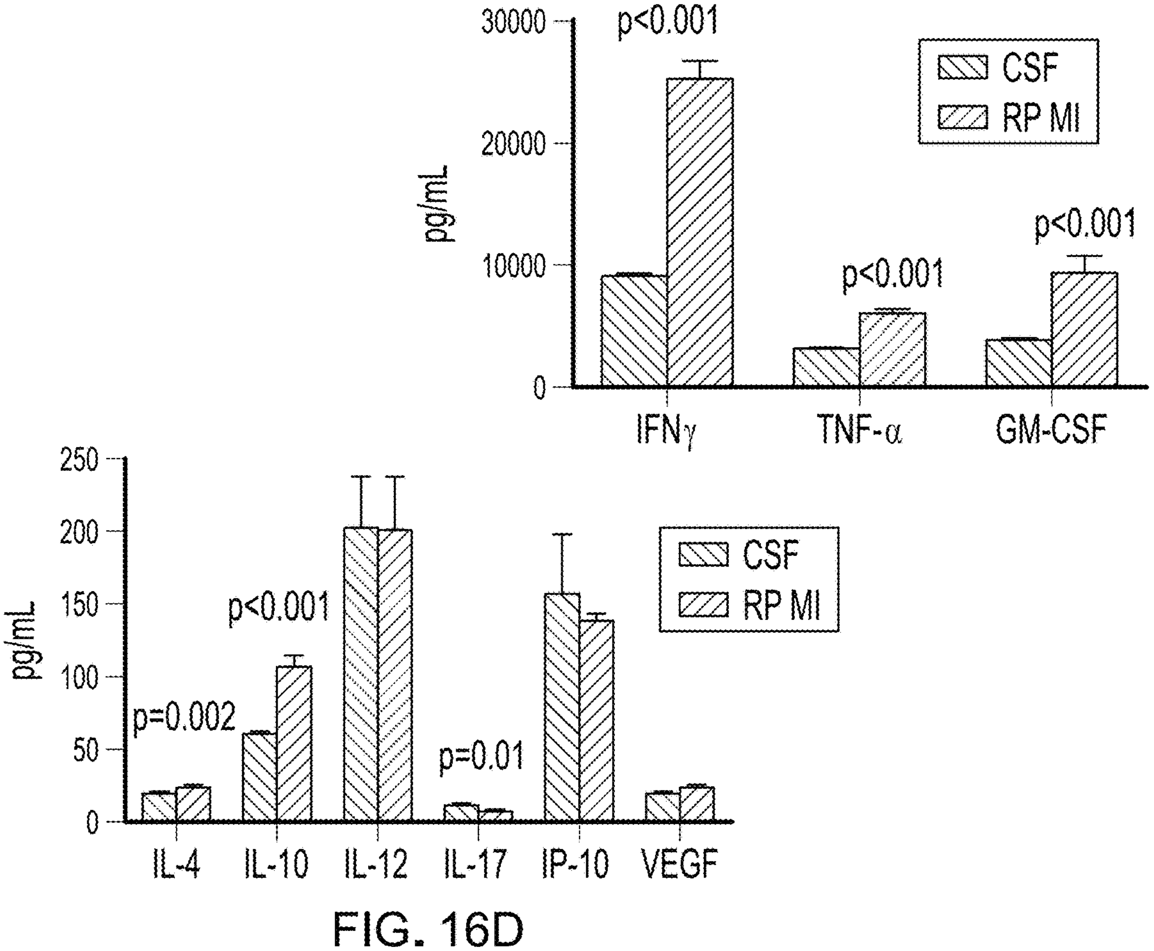

Furthermore, CAR T cells treated in CSF tend to produced significantly lower levels of effector cell related and T cell inhibitory cytokines upon stimulation with Daudi cells (FIG. 16D), a finding consistent with the transcriptional profiles of less differentiated cells treated with CSF (FIG. 16C). When CAR T cells were stimulated with microbeads coated with soluble CD19 protein, which is recognized by CD19 CAR scFv (FMC63), and used as stimulator for CAR T cells at a ratio of 1:1 in RPMI and CSF for 48 hours, cells in CSF expressed upregulated activation-related genes, such as PRDM1, PDCD1, and FOXP3, but simultaneously also upregulated KLRB1 (CD161), BCL2 and down regulated B3GAT1(CD57) ppp2r2, GZMB, EOMES, and again, the low glycolytic gene, CPT1A. Overall, the data here suggest that conditions in the CSF can reprogram CD19-CAR T cells through upregulation of memory genes and down regulation of glycolysis-associated genes, resulting in a unique CAR T cell population that is fully activated for immediate antitumor function as well as acquired memory function.

Example 18

Figure 17C:
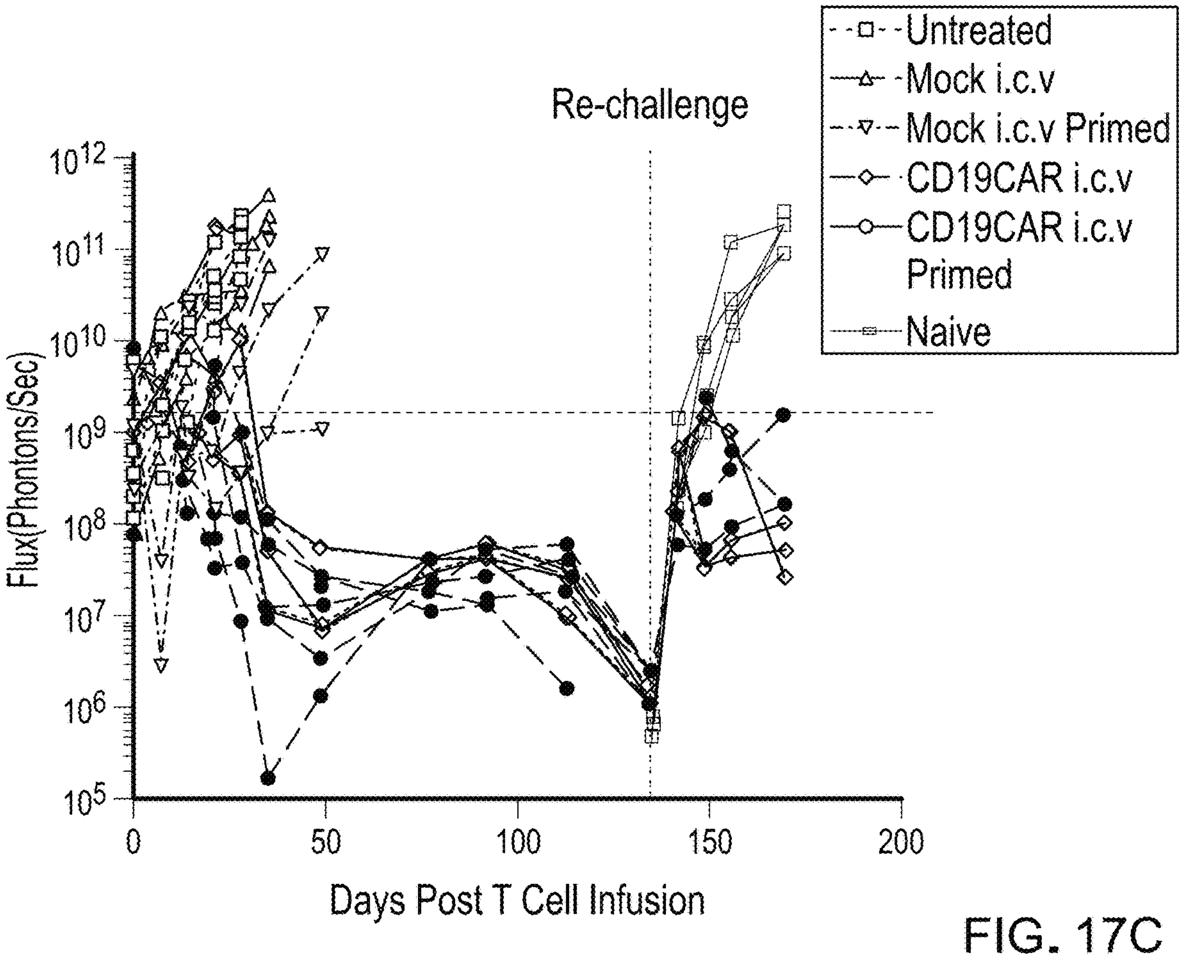
Figure 17D:
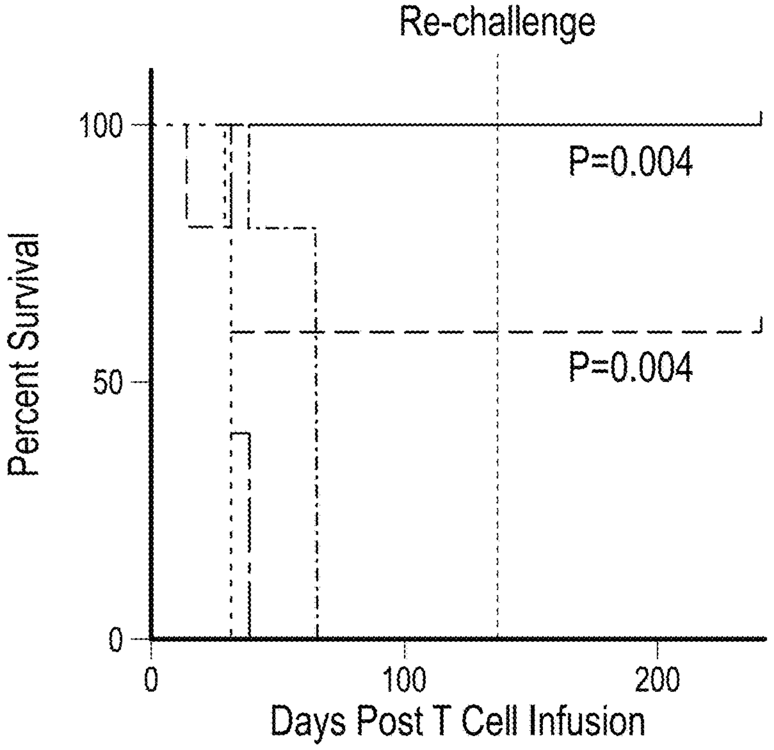

Antigen-Primed CAR T Cells Possess Memory Phenotype and are Able to Resist Tumor Re-Challenge As shown above, ICV CAR T cells not only efficiently eradicate brain tumor, but also systemic lymphoma. To elucidate whether this is the result of CSF reprograming alone or a combination effect with T cell activation by the brain tumor before they migrate to the peripheral blood, an in vitro priming model was developed by co-culturing CAR T cells with irradiated tumor cells for 1 hour before injecting via ICV into mice bearing s.c. tumor in right flanks. Flank tumors showed faster regression in mice treated with in vitro primed CD19-CAR T cells as compared to those treated with un-primed CD19-CAR T cells ($P=0.003$) (FIG. 17A and FIG. 17D). 133 days post CAR infusion, the surviving mice were re-challenged with new tumor. 100% of primed and 60% un-primed CAR T treated mice remained tumor free for more than 200 days following re-challenge (FIGS. 17C-D), indicating that CSF alone is able to improve antitumor activity and antigen priming would further enhance antitumor activity and T cell memory.

Figure 17E:
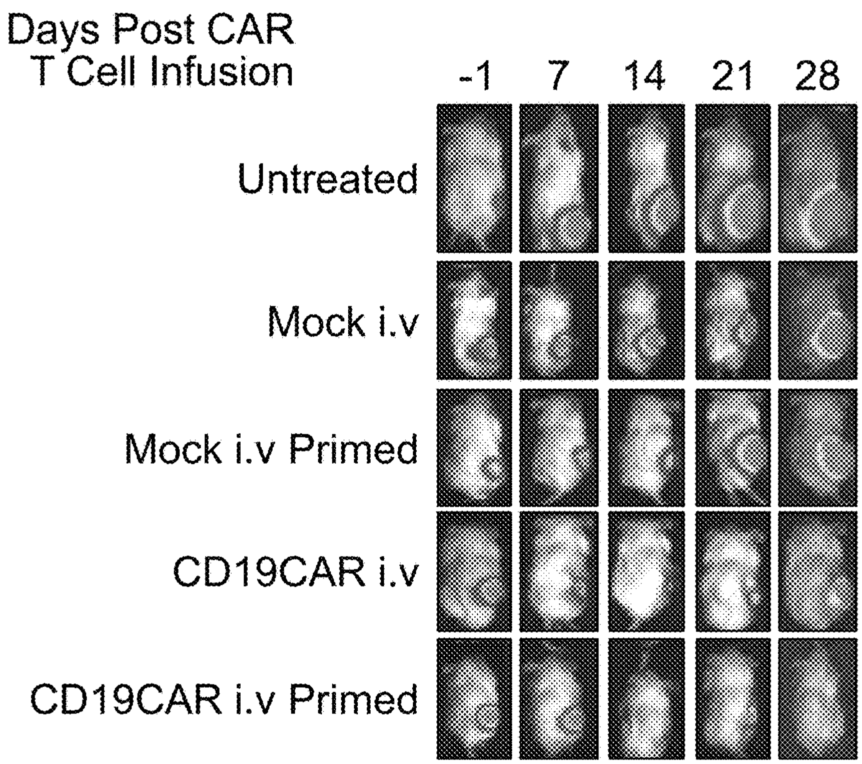
Figure 17F:
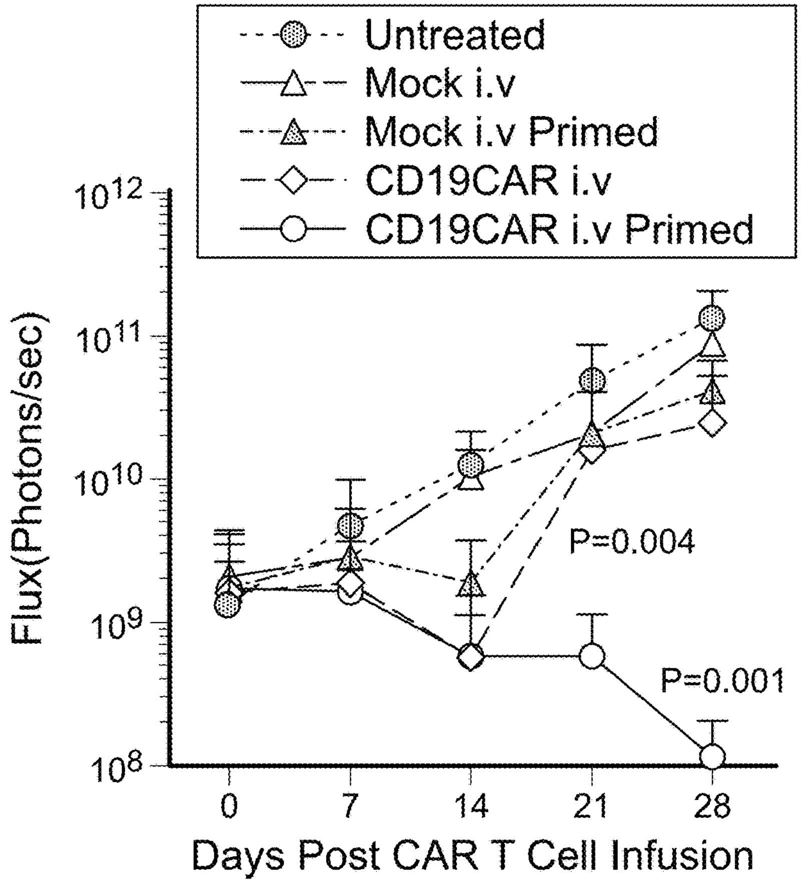
Figure 17G:
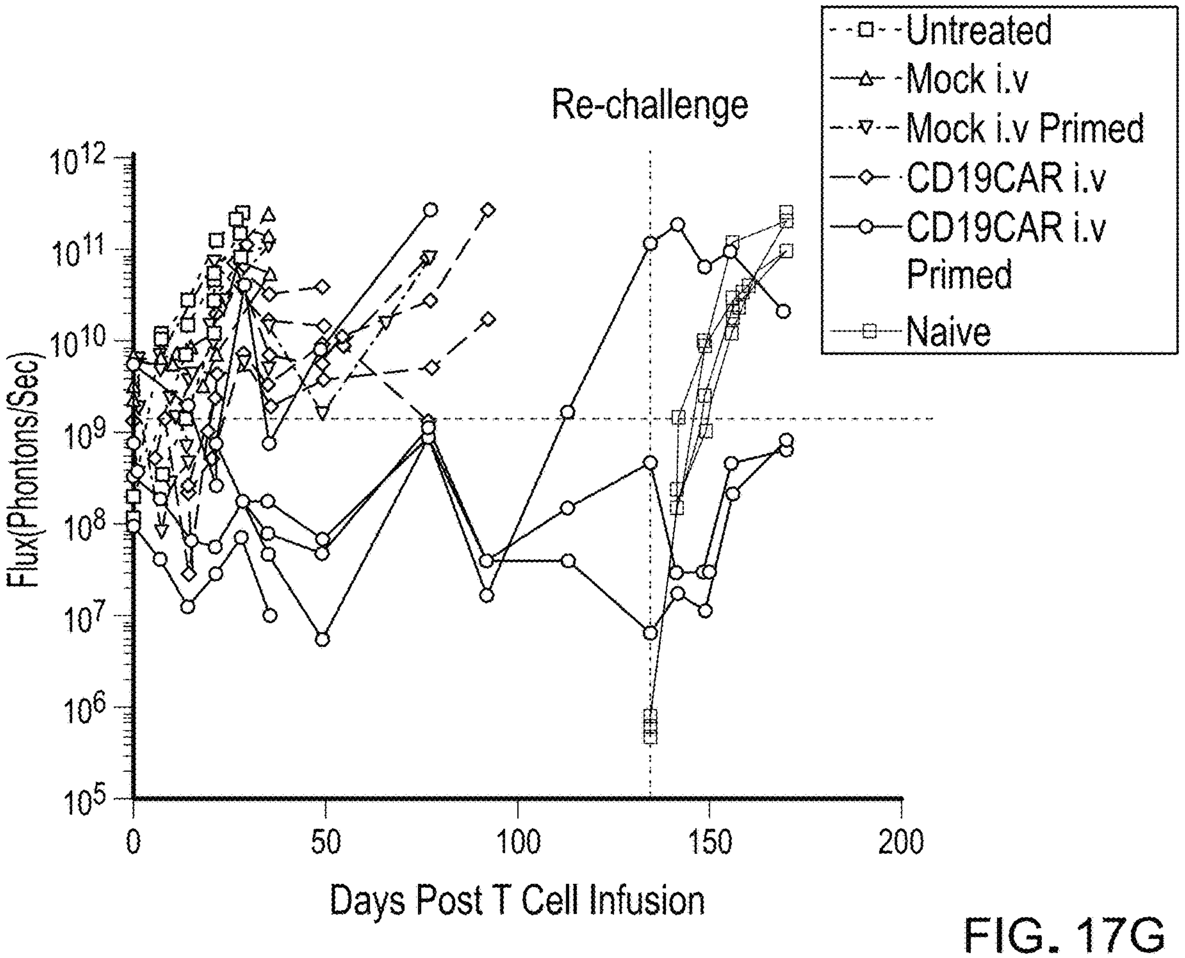
Figure 17H:
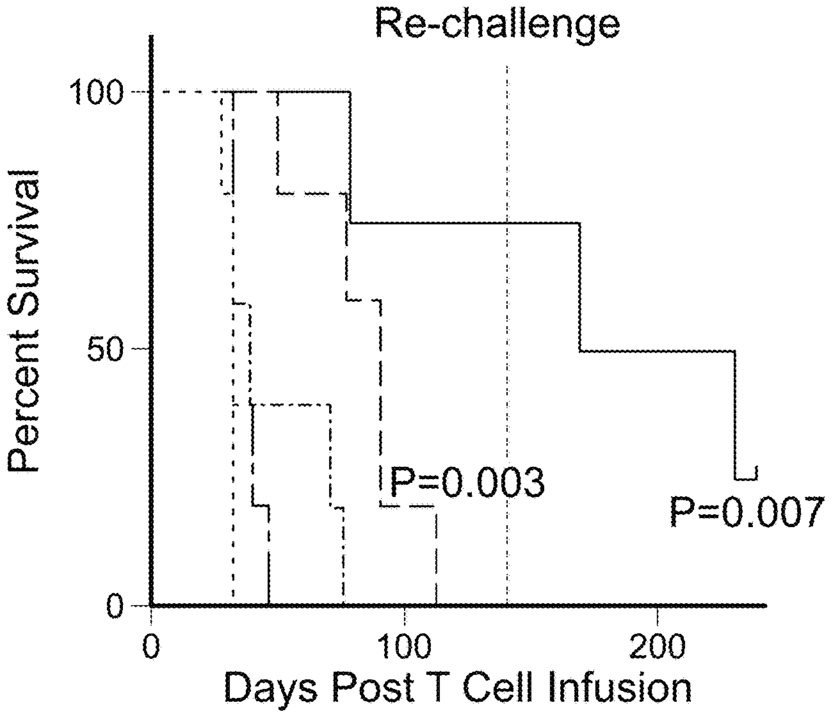
Figure 18B:
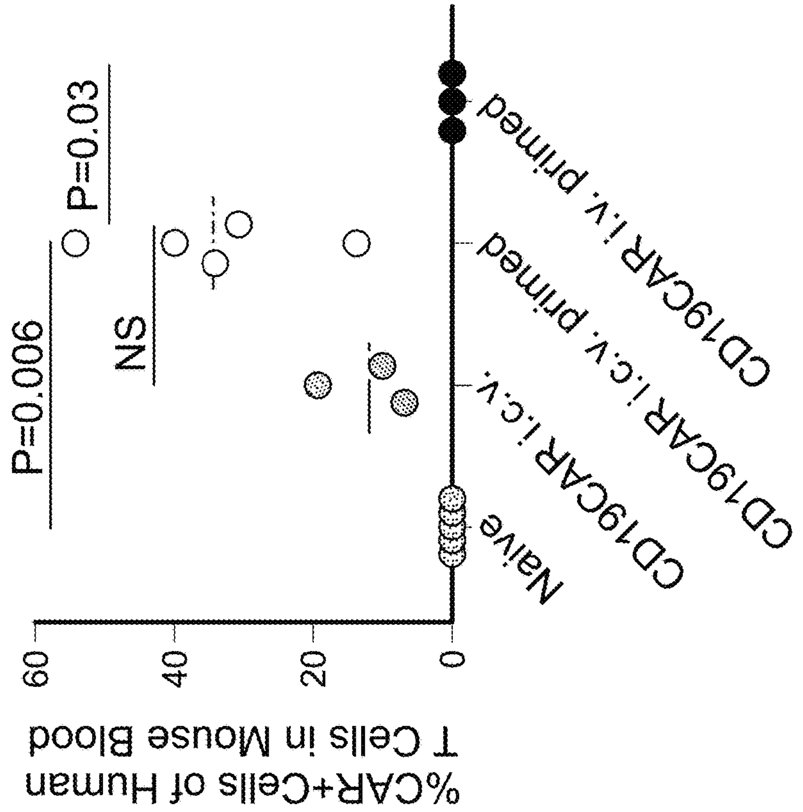
FIGS. 18A-18B: Antigen primed CAR T cells persist better than unprimed CAR T cells. NSG mice were inoculated with $3\times10^6$ Daudi cells SC on the right flank 19 days prior to CAR T cell treatment. On the day of CAR T cell infusion, $2\times10^6$ CD19-CAR T cells were primed with irradiated Daudi cells at a 10:1 (CAR:tumor) ratio for 1 hr and then infused into tumor bearing mice through ICV and IV injection. Mock T cells were used as controls. 133 days post CAR T treatment, blood was collected retro orbitally and analyzed by flow cytometry after staining with antibodies against human CD45 and CAR (EGFR). The Mann-Whitney test was used to ascertain statistical significance (A-B).
Figure 18A:
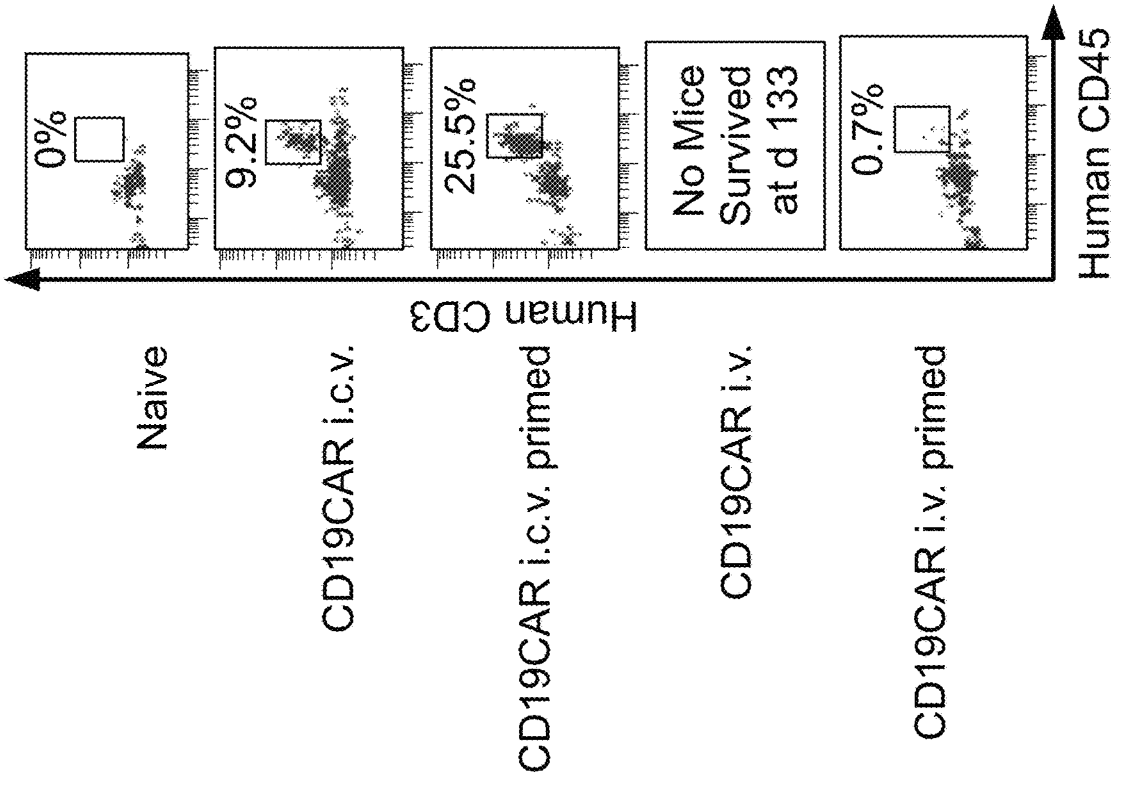

Because the enhanced CAR T cell function after antigen priming could be independent of CSF, CD19-CAR T cells were primed and administered them intravenously. Mice with systemic tumors (s.c.) were treated with primed and un-primed CD19-CAR T cells. Consistent with previous observations, primed CAR T cells induced better tumor regression when compared with unprimed CAR T cells ($P<0.01$) (FIGS. 17E-F). All mice that received un-primed CD19-CAR T cells died before or around day 90. In contrast, three of the five mice that received primed CAR T cells survived longer than 135 days and two of these three mice resisted tumor re-challenge (FIG. 17G). Regardless of significantly prolonged survival ($p<0.01$) when compared with un-primed CAR T cell-treated mice, mice receiving primed CAR T cells start to decline around 200 days (FIG. 17H), which is inferior survival when compared to their ICV counter parts. Along with the improved efficacy of primed CAR T cells, 133 days after CAR T cell infusion, there are significantly higher levels of CAR T cells persisting in the primed ICV treated mice than that of unprimed ICV and primed IV CAR treated mice (FIGS. 18A-B). This data support the hypothesis that both CSF reprograming and T cell activation by the brain tumor synergistically augment CAR T cell antitumor efficacy.

Methods and Materials

Antibodies and Flow Cytometry Fluorochrome-conjugated isotype controls against CD3, CD4, CD8, PD1, KLRG, CD28, CD62L, CD127, and streptavidin-PE were obtained from BD Biosciences. The antibody against EGFR was purchased from BioLegend. Biotinylated Erbitux was generated from cetuximab purchased from the City of Hope pharmacy. The IOTestBeta Mark TCR Vβ Repertoire Kits (representing ~70% of normal TCR repertoire) were obtained from Beckman Coulter. Isotype-matched mAbs served as controls. Data acquisition was performed on a MACSquant (Miltenyi) and analyzed using FCS Express Version 3 software (De Novo Software). 2-NBDG was obtained from Fisher Scientific.

Lentivirus Vector Construction and CAR T cell generation The lentivirus CAR construct was modified from the previously described CD19-specific scFvFc:ζ chimeric immunoreceptor (Kowolik et al. 2006 *Cancer Research* 66:10995). The CD19R:CD28:ζ/EGFRt-epHIV7 contains: 1) the CAR sequence consisting of the $V_H$ and $V_L$ gene segments of the CD19-specific FMC63 mAb, an IgG4 hinge with mutations at two sites (L235E; N297Q) within the $CH_2$ region, the transmembrane and cytoplasmic domains of the costimulatory molecule, CD28, and the cytoplasmic domain of the CD3ζ chain; 2) the ribosomal skip T2A sequence; and 3) the truncated human EGFR (EGFRt) sequence. Leukapheresis products were obtained from healthy donors using protocols approved by the City of Hope Institutional Review Board. Naïve and central memory T cells defined as CD62L+CD14− were isolated on a Miltenyi CliniMACS (Miltenyi Biotec, Inc.). Briefly, Leukapheresis products were obtained from consented healthy donors, PBMC were isolated by density gradient centrifugation over Ficoll-Paque (GE Healthcare), and incubated with anti-CD14 microbeads (Miltenyi Biotec, Inc.) for 30 minutes at RT. CD14+ cells were then immediately depleted using the CliniMACS™. The unlabeled negative fraction of cells was labeled with biotinylated-DREG56 mAb (COH CBG) followed by incubation with anti-biotin microbeads (Miltenyi Biotec, Inc.). The $CD62L^+$ cells were purified with positive selection on the CliniMACS™. Right after selection, the T cells were activated, transduced, and maintained as described (Wang 2012 *J Immunotherapy* 35:689). In some experiments, CAR T cells were transduced to express ffluc and GFP.

Reverse transcriptase (RT) quantitative PCR (qPCR) analysis RNA was extracted with RNeasy Kits (Qiagen). RT-qPCR was performed using the $RT^2$ Profiler PCR Array (SABiosciences) designed with customized primers for sequences of transcriptionally regulated genes shown to impart differentiation, survival, metabolism, and apoptotic attributes to CAR T cells (Hinrichs C S, Blood 2011; Willinger T J Immunol 2005). Four control genes, including housekeeping genes PPIA (Peptidylprolyl isomerase A; cyclophilin A), RPL13A (Ribosomal protein L13a), control for reverse transcription, a positive PCR control were also used. All samples passed RNA quality control, PCR array reproducibility, RT efficiency, and genomic DNA contamination tests performed according to the manufacturer's instructions. Data were analyzed by ΔΔCt method using $RT^2$ Profiler PCR Array Web portal software (www.sabiosciences.com). Median fold change of CSF versus RPMI cultured CAR T cells from 4 individual donors are presented. Hierarchical clustering analysis was performed in Cluster 3.0 using the average linkage clustering method, with genes demonstrating an absolute fold change larger than 1.3. The results were then visualized in Treeview 1.1.6r4 and a heatmap was generated.

Cytokine production assays Expanded CAR T cell products ($10^5$) were co-cultured in 96-well tissue culture plates with $10^5$ CD19+ stimulator cells (Daudi). Supernatants were harvested 18 h after stimulation and analyzed in triplicates by cytometric bead array using the Bio-Plex Human Cytokine 17-Plex Panel (Bio-Rad Laboratories) according to the manufacturer's instructions.

NBDG uptake assays 2-NBDG is a fluorescent glucose analog that has been used to monitor glucose uptake in live cells. NBDG fluorescence typically displays excitation/emission maxima of ~465/540 nm and can be visualized using a FACS machine with a green/FITC channel. Cells were washed with warm PBS twice and stained with an APC-conjugated anti human CD62L antibody for 15 minutes at RT. After staining, the cells were washed two times with warm PBS. The cells were then cultured in 100 μM 2-NBDG PBS buffer for 10 minutes and 30 minutes in a 5% $CO_2$ incubator at 37° C. After two washes with PBS, the cells were analyzed with the MACquant.

Immunohistochemistry staining (IHC) Fresh tissue was collected from mice with flank (s.c.) tumors, fast frozen, and embedded in O.C.T. The tumor tissue was cut into 10 μM thick sections and placed on slides. To detect CAR T cells within the tumor, the slides were double stained with primary antibodies for CD3 (LS-B8669, rabbit anti-human) and EGFR (280005, mouse anti-human). Briefly, air dried and fixed slides were blocked by 1% donkey serum in PBS buffer and incubated with primary antibodies against CD3 (1:200 dilution) and EGFR (1:100 dilution) at 4° C. overnight. Following staining with 488 Alexa Flour donkey anti-mouse and 555 Alexa Flour donkey anti-rabbit antibodies (Invitrogen) for 30 minutes in dark, the slides were stained with 0.1% DAPI for 3 minutes and covered with ProLong Gold Antifade Mountant (Invitrogen). The cell images were processed under a Zeiss Observer II microscope.

Spleens were also collected from tumor-bearing mice following CAR T cell treatment. Human T cells harvested from the mouse spleens were re-stimulated with REM method containing OKT3, irradiated PBMC, and lymphoblastoid cell lines (LCL) as previously described (Crossland K D, J Immunol 1991). The stimulated cells were stained in T cell medium with 100 nM MitoTracker (Green) Mitochondrial selective probe for 30 minutes at 37° C. The cells were then washed 3 times with warm X-vivo medium followed by washing with PBS containing 1% FBS. $1\times10^5$ cells were plated onto slides using a cytospin (700 RPM/h, 3 minutes) and the slides were dried overnight. The following day, cells were fixed with 4% PFA for 20 minutes and stained with DAPI for 1 minute. The mitochondrial images were taken using a LSM880 confocal microscope.

Orthotopic brain and systemic lymphoma xenograft model Six- to ten-week old NOD/Scid IL2RγC$^{mull}$ mice were injected intracranially and/or subcutaneously with $2\times10^6$ fflucGFP Daudi cells on day 0. Five days after intracranial injection and 19 days post subcutaneous injection, mice were treated with CD19 CAR T cells (i.v. or i.c.v.) or non-transduced mock cells. Anesthetized mice were imaged using a Xenogen IVIS 100 series system (Xenogen). Photons from ffLuc$^+$ tumor xenografts were quantified using the software program, Living Image (Xenogen), and the bioluminescence signal was measured as total photon flux normalized for exposure time and surface area and expressed in units of photons per second per cm$^2$ per steradian. Human T cell engraftment in peripheral blood, bone marrow, and spleen was determined by flow cytometry after staining with antibodies against human CD45, CD8, and CD3, and cetuximab for CAR detection.

Statistical Analysis Analyses were performed using Prism (GraphPad Software, Inc.). Log-rank (Mantel-Cox) test, Mann-Whitney test, and Kruskal-Wallis test were used to ascertain statistical significance of the in vivo data. The paired t-test (2-tailed) and two-way ANOVA were used for the statistical analysis of in vitro data.

What is claimed is:

1. A method of treating systemic lymphoma with concurrent central nervous system involvement or systemic B cell leukemia with concurrent central nervous system involvement, the method comprising administering into an intraventricular cavity of a patient in need thereof a composition comprising therapeutically effective amount of CD4+ and CD8+ T cells expressing a CD19 targeted chimeric antigen receptor (CAR) comprising a scFv that binds to CD19, a spacer domain, a transmembrane domain, a co-stimulatory domain, and a CD3ζ signaling domain.

2. The method of claim 1 wherein the T cells are autologous or allogenic T cells.

3. The method of claim 1 wherein the composition comprises at least $1\times10^6$ T cells expressing a CD19 targeted CAR.

4. The method of claim 1 wherein the composition comprising T cells is administered at least two times.

5. The method of claim 1 wherein the lymphoma is non-Hodgkin lymphoma.

6. The method of claim 1 wherein the CD19 targeted CAR comprises an amino acid sequence selected from the group consisting of SEQ ID NOs: 10, 1, 2, 4 and 5.

7. The method of claim 1 wherein the method is performed after myeloablative autologous hematopoietic stem cell transplantation.

8. The method of claim 1 wherein the T cells have undergone ex vivo expansion.

9. The method of claim 1 wherein the T cells comprise at least 10%, 20%, 30%, 40%, 50% or 60% central memory T cells and/or the T cells comprise at least 10%, 20%, 30%, 40%, 50% or 60% T naïve/memory cells.

10. The method of claim 1 wherein the scFv comprises SEQ ID NO:3.

11. The method of claim 1, wherein the spacer domain comprises any of SEQ ID NOs: 11-22, wherein the transmembrane domain comprises any of SEQ ID NOs: 22-29, wherein the co-stimulatory domain comprises any of SEQ ID NOs: 31-34, or wherein the CD32 signaling domain comprises SEQ ID NO:30.

12. The method of claim 1, wherein the CD19 CAR comprises the amino acid sequence of SEQ ID NO: 10 and an amino acid sequence of an ScFv that binds human CD19.

13. The method of claim 1, wherein the T cells expressing a CD19 targeted CAR are T cells that have been cultured in a culture medium having 60 mg/dL glucose and 2.8 mEq/L potassium.

14. The method of claim 13, wherein the T cells expressing a CD19 targeted CAR are T cells that have been activated by exposure to CD19 prior to administration or wherein the T cells expressing a CD19 targeted CAR are T cells that have been activated by exposure to cells expressing CD19 prior to administration.

15. The method of claim 1, wherein the T cells expressing a CD19 targeted CAR are T cells that have been activated by exposure to CD19 prior to administration or wherein the T cells expressing a CD19 targeted CAR are T cells that have been activated by exposure to cells expressing CD19 prior to administration.

16. The method of claim 1, wherein the CD19 scFv comprises SEQ ID NO: 3, the spacer comprises SEQ ID NO:20, the transmembrane domain comprises SEQ ID NO: 24, the co-stimulatory domain comprises SEQ ID NO:32, and the CD3 zeta domain comprises SEQ ID NO:30.

17. The method of claim 1, wherein the CD19 CAR comprises SEQ ID NO: 2.

18. The method of claim 1 wherein the T cells comprise at least 10%, 20%, 30%, 40%, 50% or 60% naïve T cells and memory T cells.

19. The method of claim 1, wherein the scFv comprises SEQ ID NO:3, the spacer domain comprises any of SEQ ID NOs: 11-22, wherein the transmembrane domain comprises any of SEQ ID NOs: 22-29, wherein the co-stimulatory domain comprises any of SEQ ID NOs: 31-34, or wherein the CD3ζ signaling domain comprises SEQ ID NO:30.

* * * * *